(12) United States Patent
Miyaji et al.

(10) Patent No.: US 7,968,542 B2
(45) Date of Patent: Jun. 28, 2011

(54) THIOPHENE COMPOUNDS AND THROMBOPOIETIN RECEPTOR ACTIVATORS

(75) Inventors: Katsuaki Miyaji, Funabashi (JP); Kazufumi Yanagihara, Funabashi (JP); Yukihiro Shigeta, Funabashi (JP); Shunsuke Iwamoto, Funabashi (JP); Masato Horikawa, Minami-saitama-gun (JP); Yutaka Hirokawa, Funabashi (JP); Shingo Owada, Funabashi (JP); Satoshi Nakano, Funabashi (JP); Hirofumi Ota, Funabashi (JP); Norihisa Ishiwata, Minami-saitama-gun (JP)

(73) Assignee: Nissan Chemical Industries, Ltd., Tokyo (JP)

(*) Notice: Subject to any disclaimer, the term of this patent is extended or adjusted under 35 U.S.C. 154(b) by 16 days.

(21) Appl. No.: 11/994,502

(22) PCT Filed: Jul. 13, 2006

(86) PCT No.: PCT/JP2006/314317
§ 371 (c)(1),
(2), (4) Date: Jan. 3, 2008

(87) PCT Pub. No.: WO2007/010954
PCT Pub. Date: Jan. 25, 2007

(65) Prior Publication Data
US 2009/0118500 A1    May 7, 2009

(30) Foreign Application Priority Data

| Jul. 15, 2005 | (JP) | ................................. 2005-206822 |
| Jul. 15, 2005 | (JP) | ................................. 2005-206823 |
| Mar. 24, 2006 | (JP) | ................................. 2006-083770 |
| Mar. 24, 2006 | (JP) | ................................. 2006-083771 |
| Apr. 19, 2006 | (JP) | ................................. 2006-115569 |

(51) Int. Cl.
*C07D 401/14* (2006.01)
*C07D 409/14* (2006.01)
*C07D 413/14* (2006.01)
*A61K 31/381* (2006.01)
*A61P 7/00* (2006.01)

(52) U.S. Cl. ................ 514/231.5; 514/255.01; 514/378; 514/397; 514/422; 514/444; 544/146; 544/379; 546/280.4; 548/240; 548/365.7; 548/530; 549/59; 549/60

(58) Field of Classification Search .................. None
See application file for complete search history.

(56) References Cited

U.S. PATENT DOCUMENTS

| 7,351,841 B2 * | 4/2008 | Owada et al. ................... 549/62 |
| 2003/0195231 A1 | 10/2003 | Takemoto et al. |
| 2004/0063764 A1 | 4/2004 | Takemoto et al. |
| 2004/0077697 A1 | 4/2004 | Koshio et al. |
| 2004/0082626 A1 | 4/2004 | Takemoto et al. |
| 2005/0153977 A1 | 7/2005 | Sugasawa et al. |

FOREIGN PATENT DOCUMENTS

| EP | 1 207 155 A1 | 5/2002 |
| JP | 10-72492 | 3/1998 |
| JP | 11-1477 | 1/1999 |
| JP | 11-152276 | 6/1999 |
| JP | 2001-97948 | 4/2001 |
| JP | 2003/238565 | 8/2003 |
| WO | WO 96/40189 | 12/1996 |
| WO | WO 96/40750 | 12/1996 |
| WO | WO 98/25965 | 6/1998 |
| WO | WO 99/11262 | 3/1999 |
| WO | WO 00/35446 | 6/2000 |
| WO | WO 00/66112 | 11/2000 |
| WO | WO 01/07423 A1 | 2/2001 |
| WO | WO 01/17349 A1 | 3/2001 |
| WO | WO 01/21180 A1 | 3/2001 |
| WO | WO 01/34585 A1 | 5/2001 |
| WO | WO 01/39773 A1 | 6/2001 |
| WO | WO 01/53267 A1 | 7/2001 |
| WO | WO 01/89457 A2 | 11/2001 |
| WO | WO 02/49413 A2 | 6/2002 |
| WO | WO 02/059099 A1 | 8/2002 |
| WO | WO 02/059100 A1 | 8/2002 |
| WO | WO 02/062775 A1 | 8/2002 |
| WO | WO 02/085343 A1 | 10/2002 |
| WO | WO 03/062233 A1 | 7/2003 |
| WO | 2004 033433 | 4/2004 |
| WO | WO 2004/033433 A1 | 4/2004 |
| WO | 2004 108683 | 12/2004 |
| WO | WO 2004/108683 A1 | 12/2004 |
| WO | 2006 064957 | 6/2006 |
| WO | WO 2006/064957 A1 | 6/2006 |

OTHER PUBLICATIONS

Kaushansky, Kenneth, "Thrombopoietin", New England Journal of Medicine, 746-754, Sep. 10, 1998.* van den Oudenrijn, Thrombopoietin Receptor, retrieved Jan. 18, 2007 fro internet, ,http://mpr.nci.nih.gov/prow/guide/11586825_g.htm., Protein Reviews On the Wev, p. 1-6.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*

(Continued)

*Primary Examiner* — Fiona T Powers
(74) *Attorney, Agent, or Firm* — Oblon, Spivak, McClelland, Maier & Neustadt, L.L.P.

(57) ABSTRACT

A compound represented by the formula (I) (wherein $R_1$, $R_2$, $R_3$ and $R_4$ are as defined in the description), a tautomer, prodrug or pharmaceutically acceptable salt of the compound or a solvate thereof.

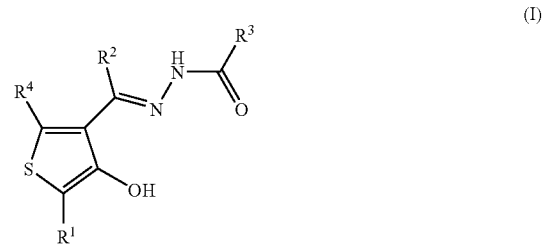

(I)

37 Claims, No Drawings

OTHER PUBLICATIONS

Vippagunta et al., Advanced Drug Delivery Reviews, 48 (2001), pp. 3-26.*

Jose E. Cardier, "Effects of Megakaryocyte Growth and Development Factor (Thrombopoietin) on Liver Endothelial Cells in Vitro", Microvascular Research, vol. 58, 1999, pp. 108-113.

Maria Felice Brizzi, et al., "Thrombopoietin Stimulates Endothelial Cell Motility and Neoangiogenesis by a Platelet-Activating Factor-Dependent Mechanism", Circulation Research, vol. 84, 1999, pp. 785-796.

"Blood", Journal of the American Society of Hematology, vol. 98, No. 11, Nov. 16, 2001, pp. 71a-72a and a cover page.

U.S. Appl. No. 12/303,436, filed Dec. 4, 2008, Miyaji, et al.

U.S. Appl. No. 12/492,435, filed Jun. 26, 2009, Owada, et al.

* cited by examiner

THIOPHENE COMPOUNDS AND THROMBOPOIETIN RECEPTOR ACTIVATORS

BACKGROUND OF THE INVENTION

1. Technical Field

The present invention relates to preventive, therapeutic and improving agents having affinity for and agonistic action on the thrombopoietin receptor for diseases against which activation of the thrombopoietin receptor is effective. Specifically, it relates to pharmaceutical compositions comprising compounds which increase platelets through stimulation of differentiation and proliferation of hematopoietic stem cells, megakaryocytic progenitor cells and megakaryocytes or compounds for therapeutic angiogenesis or with anti-arteriosclerosis action that stimulate differentiation and proliferation of vascular endothelial cells and endothelial progenitor cells.

2. Background Art

Thrombopoietin is a cytokine consisting of 332 amino acids that increases platelet production by stimulating differentiation and proliferation of hematopoietic stem cells, megakaryocytic progenitor cells and megakaryocytes mediated by its receptor and therefore is promising as a drug for hematological disorders. Recent reports that it stimulates differentiation and proliferation of vascular endothelial cells and endothelial progenitor cells have raised expectations of therapeutic angiogenesis, anti-arteriosclerosis and prevention of cardiovascular events (for example, non-patent document 1, non-patent document 2 and non-patent document 3).

Biologically active substances which have been known so far to regulate platelet production through the thrombopoietin receptor include, in addition to thrombopoietin itself, low molecular weight peptides having affinity for the thrombopoietin receptor (for example, patent document 1, patent document 2, patent document 3 and patent document 4).

As a result of search for nonpeptidic low molecular weight compounds that increase platelet production mediated by the thrombopoietin receptor, low molecular weight compounds having affinity for the thrombopoietin receptor have been reported (for example, patent document 5 to patent document 26).

1) Applications filed by Hokuriku Seiyaku Co., Ltd. relating to 1,4-benzodiazepine derivatives (patent documents 5 and 6)
2) International Laid-open Patent Applications filed by Shionogi & Co., Ltd. (patent documents 7-10)
3) International Laid-open Patent Applications filed by SmithKline Beecham Corp (patent documents 11-19)
4) Japanese Laid-open Patent Application filed by Torii Pharmaceutical Co., Ltd. (patent document 20)
5) International Laid-open Patent Application filed by Roche Diagnostics GMBH (patent document 21)
6) International Laid-open Patent Applications filed by Yamanouchi Pharmaceutical Co., Ltd. (patent document 22 and 23)
7) Japanese Laid-open Patent Application filed by Japan Tabacco Inc. (patent document 24)
8) International Laid-open Patent Application filed by Nissan Chemical Industries, Ltd. (patent documents 25 and 26)

Patent document 1 JP-A-10-72492
Patent document 2 WO96/40750
Patent document 3 WO96/40189
Patent document 4 WO98/25965
Patent document 5 JP-A-11-1477
Patent document 6 JP-A-11-152276
Patent document 7 WO01/07423
Patent document 8 WO01/53267
Patent document 9 WO02/059099
Patent document 10 WO02/059100
Patent document 11 WO00/35446
Patent document 12 WO00/66112
Patent document 13 WO01/34585
Patent document 14 WO00/17349
Patent document 15 WO01/39773
Patent document 16 WO01/21180
Patent document 17 WO01/89457
Patent document 18 WO02/49413
Patent document 19 WO02/085343
Patent document 20 JP-A-2001-97948
Patent document 21 WO99/11262
Patent document 22 WO02/062775
Patent document 23 WO03/062233
Patent document 24 JP-A-2003-238565
Patent document 25 WO04/033433
Patent document 26 WO04/108683
Non-patent document 1 Microvasc. Res., 1999: 58, p. 108-113
Non-patent document 2 Circ. Res., 1999: 84, p. 785-796
Non-patent document 3 Blood 2001:98, p. 71a-72a

DISCLOSURE OF THE INVENTION

Thrombopoietin and low molecular weight peptides having affinity for the thrombopoietin receptor are likely to be easily degraded in the gastrointestinal tract and are usually difficult to orally administer. As to thrombopoietin itself, the appearance of anti-thrombopoietin antibodies have been reported.

Besides, though it is probably possible to orally administer nonpeptidic low molecular weight compounds, no practical drugs have been put on the market.

Therefore, orally administrable low molecular weight compounds having excellent affinity for and agonistic action on the thrombopoietin receptor as preventive, therapeutic and improving agents for diseases against which activation of the thrombopoietin receptor is effective have been demanded. Specifically, low molecular weight compounds which can serve as platelet increasing agents or increasing agents for other blood cells by stimulating differentiation and proliferation of hematopoietic stem cells, megakaryocytic progenitor cells and megakaryocytes or low molecular weight compounds which can be used for therapeutic angiogenesis or as preventive and therapeutic agents for arteriosclerosis by stimulating endothelial cells and endothelial progenitor cells have been demanded.

The present inventors conducted extensive research to find low molecular weight compounds having affinity for and agonistic action on the thrombopoietin receptor, and as a result, found that the compounds of the present invention have high affinity and agonistic action which enable them to show potent platelet increasing action by stimulating differentiation and proliferation of megakaryocytic progenitor cells and megakaryocytes. The present invention was accomplished on the basis of this discovery.

Namely, the present invention relates to:
1. A compound represented by the formula (I):

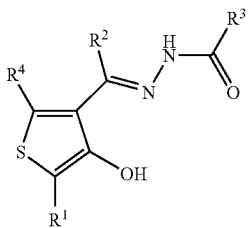

wherein $R^1$ is a phenyl group (the phenyl group may be substituted with one or more $C_{1-6}$ alkyl groups, one or more $C_{1-3}$ alkyl groups (the $C_{1-3}$ alkyl groups are substituted with one or more halogen atoms), one or more $C_{1-3}$ alkoxy groups (the $C_{1-3}$ alkoxy groups may be substituted with one or more halogen atoms) or one or more halogen atoms),
$R^2$ is a hydrogen atom or a $C_{1-3}$ alkyl group (the $C_{1-3}$ alkyl group may be substituted with one or more halogen atoms),
$R^3$ is a phenyl group, a pyridyl group or a thienyl group (the phenyl group, the pyridyl group and the thienyl group are substituted with one or more substituents selected from the group consisting of hydrogen atoms, nitro groups, halogen atoms and $C_{1-3}$ alkyl groups (the $C_{1-3}$ alkyl groups may be substituted with one or more halogen atoms) and with (C=O)$R^5$ (wherein $R^5$ is $NR^6R^7$ (wherein $R^6$ is a hydrogen atom or a $C_{1-3}$ alkyl group (the $C_{1-3}$ alkyl group may be substituted with one or more halogen atoms), and $R^7$ is a $C_{1-6}$ alkyl group (the $C_{1-6}$ alkyl group may be substituted with one or more halogen atoms, one or more hydroxyl groups, one or more $C_{1-3}$ alkoxy groups or one or more $C_{2-14}$ aryl groups (the $C_{2-14}$ aryl groups may be substituted with one or more $C_{1-3}$ alkyl groups, one or more $C_{1-3}$ alkoxy groups, one or more carboxyl groups, one or more carbamoyl groups, one or more cyano groups or one or more halogen atoms, and in the case of aryl groups containing one or more nitrogen atoms, may be N-oxides thereof)), a phenyl group, a thienyl group, a pyridyl group or a pyridyl-N-oxide group (the phenyl group, the thienyl group, the pyridyl group and the pyridyl-N-oxide group may be substituted with one or more halogen atoms), or $NR^6R^7$ is, as a whole, a nitrogen-containing heterocyclyl group (the nitrogen-containing heterocyclyl group may be substituted with one or more hydrogen atoms, one or more $C_{1-6}$ alkyl groups (the $C_{1-6}$ alkyl groups may be substituted with one or more halogen atoms), one or more halogen atoms, one or more hydroxyl groups or one or more $C_{1-3}$ alkoxy groups (the $C_{1-3}$ alkoxy groups may be substituted with one or more halogen atoms))) or a $C_{1-6}$ alkyl group (the $C_{1-6}$ alkyl group may be substituted with one or more halogen atoms, one or more pyridyl groups, one or more pyridyl-N-oxide groups, one or more furyl groups, one or more thienyl groups or one or more phenyl groups and is substituted with one or more cyano groups))), and
$R^4$ is a hydrogen atom or a $C_{1-3}$ alkyl group (the $C_{1-3}$ alkyl group may be substituted with one or more halogen atoms), a tautomer, prodrug or pharmaceutically acceptable salt of the compound or a solvate thereof.
2. The compound according to 1, wherein $R^2$ is a methyl group, and $R^4$ is a hydrogen atom, a tautomer, prodrug or pharmaceutically acceptable salt of the compound or a solvate thereof.
3. The compound according to 2, wherein $R^1$ is a 3,4-dimethyl-phenyl group, a 4-t-butyl-phenyl group, a 4-trifluorom-ethyl-phenyl group, a 3-chloro-phenyl group, a 4-chloro-phenyl group, a 4-fluoro-phenyl group, a 3,4-dichloro-phenyl group, a 4-bromo-phenyl group or a 4-trifluoromethoxy-phenyl group, a tautomer, prodrug or pharmaceutically acceptable salt of the compound or a solvate thereof.
4. The compound according to 3, wherein $R^3$ is represented by the formula (II):

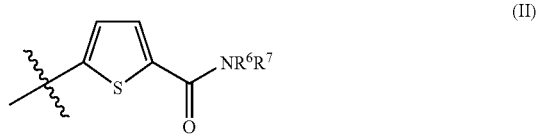

(wherein $R^6$ is a methyl group or an ethyl group, and $R^7$ is a $C_{1-6}$ alkyl group (the $C_{1-6}$ alkyl group may be substituted with one or more methoxy groups)), a tautomer, prodrug or pharmaceutically acceptable salt of the compound or a solvate thereof.

5. The compound according to 3, wherein $R^3$ is represented by the formula (II):

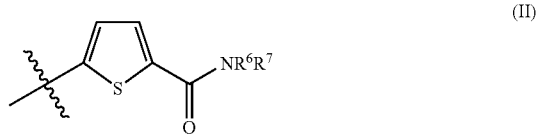

(wherein $R^6$ is a methyl group or an ethyl group, and $R^7$ is a $C_{1-3}$ alkyl group (the $C_{1-3}$ alkyl group is substituted with one or more phenyl groups or one or more pyridyl groups)), a tautomer, prodrug or pharmaceutically acceptable salt of the compound or a solvate thereof.

6. The compound according to 3, wherein $R^3$ is represented by the formula (II):

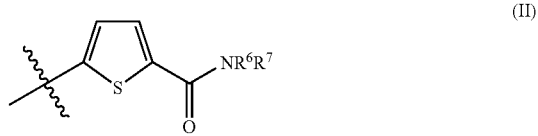

(wherein $R^6$ is a hydrogen atom, and $R^7$ is a $C_{1-6}$ alkyl group (the $C_{1-6}$ alkyl group is substituted with one or more methoxy groups) or a pyridyl group), a tautomer, prodrug or pharmaceutically acceptable salt of the compound or a solvate thereof.

7. The compound according to 3, wherein $R^3$ is represented by the formula (II):

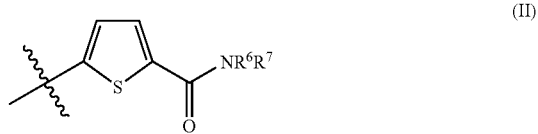

(wherein NR⁶R⁷ is, as a whole, represented by the formula (III):

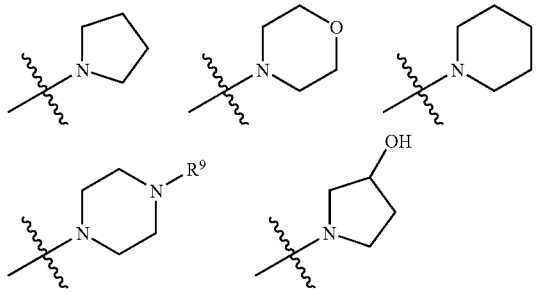

(wherein R⁹ is a $C_{1-3}$ alkyl group)), a tautomer, prodrug or pharmaceutically acceptable salt of the compound or a solvate thereof.

8. The compound according to 3, wherein R³ is represented by the formula (IV):

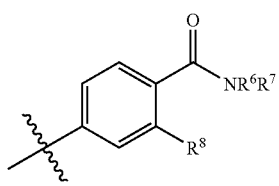

(wherein R⁶ is a hydrogen atom, R⁷ is a $C_{1-3}$ alkyl group (the $C_{1-3}$ alkyl group may be substituted with one or more hydroxyl groups), and R⁸ is a methyl group or a chlorine atom), a tautomer, prodrug or pharmaceutically acceptable salt of the compound or a solvate thereof.

9. The compound according to 3, wherein R³ is represented by the formula (V):

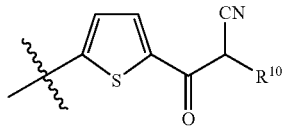

(wherein R¹⁰ is a hydrogen atom or a $C_{1-3}$ alkyl group), a tautomer, prodrug or pharmaceutically acceptable salt of the compound or a solvate thereof.

10. The compound according to 3, wherein R³ is represented by the formula (II):

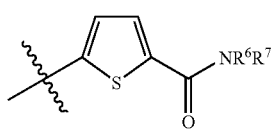

(wherein R⁶ is a hydrogen atom, and R⁷ is an isopropyl group, a methyl group, an ethyl group or a normal propyl group (the methyl group, the ethyl group and the normal propyl group are unsubstituted or substituted with one or more pyridyl groups, one or more pyridyl-N-oxide groups, one or more furyl groups, one or more pyrazinyl groups, one or more imidazolyl groups, one or more pyrazolyl groups or one or more isoxazolyl groups (the pyridyl groups, the pyridyl-N-oxide groups, the furyl groups, the pyrazinyl groups, the imidazolyl groups, the pyrazolyl groups and the isoxazolyl groups may be substituted with one or more methyl groups, one or more methoxy groups, one or more carboxyl groups or one or more halogen atoms))), a tautomer, prodrug or pharmaceutically acceptable salt of the compound or a solvate thereof.

11. The compound according to any one of 4 to 10, wherein R¹ is a 3,4-dimethyl-phenyl group, a tautomer, prodrug or pharmaceutically acceptable salt of the compound or a solvate thereof.

12. The compound according to any one of 4 to 10, wherein R¹ is a 3,4-dichloro-phenyl group, a tautomer, prodrug or pharmaceutically acceptable salt of the compound or a solvate thereof.

13. The compound according to any one of 4 to 10, wherein R¹ is a 4-chloro-phenyl group, a tautomer, prodrug or pharmaceutically acceptable salt of the compound or a solvate thereof.

14. The compound according to any one of 4 to 10, wherein R¹ is a 4-trifluoromethyl-phenyl group, a tautomer, prodrug or pharmaceutically acceptable salt of the compound or a solvate thereof.

15. The compound according to any one of 4 to 10, wherein R¹ is a 4-bromo-phenyl group, a tautomer, prodrug or pharmaceutically acceptable salt of the compound or a solvate thereof.

16. The compound according to any one of 4 to 10, wherein R¹ is a 4-trifluoromethoxy-phenyl group, a tautomer, prodrug or pharmaceutically acceptable salt of the compound or a solvate thereof.

17. A thrombopoietin receptor activator containing the compound according to any one of 1 to 16, a tautomer, prodrug or pharmaceutically acceptable salt of the compound or a solvate thereof, as an active ingredient.

18. A preventive, therapeutic or improving agent for diseases against which activation of the thrombopoietin receptor is effective, which contains the thrombopoietin receptor activator according to 17, as an active ingredient.

19. A platelet increasing agent containing the thrombopoietin receptor activator according to 17, as an active ingredient.

20. Medicament containing the compound according to any one of 1 to 16, a tautomer, prodrug or pharmaceutically acceptable salt of the compound or a solvate thereof, as an active ingredient.

Effects of the Invention

The thiophene compounds of the present invention have affinity for and agonistic action on the thrombopoietin receptor and show potent platelet increasing action through stimulation of differentiation and proliferation of megakaryocytic progenitor cells and megakaryocytes.

The thiophene compounds of the present invention are easily absorbable from the gastrointestinal tract and highly stimulate formation of megakaryocyte colonies. The orally absorbable thiophene compounds are retained in blood at high levels and therefore useful especially as oral medicines.

Though patent document 26 discloses compounds having platelet increasing action, it does not disclose the thiophene compounds of the present invention specifically enough to predict the especially excellent oral absorbability and the excellent megakaryocyte colony stimulating activity of the thiophene compounds of the present invention.

Therefore, the thiophene compounds of the present invention are useful as medicines and used as preventive, therapeutic and improving agents for diseases against which activation of the thrombopoietin receptor is effective, especially as platelet increasing agents.

BEST MODE FOR CARRYING OUT THE INVENTION

Now, the present invention will be described in detail.

In the present invention, "n" denotes normal, "i" denotes iso, "s" denotes secondary, "t" denotes tertiary, "c" denotes cyclo, "o" denotes ortho, "m" denotes meta, "p" denotes para, "Ph" denotes phenyl, "Py" denotes pyridyl, "Me" denotes methyl, "Et" denotes ethyl, "Pr" denotes propyl, and "Bu" denotes butyl.

First, the terms in the respective substituents $R^1$ to $R^{10}$ will be explained.

As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl and the like may be mentioned.

A $C_{1-6}$ alkyl group may be linear, branched or a $C_{3-6}$ cycloalkyl group, and in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-3}$ alkoxy group may include a linear, branched or $C_3$ cycloalkoxy group, and methoxy, ethoxy, n-propoxy, i-propoxy, c-propoxy and the like may be mentioned.

A $C_{2-14}$ aryl group may be a $C_{6-14}$ aryl group containing no hetero atoms as ring constituting atoms or a $C_{2-9}$ aromatic heterocyclic group, and a $C_{2-9}$ aromatic heterocyclic group may be a 5 to 7-membered $C_{2-6}$ heteromonocyclic group or a 8 to 10-membered $C_{5-9}$ fused heterobicyclic group containing from 1 to 3 oxygen atoms, nitrogen atoms or sulfur atoms singly or in combination.

As a $C_{6-14}$ aryl group containing no hetero atoms, a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

A 5 to 7-membered $C_{2-6}$ heteromonocyclic group may be a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group, a 3-4H-1,2,4-triazolyl group, a 3-1H-1,2,4-triazolyl group, a 5-1H-1,2,4-triazolyl group, a 4-2H-1,2,3-triazolyl group, a 5-2H-1,2,3-triazolyl group, a 4-1H-1,2,3-triazolyl group, a 5-1H-1,2,3-triazolyl group or the like.

A 8 to 10-membered $C_{5-9}$ fused heterocyclic group may be a 2-benzofuranyl group, 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pterdinyl group, a 4-pterdinyl group, a 6-pterdinyl group, a 7-pterdinyl group or the like.

A nitrogen-containing heterocyclyl group is a $C_{2-9}$ heteromonocyclic or fused heterobicyclic group which has one or more nitrogen atoms and may further contain one or more atoms optionally selected from oxygen atoms and sulfur atoms, and:

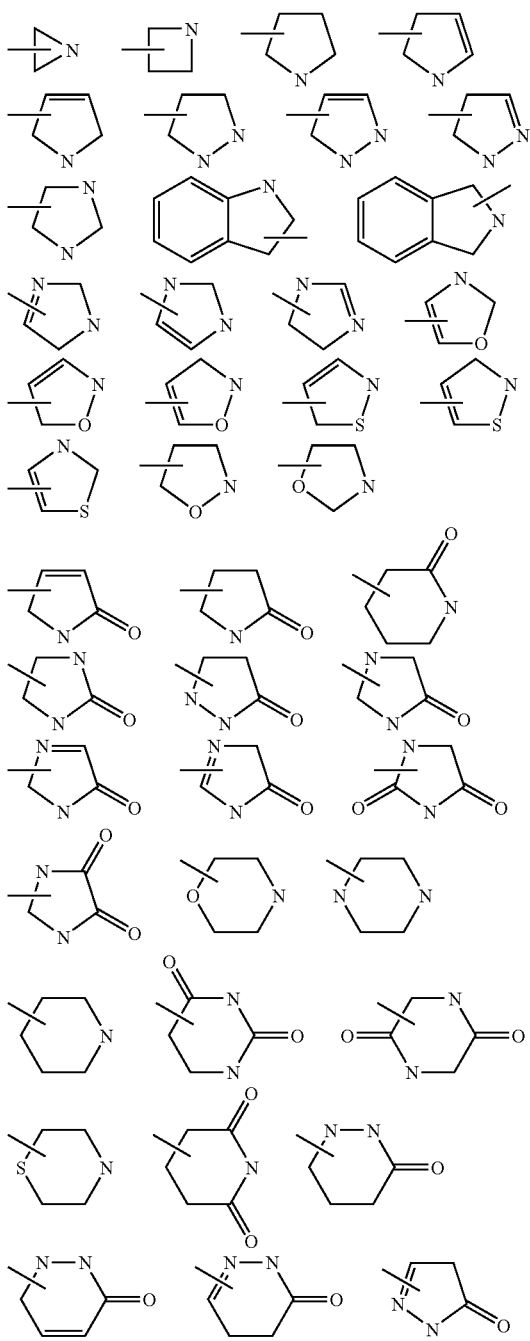
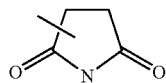

may be mentioned specifically.

Specific preferred examples of the substituent $R^1$ are phenyl groups substituted with one or more of the following substituents.

Substituents: a $C_{1-6}$ alkyl group, a $C_{1-3}$ alkyl group (the $C_{1-3}$ alkyl group is substituted with one or more halogen atoms), a $C_{1-3}$ alkoxy group (the $C_{1-3}$ alkoxy group is substituted with one or more halogen atoms) and a halogen atom.

Particularly preferred examples of the substituent $R^1$ are a 3,4-dimethyl-phenyl group, a 4-t-butyl-phenyl group, a 4-trifluoromethyl-phenyl group, a 3-chloro-phenyl group, a 4-chloro-phenyl group, a 4-fluoro-phenyl group, a 3,4-dichloro-phenyl group, a 4-bromo-phenyl group and a 4-trifluoromethoxy-phenyl group.

Specific preferred examples of the substituent $R^2$ are a hydrogen atom, a methyl group, an ethyl group, an i-propyl group, a n-propyl group and a trifluoromethyl group.

A particularly preferred example of the substituent $R^2$ is a methyl group.

Specific preferred examples of the substituent $R^3$ are a phenyl group, pyridyl groups (a 2-pyridyl group, a 3-pyridyl group and a 4-pyridyl group) and thienyl groups (a 2-thienyl group and a 3-thienyl group) substituted with one or more substituents selected from the following substituent set A and with one or more substituents selected from the following substituent set B.

Substituent set A: a hydrogen atom, a nitro group, a halogen atom, a $C_{1-3}$ alkyl group and a $C_{1-3}$ alkyl group substituted with one or more fluorine atoms.

Substituent set B: (C=O)$R^5$ (wherein $R^5$ is $NR^6R^7$ (wherein $R^6$ is a hydrogen atom or a $C_{1-3}$ alkyl group (the $C_{1-3}$ alkyl group may be substituted with one or more halogen atoms), and $R^7$ is a $C_{1-6}$ alkyl group (the $C_{1-6}$ alkyl group may be substituted with one or more halogen atoms, one or more hydroxyl groups, one or more $C_{1-3}$ alkoxy groups or one or more $C_{2-14}$ aryl groups (the $C_{2-14}$ aryl groups may be substituted with one or more $C_{1-3}$ alkyl groups, one or more $C_{1-3}$ alkoxy groups, one or more carboxyl groups, one or more carbamoyl groups, one or more cyano groups or one or more halogen atoms, and in the case of aryl groups containing one or more nitrogen atoms, may be N-oxides thereof)), a phenyl group, a thienyl group, a pyridyl group or a pyridyl-N-oxide group (the phenyl group, the thienyl group, the pyridyl group and the pyridyl-N-oxide group may be substituted with one or more halogen atoms), or $NR^6R^7$ is, as a whole, a nitrogen-containing heterocyclyl group (the nitrogen-containing heterocyclyl group may be substituted with one or more hydrogen atoms, one or more $C_{1-6}$ alkyl groups (the $C_{1-6}$ alkyl groups may be substituted with one or more halogen atoms), one or more halogen atoms, one or more hydroxyl groups or one or more $C_{1-3}$ alkoxy groups (the $C_{1-3}$ alkoxy groups may be substituted with one or more halogen atoms))) or a $C_{1-6}$ alkyl group (the $C_{1-6}$ alkyl group may be substituted with one or more halogen atoms, one or more pyridyl groups, one or more pyridyl-N-oxide groups, one or more furyl groups, one or more thienyl groups or one or more phenyl groups and is substituted with one or more cyano groups)).

A particularly preferred example of the substituent $R^3$ is represented by the formula (II):

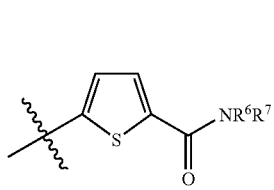

(II)

(wherein $R^6$ is a methyl group or an ethyl group, and $R^7$ is a $C_{1-6}$ alkyl group (the $C_{1-6}$ alkyl group may be substituted with one or more methoxy groups)).

Another particularly preferred example of the substituent $R^3$ is represented by the formula (II):

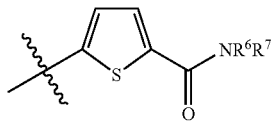

(II)

(wherein $R^6$ is a methyl group or an ethyl group, and $R^7$ is a $C_{1-3}$ alkyl group (the $C_{1-3}$ alkyl group is substituted with one or more phenyl groups or one or more pyridyl groups)).

Still another particularly preferred example of the substituent $R^3$ is represented by the formula (II):

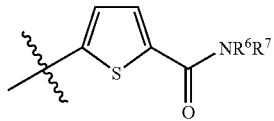

(II)

(wherein $R^6$ is a hydrogen atom, and $R^7$ is a $C_{1-6}$ alkyl group (the $C_{1-6}$ alkyl group is substituted with one or more methoxy groups) or a pyridyl group).

Still another particularly preferred example of the substituent $R^3$ is represented by the formula (IV):

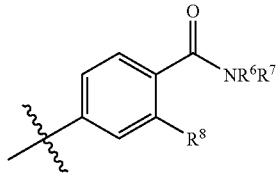

(IV)

(wherein $R^6$ is a hydrogen atom, $R^7$ is a $C_{1-3}$ alkyl group (the $C_{1-3}$ alkyl group may be substituted with one or more hydroxyl groups), and $R^8$ is a methyl group or a chlorine atom).

Still another particularly preferred example of the substituent $R^3$ is a group represented by the formula (II) or the formula (IV) wherein $NR^6R^7$ is, as a whole, represented by the formula (III):

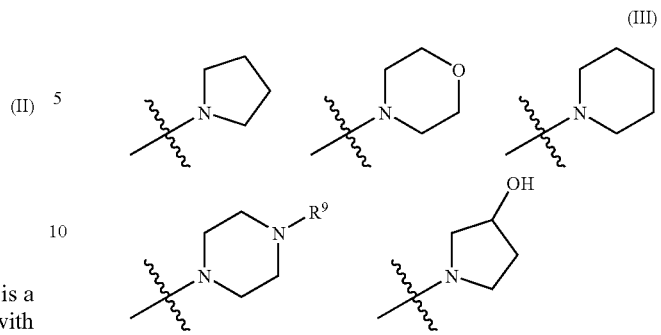

(III)

(wherein $R^9$ is a $C_{1-3}$ alkyl group).

Still another particularly preferred example of the substituent $R^3$ is represented by the formula (V):

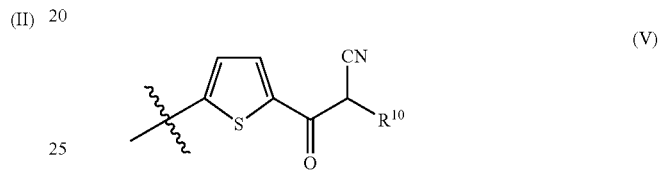

(V)

(wherein $R^{10}$ is a hydrogen atom or a $C_{1-3}$ alkyl group).

Still another particularly preferred example of the substituent $R^3$ is represented by the formula (II):

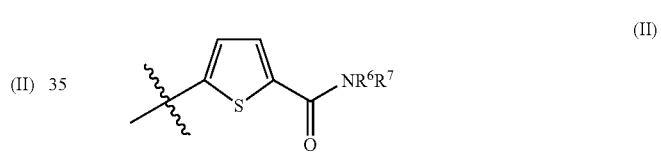

(II)

(wherein $R^6$ is a hydrogen atom, and $R^7$ is an isopropyl group, a methyl group, an ethyl group or a normal propyl group (the methyl group, the ethyl group and the normal propyl group are unsubstituted or substituted with one or more pyridyl groups, one or more pyridyl-N-oxide groups, one or more furyl groups, one or more pyrazinyl groups, one or more imidazolyl groups, one or more pyrazolyl groups or one or more isoxazolyl groups (the pyridyl groups, the pyridyl-N-oxide groups, the furyl groups, the pyrazinyl groups, the imidazolyl groups, the pyrazolyl groups and the isoxazolyl groups may be substituted with one or more methyl groups, one or more methoxy groups, one or more carboxyl groups or one or more halogen atoms))).

Specific preferred examples of the substituent $R^4$ are a hydrogen atom, a methyl group, an ethyl group, an i-propyl group, a n-propyl group and a trifluoromethyl group.

A particularly preferred example of the substituent $R^4$ is a hydrogen atom.

Favorable compounds for use in the thrombopoietin receptor activator, the preventive, therapeutic or improving agent for diseases against which activation of the thrombopoietin receptor is effective and the platelet increasing agent of the present invention are as follows.

1) Compounds represented by the formula (I) wherein $R^2$ is a methyl group, and $R^4$ is a hydrogen atom, tautomers, prodrugs or pharmaceutically acceptable salts of the compounds or solvates thereof.

2) The compounds according to 1), wherein $R^1$ is a 3,4-dimethyl-phenyl group, a 4-t-butyl-phenyl group, a 4-trifluoromethyl-phenyl group, a 3-chloro-phenyl group, a 4-chlorophenyl group, a 4-fluoro-phenyl group, a 3,4-dichloro-phenyl group, a 4-bromo-phenyl group or a 4-trifluoromethoxy-phenyl group, tautomers, prodrugs or pharmaceutically acceptable salts of the compounds or solvates thereof.

3) The compounds according to 2), wherein $R^3$ is represented by the formula (II):

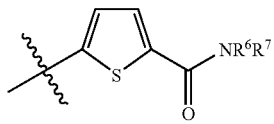

(II)

(wherein $R^6$ is a methyl group or an ethyl group, and $R^7$ is a $C_{1-6}$ alkyl group (the $C_{1-6}$ alkyl group may be substituted with one or more methoxy groups)), tautomers, prodrugs or pharmaceutically acceptable salts of the compounds or solvates thereof.

4) The compounds according to 2), wherein $R^3$ is represented by the formula (II):

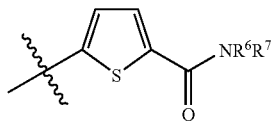

(II)

(wherein $R^6$ is a methyl group or an ethyl group, and $R^7$ is a $C_{1-3}$ alkyl group (the $C_{1-3}$ alkyl group is substituted with one or more phenyl groups or one or more pyridyl groups)), tautomers, prodrugs or pharmaceutically acceptable salts of the compounds or solvates thereof.

5) The compounds according to 2), wherein $R^3$ is represented by the formula (II):

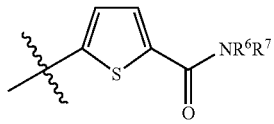

(II)

(wherein $R^6$ is a hydrogen atom, and $R^7$ is a $C_{1-6}$ alkyl group (the $C_{1-6}$ alkyl group is substituted with one or more methoxy groups) or a pyridyl group), tautomers, prodrugs or pharmaceutically acceptable salts of the compounds or solvates thereof.

6) The compounds according to 2), wherein $NR^6R^7$ in the formula (II) is, as a whole, represented by the formula (III):

(III)

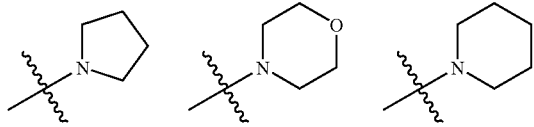

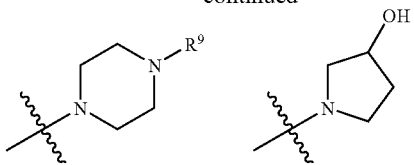

(wherein $R^9$ is a $C_{1-3}$ alkyl group), tautomers, prodrugs or pharmaceutically acceptable salts of the compounds or solvates thereof.

7) The compounds according to 2), wherein $R^3$ is represented by the formula (IV):

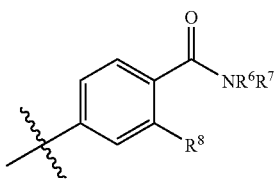

(IV)

(wherein $R^6$ is a hydrogen atom, $R^7$ is a $C_{1-3}$ alkyl group (the $C_{1-3}$ alkyl group may be substituted with one or more hydroxyl groups), and $R^8$ is a methyl group or a chlorine atom), tautomers, prodrugs or pharmaceutically acceptable salts of the compounds or solvates thereof.

8) The compounds according to 2), wherein $R^3$ is represented by the formula (V):

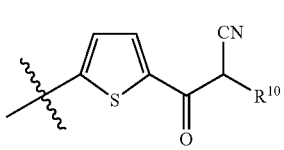

(V)

(wherein $R^{10}$ is a hydrogen atom or a $C_{1-3}$ alkyl group), tautomers, prodrugs or pharmaceutically acceptable salts is of the compounds or solvates thereof.

9) The compounds according to 2), wherein $R^3$ is represented by the formula (II):

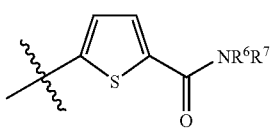

(II)

(wherein $R^6$ is a hydrogen atom, and $R^7$ is an isopropyl group, a methyl group, an ethyl group or a normal propyl group (the methyl group, the ethyl group and the normal propyl group are unsubstituted or substituted with one or more pyridyl groups, one or more pyridyl-N-oxide groups, one or more furyl groups, one or more pyrazinyl groups, one or more imidazolyl groups, one or more pyrazolyl groups or one or more isoxazolyl groups (the pyridyl groups, the pyridyl-N-oxide groups, the furyl groups, the pyrazinyl groups, the imidazolyl groups, the pyrazolyl groups and the isoxazolyl groups may be substituted with one or more methyl groups, one or more methoxy groups, one or more carboxyl groups or one or more halogen atoms))), tautomers, prodrugs or pharmaceutically acceptable salts of the compounds or solvates thereof.

10) The compounds according to any one of 3) to 9), wherein $R^1$ is a 3,4-dimethyl-phenyl group, tautomers, prodrugs or pharmaceutically acceptable salts of the compounds or solvates thereof.

11) The compounds according to any one of 3) to 9), wherein $R^1$ is a 3,4-dichloro-phenyl group, tautomers, prodrugs or pharmaceutically acceptable salts of the compounds or solvates thereof.

12) The compounds according to any one of 3) to 9), wherein $R^1$ is a 4-chloro-phenyl group, tautomers, prodrugs or pharmaceutically acceptable salts of the compounds or solvates thereof.

13) The compounds according to any one of 3) to 9), wherein $R^1$ is a 4-trifluoromethyl-phenyl group, tautomers, prodrugs or pharmaceutically acceptable salts of the compounds or solvates thereof.

14) The compounds according to any one of 3) to 9), wherein $R^1$ is a 4-bromo-phenyl group, tautomers, prodrugs or pharmaceutically acceptable salts of the compounds or solvates thereof.

15) The compounds according to any one of 3) to 9), wherein $R^1$ is a 4-trifluoromethoxy-phenyl group, tautomers, prodrugs or pharmaceutically acceptable salts of the compounds or solvates thereof.

16) The compounds wherein $R^4$ is a hydrogen atom, and $R^1$, $R^2$ and $R^3$ are any of the following combinations in Table 1, tautomers, prodrugs or pharmaceutically acceptable salts of the compounds or solvates thereof.

The symbols in Table 1 denote the following substituents.

TABLE 1

| $R^1$ | $R^2$ | $R^3$ | $R^1$ | $R^2$ | $R^3$ |
|---|---|---|---|---|---|
| Q1a | Me | Q3a | Q1e | Me | Q3a |
| Q1a | Me | Q3b | Q1e | Me | Q3b |
| Q1a | Me | Q3c | Q1e | Me | Q3c |
| Q1a | Me | Q3d | Q1e | Me | Q3d |
| Q1a | Me | Q3e | Q1e | Me | Q3e |
| Q1a | Me | Q3f | Q1e | Me | Q3f |
| Q1a | Me | Q3g | Q1e | Me | Q3g |
| Q1a | Me | Q3h | Q1e | Me | Q3h |
| Q1a | Me | Q3i | Q1e | Me | Q3i |
| Q1a | Me | Q3j | Q1e | Me | Q3j |
| Q1a | Me | Q3k | Q1e | Me | Q3k |
| Q1a | Me | Q3l | Q1e | Me | Q3l |
| Q1b | Me | Q3a | Q1f | Me | Q3a |
| Q1b | Me | Q3b | Q1f | Me | Q3b |
| Q1b | Me | Q3c | Q1f | Me | Q3c |
| Q1b | Me | Q3d | Q1f | Me | Q3d |
| Q1b | Me | Q3e | Q1f | Me | Q3e |
| Q1b | Me | Q3f | Q1f | Me | Q3f |
| Q1b | Me | Q3g | Q1f | Me | Q3g |
| Q1b | Me | Q3h | Q1f | Me | Q3h |
| Q1b | Me | Q3i | Q1f | Me | Q3i |
| Q1b | Me | Q3j | Q1f | Me | Q3j |
| Q1b | Me | Q3k | Q1f | Me | Q3k |
| Q1b | Me | Q3l | Q1f | Me | Q3l |
| Q1c | Me | Q3a | Q1g | Me | Q3a |
| Q1c | Me | Q3b | Q1g | Me | Q3b |
| Q1c | Me | Q3c | Q1g | Me | Q3c |
| Q1c | Me | Q3d | Q1g | Me | Q3d |
| Q1c | Me | Q3e | Q1g | Me | Q3e |
| Q1c | Me | Q3f | Q1g | Me | Q3f |
| Q1c | Me | Q3g | Q1g | Me | Q3g |
| Q1c | Me | Q3h | Q1g | Me | Q3h |
| Q1c | Me | Q3i | Q1g | Me | Q3i |
| Q1c | Me | Q3j | Q1g | Me | Q3j |
| Q1c | Me | Q3k | Q1g | Me | Q3k |
| Q1c | Me | Q3l | Q1g | Me | Q3l |
| Q1d | Me | Q3a | Q1h | Me | Q3a |
| Q1d | Me | Q3b | Q1h | Me | Q3b |
| Q1d | Me | Q3c | Q1h | Me | Q3c |
| Q1d | Me | Q3d | Q1h | Me | Q3d |
| Q1d | Me | Q3e | Q1h | Me | Q3e |
| Q1d | Me | Q3f | Q1h | Me | Q3f |
| Q1d | Me | Q3g | Q1h | Me | Q3g |
| Q1d | Me | Q3h | Q1h | Me | Q3h |
| Q1d | Me | Q3i | Q1h | Me | Q3i |
| Q1d | Me | Q3j | Q1h | Me | Q3j |
| Q1d | Me | Q3k | Q1h | Me | Q3k |
| Q1d | Me | Q3l | Q1h | Me | Q3l |

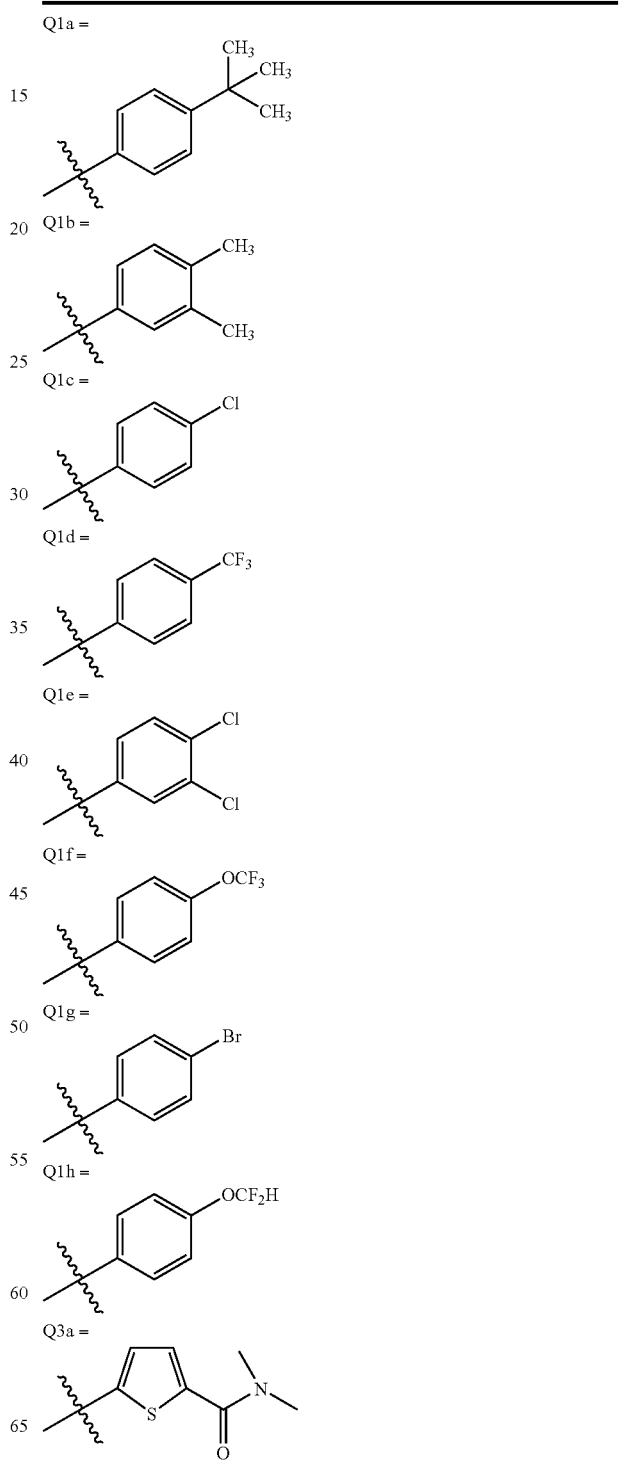

TABLE 1-continued

Q3b =
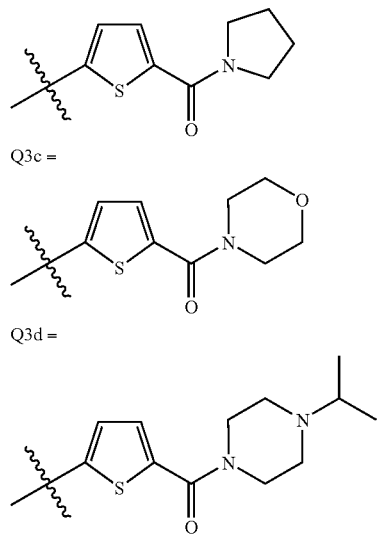

Q3c =

Q3d =

Q3e =

Q3f =
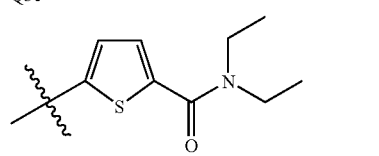

Q3g =
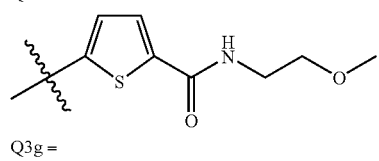

Q3h =
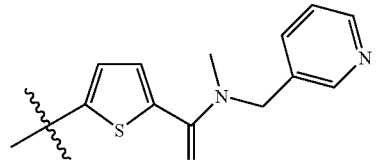

Q3i =
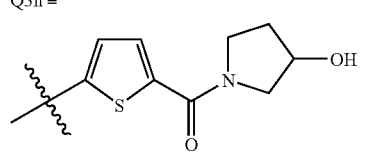

Q3j =
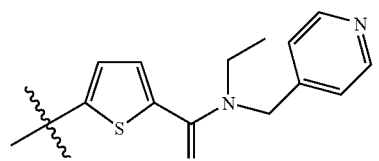

TABLE 1-continued

Q3k =
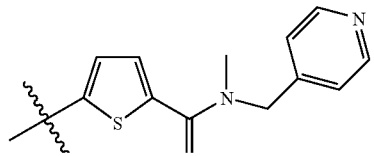

Q3l =
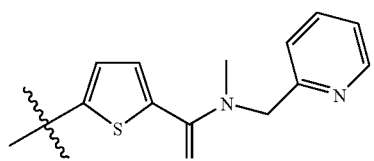

17) The compounds wherein $R^4$ is a hydrogen atom, and $R^1$, $R^2$ and $R^3$ are any of the following combinations in Table 1, tautomers, prodrugs or pharmaceutically acceptable salts of the compounds or solvates thereof (provided that in the case of 17), Q1a, Q1b, Q1c, Q1d, Q1e, Q1f, Q1g, Q1h, Q3a, Q3b, Q3c, Q3d, Q3e, Q3f, Q3g, Q3h, Q3i, Q3j, Q3k and Q3l in the table denote the following substituents).

Q1a =
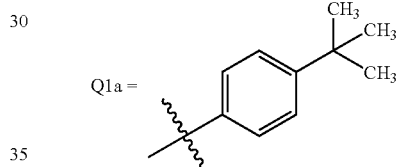

Q1b =
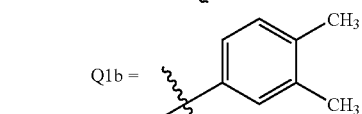

Q1c =
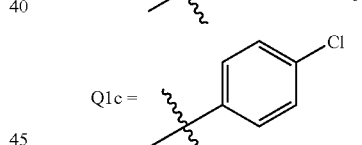

Q1d =
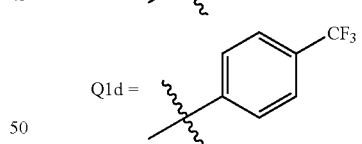

Q1e =
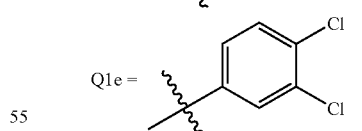

Q1f =
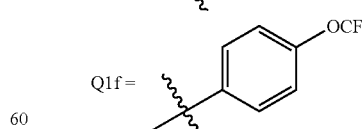

Q1g =
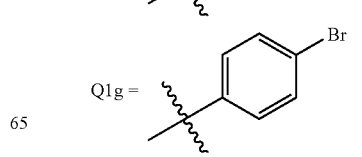

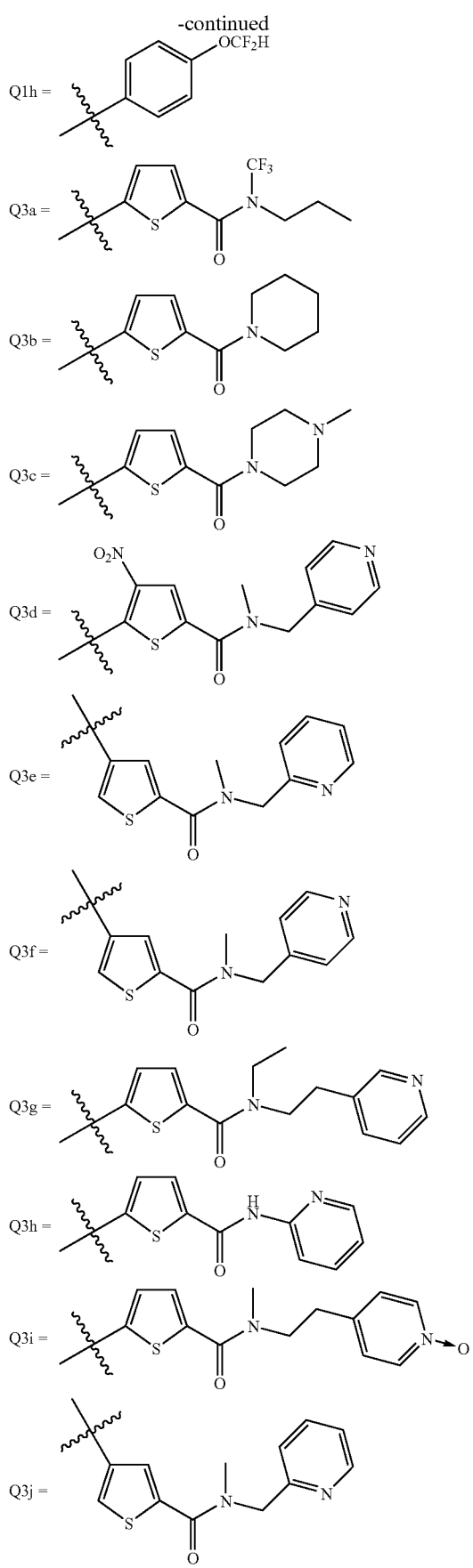
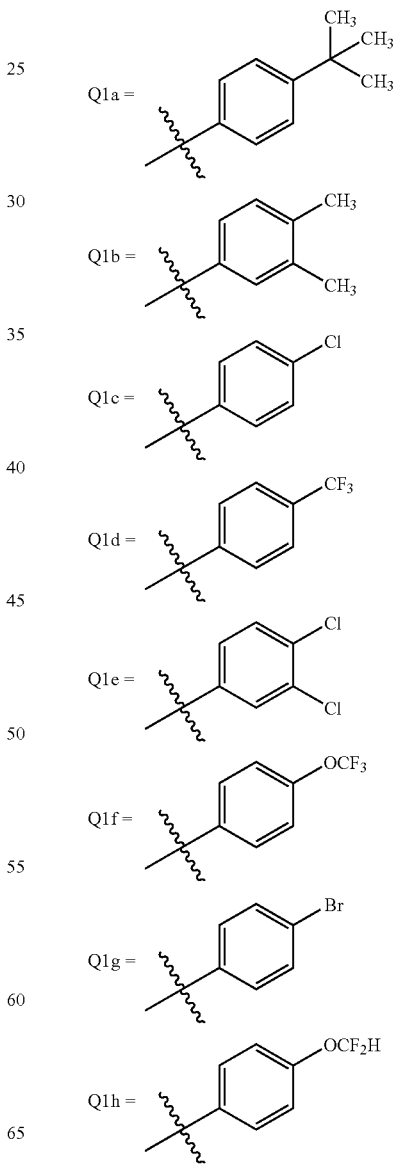
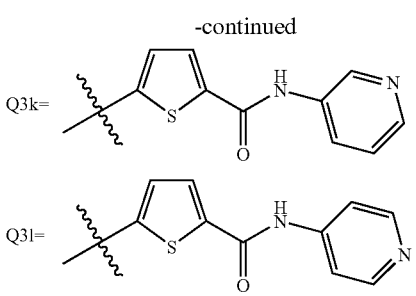
18) The compounds wherein $R^4$ is a hydrogen atom, and $R^1$, $R^2$ and $R^3$ are any of the following combinations in Table 1, tautomers, prodrugs or pharmaceutically acceptable salts of the compounds or solvates thereof (provided that in the case of 18), Q1a, Q1b, Q1c, Q1d, Q1e, Q1f, Q1g, Q1h, Q3a, Q3b, Q3c, Q3d, Q3e, Q3f, Q3g, Q3h, Q3i, Q3j, Q3k and Q3l in the table denote the following substituents).

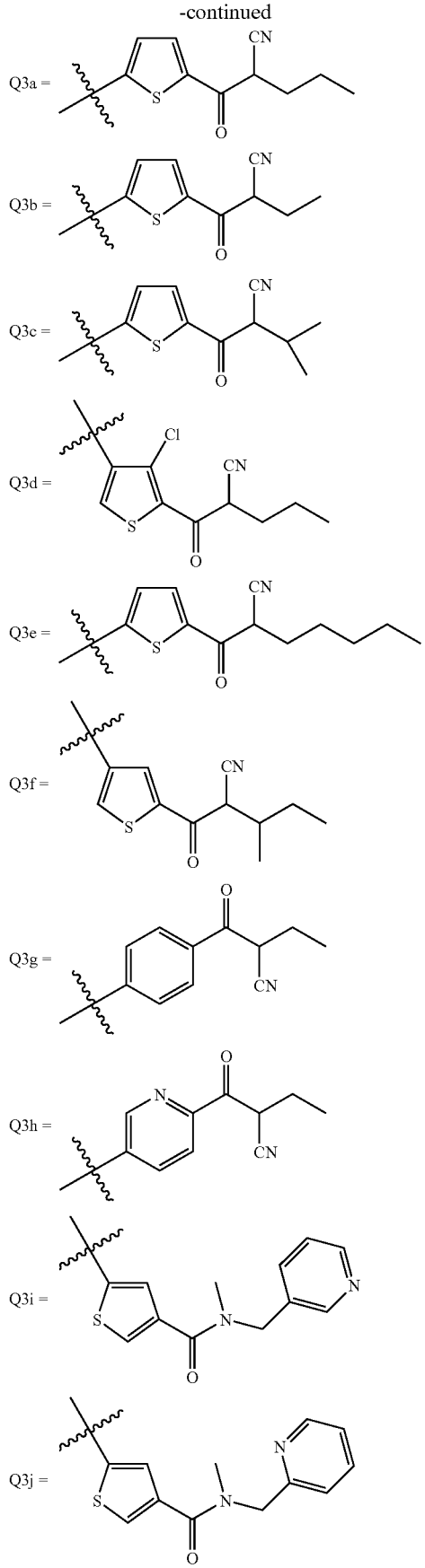

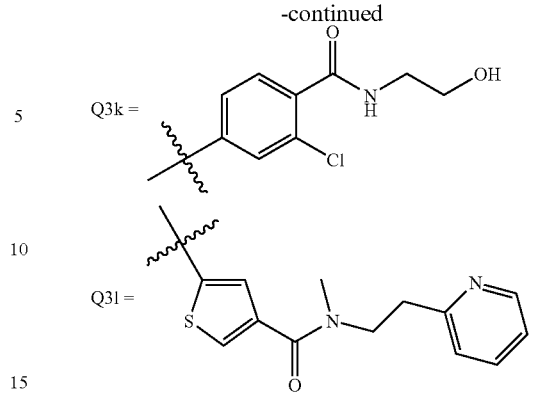

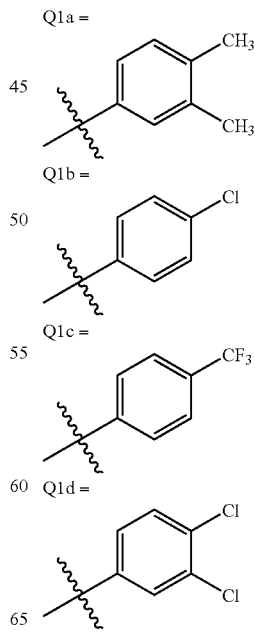

19) The compounds wherein $R^4$ is a hydrogen atom, and $R^1$, $R^2$ and $R^3$ are any of the following combinations in Table 2, tautomers, prodrugs or pharmaceutically acceptable salts of the compounds or solvates thereof.

The symbols in Table 2 denote the following substituents.

TABLE 2

| $R^1$ | $R^2$ | $R^3$ | $R^1$ | $R^2$ | $R^3$ |
|---|---|---|---|---|---|
| Q1a | Me | Q3a | Q1d | Me | Q3a |
| Q1a | Me | Q3b | Q1d | Me | Q3b |
| Q1a | Me | Q3c | Q1d | Me | Q3c |
| Q1a | Me | Q3d | Q1d | Me | Q3d |
| Q1a | Me | Q3e | Q1d | Me | Q3e |
| Q1a | Me | Q3f | Q1d | Me | Q3f |
| Q1b | Me | Q3a | Q1e | Me | Q3a |
| Q1b | Me | Q3b | Q1e | Me | Q3b |
| Q1b | Me | Q3c | Q1e | Me | Q3c |
| Q1b | Me | Q3d | Q1e | Me | Q3d |
| Q1b | Me | Q3e | Q1e | Me | Q3e |
| Q1b | Me | Q3f | Q1e | Me | Q3f |
| Q1c | Me | Q3a | Q1f | Me | Q3a |
| Q1c | Me | Q3b | Q1f | Me | Q3b |
| Q1c | Me | Q3c | Q1f | Me | Q3c |
| Q1c | Me | Q3d | Q1f | Me | Q3d |
| Q1c | Me | Q3e | Q1f | Me | Q3e |
| Q1c | Me | Q3f | Q1f | Me | Q3f |

TABLE 2-continued

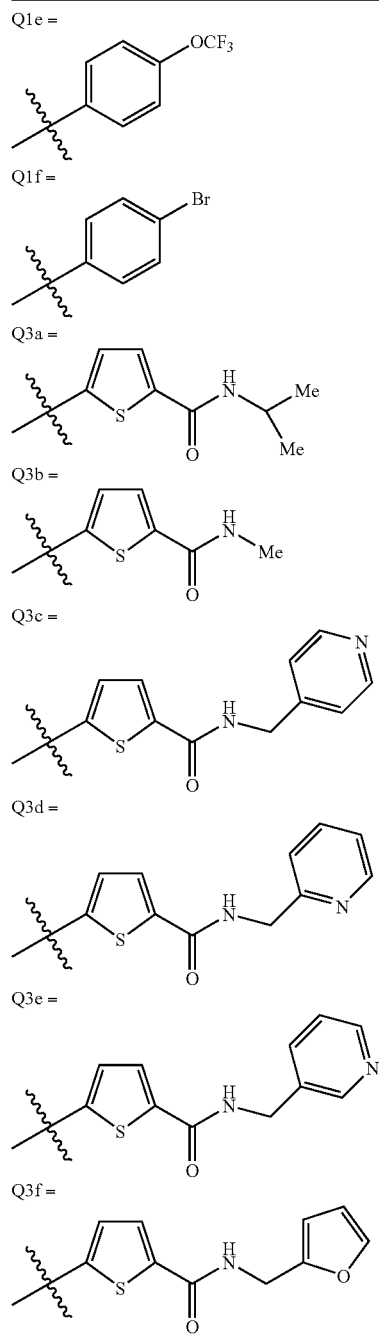

20) The compounds wherein $R^4$ is a hydrogen atom, and $R^1$, $R^2$ and $R^3$ are any of the following combinations in Table 3, tautomers, prodrugs or pharmaceutically acceptable salts of the compounds or solvates thereof.

The symbols in Table 3 denote the following substituents.

TABLE 3

| $R^1$ | $R^2$ | $R^3$ | $R^1$ | $R^2$ | $R^3$ |
|---|---|---|---|---|---|
| Q1a | Me | Q3a | Q1d | Me | Q3a |
| Q1a | Me | Q3b | Q1d | Me | Q3b |
| Q1a | Me | Q3c | Q1d | Me | Q3c |
| Q1a | Me | Q3d | Q1d | Me | Q3d |
| Q1a | Me | Q3e | Q1d | Me | Q3e |
| Q1a | Me | Q3f | Q1d | Me | Q3f |
| Q1b | Me | Q3a | Q1e | Me | Q3a |
| Q1b | Me | Q3b | Q1e | Me | Q3b |
| Q1b | Me | Q3c | Q1e | Me | Q3c |
| Q1b | Me | Q3d | Q1e | Me | Q3d |
| Q1b | Me | Q3e | Q1e | Me | Q3e |
| Q1b | Me | Q3f | Q1e | Me | Q3f |
| Q1c | Me | Q3a | Q1f | Me | Q3a |
| Q1c | Me | Q3b | Q1f | Me | Q3b |
| Q1c | Me | Q3c | Q1f | Me | Q3c |
| Q1c | Me | Q3d | Q1f | Me | Q3d |
| Q1c | Me | Q3e | Q1f | Me | Q3e |
| Q1c | Me | Q3f | Q1f | Me | Q3f |

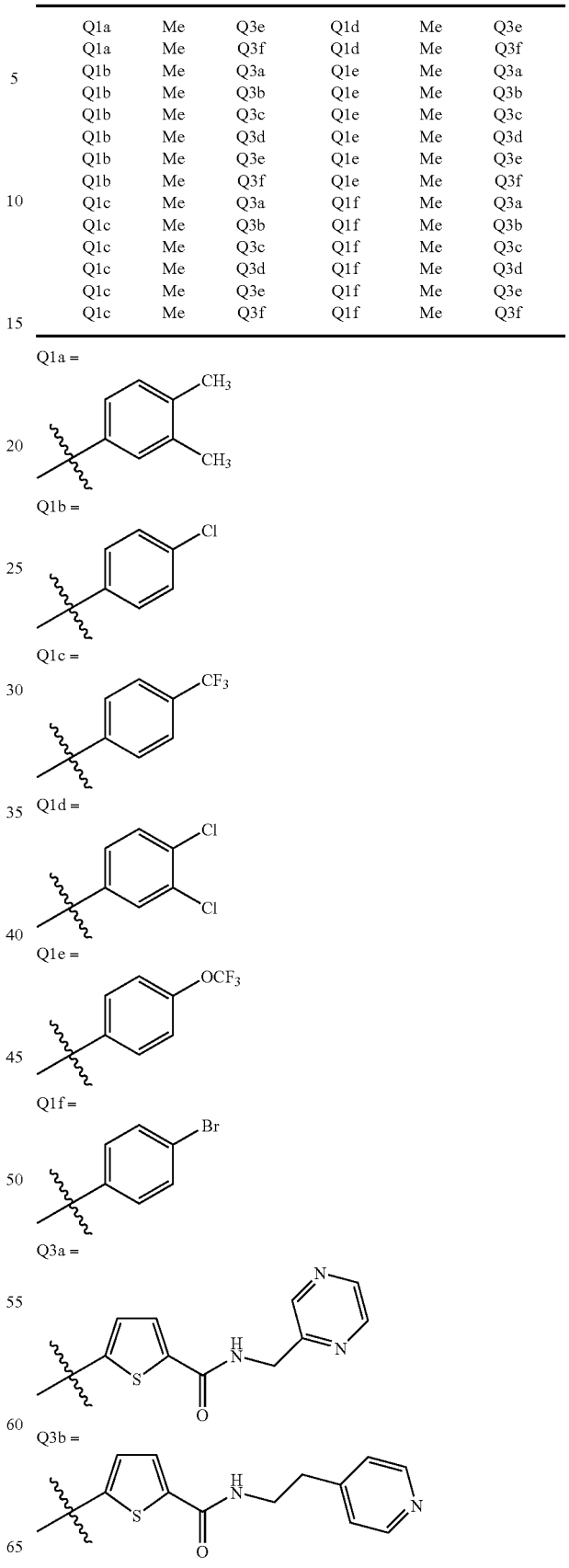

TABLE 3-continued

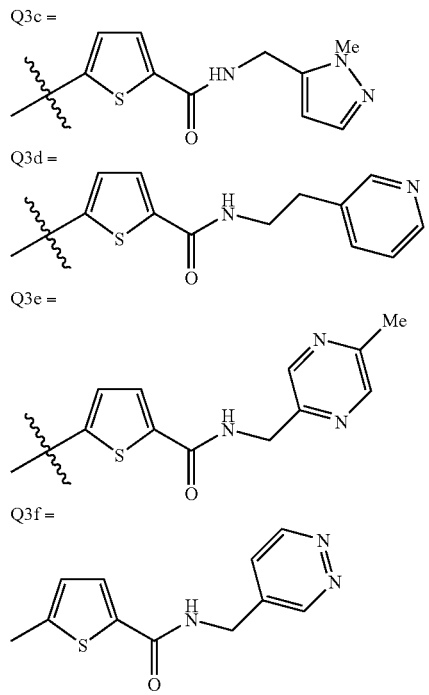

21) The compounds wherein $R^4$ is a hydrogen atom, and $R^1$, $R^2$ and $R^3$ are any of the following combinations in Table 4, tautomers, prodrugs or pharmaceutically acceptable salts of the compounds or solvates thereof.

The symbols in Table 4 denote the following substituents.

TABLE 4

| $R^1$ | $R^2$ | $R^3$ | $R^1$ | $R^2$ | $R^3$ |
|-------|-------|-------|-------|-------|-------|
| Q1a | Me | Q3a | Q1d | Me | Q3a |
| Q1a | Me | Q3b | Q1d | Me | Q3b |
| Q1a | Me | Q3c | Q1d | Me | Q3c |
| Q1a | Me | Q3d | Q1d | Me | Q3d |
| Q1a | Me | Q3e | Q1d | Me | Q3e |
| Q1a | Me | Q3f | Q1d | Me | Q3f |
| Q1b | Me | Q3a | Q1e | Me | Q3a |
| Q1b | Me | Q3b | Q1e | Me | Q3b |
| Q1b | Me | Q3c | Q1e | Me | Q3c |
| Q1b | Me | Q3d | Q1e | Me | Q3d |
| Q1b | Me | Q3e | Q1e | Me | Q3e |
| Q1b | Me | Q3f | Q1e | Me | Q3f |
| Q1c | Me | Q3a | Q1f | Me | Q3a |
| Q1c | Me | Q3b | Q1f | Me | Q3b |
| Q1c | Me | Q3c | Q1f | Me | Q3c |
| Q1c | Me | Q3d | Q1f | Me | Q3d |
| Q1c | Me | Q3e | Q1f | Me | Q3e |
| Q1c | Me | Q3f | Q1f | Me | Q3f |

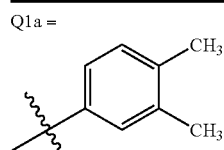

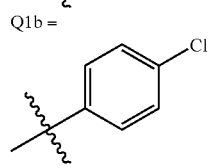

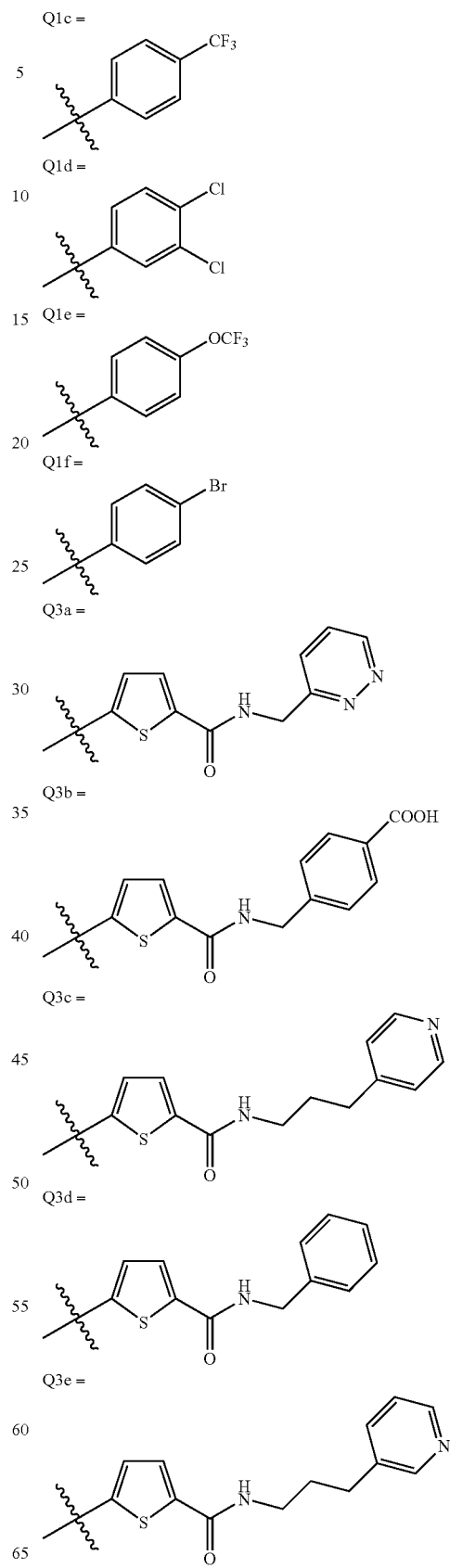

TABLE 4-continued

Q3f =

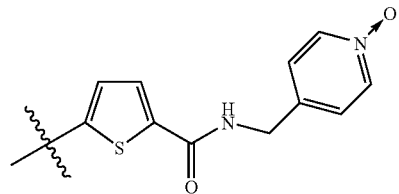

22) The compounds wherein $R^4$ is a hydrogen atom, and $R^1$, $R^2$ and $R^3$ are any of the following combinations in Table 5, tautomers, prodrugs or pharmaceutically acceptable salts of the compounds or solvates thereof.

The symbols in Table 5 denote the following substituents.

TABLE 5

| $R^1$ | $R^2$ | $R^3$ | $R^1$ | $R^2$ | $R^3$ |
|---|---|---|---|---|---|
| Q1a | Me | Q3a | Q1d | Me | Q3a |
| Q1a | Me | Q3b | Q1d | Me | Q3b |
| Q1a | Me | Q3c | Q1d | Me | Q3c |
| Q1a | Me | Q3d | Q1d | Me | Q3d |
| Q1a | Me | Q3e | Q1d | Me | Q3e |
| Q1a | Me | Q3f | Q1d | Me | Q3f |
| Q1b | Me | Q3a | Q1e | Me | Q3a |
| Q1b | Me | Q3b | Q1e | Me | Q3b |
| Q1b | Me | Q3c | Q1e | Me | Q3c |
| Q1b | Me | Q3d | Q1e | Me | Q3d |
| Q1b | Me | Q3e | Q1e | Me | Q3e |
| Q1b | Me | Q3f | Q1e | Me | Q3f |
| Q1c | Me | Q3a | Q1f | Me | Q3a |
| Q1c | Me | Q3b | Q1f | Me | Q3b |
| Q1c | Me | Q3c | Q1f | Me | Q3c |
| Q1c | Me | Q3d | Q1f | Me | Q3d |
| Q1c | Me | Q3e | Q1f | Me | Q3e |
| Q1c | Me | Q3f | Q1f | Me | Q3f |

Q1a =

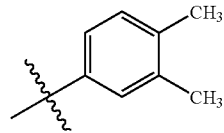

Q1b =

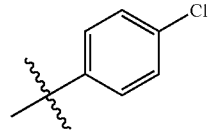

Q1c =

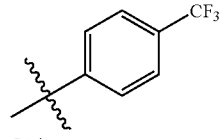

Q1d =

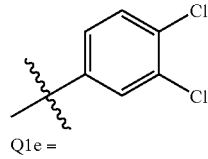

Q1e =

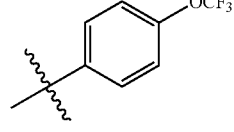

Q1f =

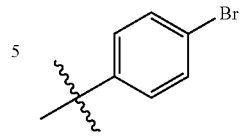

Q3a =

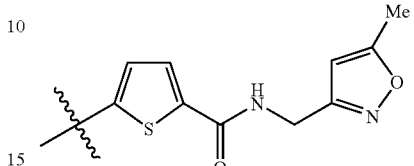

Q3b =

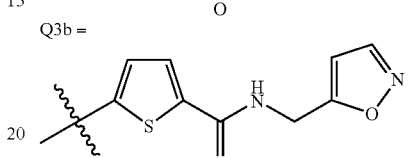

Q3c =

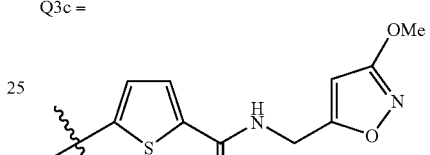

Q3d =

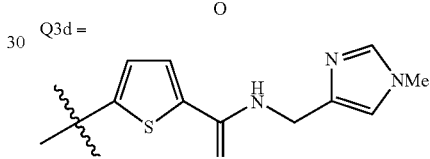

Q3e =

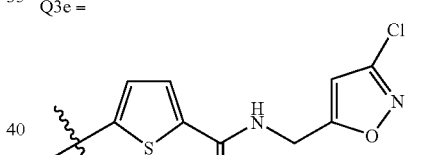

Q3f =

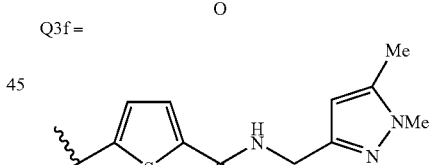

23) The compounds wherein $R^4$ is a hydrogen atom, and $R^1$, $R^2$ and $R^3$ are any of the following combinations in Table 6, tautomers, prodrugs or pharmaceutically acceptable salts of the compounds or solvates thereof.

The symbols in Table 6 denote the following substituents.

TABLE 6

| $R^1$ | $R^2$ | $R^3$ | $R^1$ | $R^2$ | $R^3$ |
|---|---|---|---|---|---|
| Q1a | Me | Q3a | Q1d | Me | Q3a |
| Q1a | Me | Q3b | Q1d | Me | Q3b |
| Q1a | Me | Q3c | Q1d | Me | Q3c |
| Q1a | Me | Q3d | Q1d | Me | Q3d |
| Q1a | Me | Q3e | Q1d | Me | Q3e |
| Q1a | Me | Q3f | Q1d | Me | Q3f |
| Q1b | Me | Q3a | Q1e | Me | Q3a |

TABLE 6-continued

| Q1b | Me | Q3b | Q1e | Me | Q3b |
| Q1b | Me | Q3c | Q1e | Me | Q3c |
| Q1b | Me | Q3d | Q1e | Me | Q3d |
| Q1b | Me | Q3e | Q1e | Me | Q3e |
| Q1b | Me | Q3f | Q1e | Me | Q3f |
| Q1c | Me | Q3a | Q1f | Me | Q3a |
| Q1c | Me | Q3b | Q1f | Me | Q3b |
| Q1c | Me | Q3c | Q1f | Me | Q3c |
| Q1c | Me | Q3d | Q1f | Me | Q3d |
| Q1c | Me | Q3e | Q1f | Me | Q3e |
| Q1c | Me | Q3f | Q1f | Me | Q3f |

Q1a = 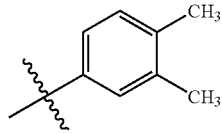

Q1b = 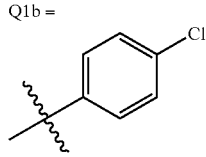

Q1c = 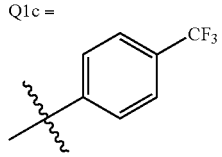

Q1d = 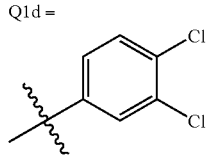

Q1e = 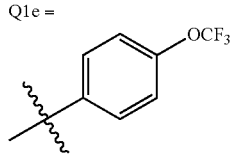

Q1f = 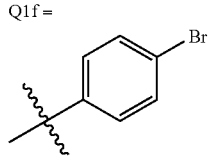

Q3a = 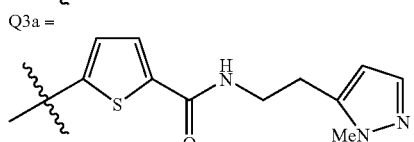

Q3b = 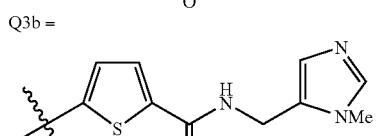

Q3c = 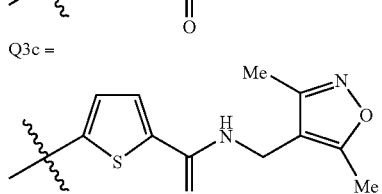

Q3d =

Q3e =

Q3f =

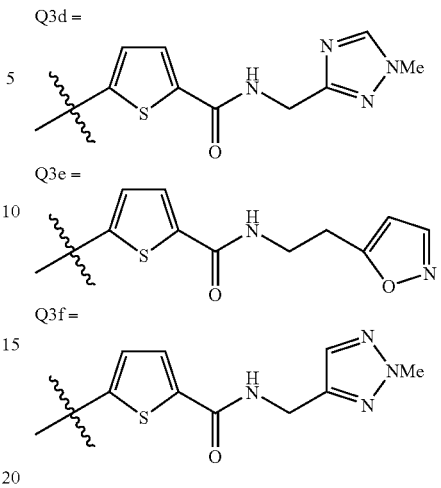

24) The compounds according to 16) to 23), wherein $R^2$ is converted to a hydrogen atom, tautomers, prodrugs or pharmaceutically acceptable salts of the compounds or solvates thereof.

25) The compounds according to 16) to 23), wherein $R^2$ is converted to a trifluoromethyl group, tautomers, prodrugs or pharmaceutically acceptable salts of the compounds or solvates thereof.

26) The compounds according to 16) to 23), wherein $R^2$ is converted to an ethyl group, tautomers, prodrugs or pharmaceutically acceptable salts of the compounds or solvates thereof.

27) The compounds according to 16) to 23), wherein $R^2$ is converted to a n-propyl group, tautomers, prodrugs or pharmaceutically acceptable salts of the compounds or solvates thereof.

28) The compounds according to 16) to 23), wherein $R^2$ is converted to an i-propyl, tautomers, prodrugs or pharmaceutically acceptable salts of the compounds or solvates thereof.

29) The compounds according to 16) to 28), wherein $R^4$ is converted to a methyl group, tautomers, prodrugs or pharmaceutically acceptable salts of the compounds or solvates thereof.

30) The compounds according to 16) to 28), wherein $R^4$ is converted to a trifluoromethyl group, tautomers, prodrugs or pharmaceutically acceptable salts of the compounds or solvates thereof.

31) The compounds according to 16) to 28), wherein $R^4$ is converted to an ethyl group, tautomers, prodrugs or pharmaceutically acceptable salts of the compounds or solvates thereof.

32) Thrombopoietin receptor activators containing the compounds according to 1) to 31), tautomers, prodrugs or pharmaceutically acceptable salts of the compounds or solvates thereof, as an active ingredient.

33) Preventive, therapeutic and improving agents for diseases against which activation of the thrombopoietin receptor is effective, which contain the thrombopoietin receptor activators according to 32), as an active ingredient.

34) Platelet increasing agents containing the thrombopoietin receptor activators according to 32), as an active ingredient.

35) Medicaments containing any of the compounds according to 1) to 31) or the compounds represented by the formula (I), tautomers, prodrugs or pharmaceutically acceptable salts of the activators or solvates thereof, as an active ingredient.

In the present invention, the compounds of the present invention represented by the formula (1) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios.

The compounds of the present invention represented by the formula (1) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds of the present invention represented by the formula (1) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, tartaric acid, benzenesulfonic acid and p-toluenesulfonic acid).

The compounds which serve as prodrugs are derivatives of the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrugs (Elsevier, Amsterdam 1985). In the present invention, when the compound has a hydroxyl group, acyloxy derivatives obtained by reacting the compound with appropriate acyl halides or appropriate acid anhydrides may, for example, be mentioned as prodrugs. Acyloxys particularly preferred as prodrugs include —$OCOC_2H_5$, —$OCO(t$-$Bu)$, —$OCOC_{15}H_{31}$, —$OCO(m$-$CO_2Na$-$Ph)$, —$OCOCH_2CH_2CO_2Na$, —$OCOCH(NH_2)CH_3$, —$OCOCH_2N(CH_3)_2$ and the like. When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —$NHCO(CH_2)_{20}OCH_3$, —$NHCOCH(NH_2)CH_3$ and the like. When the compound of the present invention has a carboxyl group, carboxylic acid esters with aliphatic alcohols or carboxylic acid esters obtained by the reaction with an alcoholic free hydroxyl group of 1,2- or 1,3-diglycerides may, for example, be mentioned as prodrugs. Particularly preferred prodrugs are methyl esters and ethyl esters.

The preventive, therapeutic and improving agents for diseases against which activation of the thrombopoietin receptor is effective or platelet increasing agents which contain the thrombopoietin receptor activators of the present invention as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral drugs or rectal administration for adults and about from 0.05 mg to 500 mg/human/day in the case of injections for adults, though it depends on the age and conditions of the patient. The above-mentioned ranges are mere examples, and the dose should be determined from the conditions of the patient.

The present invention is used when the use of compounds which have thrombopoietin receptor affinity and act as thrombopoietin receptor agonists are expected to improve pathological conditions. For example, hematological disorders accompanied by abnormal platelet count may be mentioned. Specifically, it is effective for therapy or prevention of human and mammalian diseases caused by abnormal megakaryopoiesis, especially those accompanied by thrombocytopenia. Examples of such diseases include thrombocytopenia accompanying chemotherapy or radiotherapy of cancer, thrombocytopenia accompanying antiviral therapy for diseases such as hepatitis C, thrombocytopenia caused by bone marrow transplantation, surgery and serious infections, or gastrointestinal bleeding, but such diseases are not restricted to those mentioned. Typical thrombocytopenias such as aplastic anemia, idiopathic thrombocytopenic purpura, myelodysplastic syndrome, hepatic disease, HIV infection and thrombopoietin deficiency are also targets of the agents of the present invention. The present invention may be used as a peripheral stem cell mobilizer, a megakaryblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

The compounds represented by the formula (I) are prepared, for example, by the process represented by the formula (1) illustrated below.

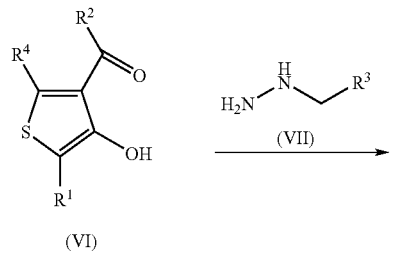

(1)

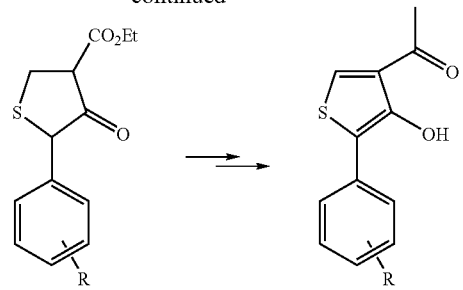

(Et = C₂H₅)

For synthesis of the —NH₂ compounds (VII), for example, the methods disclosed in Synthetic Commun., 28(7), 1223-1231 (1998), J. Chem. Soc., 1225 (1948) and J. Chem. Soc., 2831 (1952) may be referred to.

The compounds represented by the formula (I) can also be obtained by the process represented by the formula (3) illustrated below.

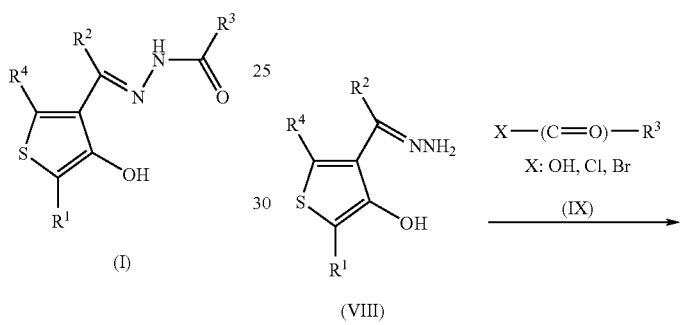

(3)

X: OH, Cl, Br

The reaction of the compound (IV) with a —NH₂ compound (VII) in a solvent, if necessary in the presence of a catalyst, under heating with stirring gives a desired compound or its precursor. The precursor may be, if necessary, hydrolyzed, deprotected, reduced or oxidized to a desired compound. The compounds of the present invention usually can be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

For the syntheses of the intermediates (VI), the following method disclosed in JP-A-48-026755 may, for example, be referred to.

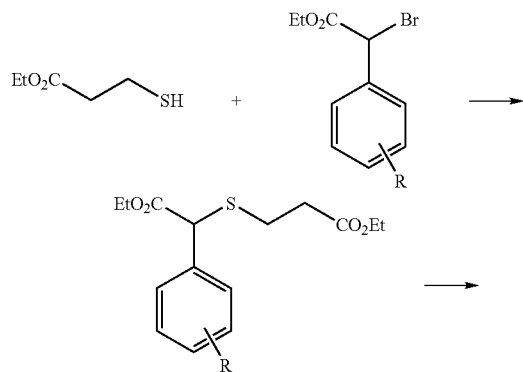

The reaction of the compound (VIII) with the compound (IX) in a solvent, if necessary, in the presence of a catalyst, a dehydrating condensation agent or a base, under heating with stirring gives a desired compound or its precursor. The precursor may be, if necessary, hydrolyzed, deprotected, reduced or oxidized to a desired compound. The compounds of the present invention usually can be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

The compound (VIII) can be obtained by stirring the compound (VI) with hydrazine or its derivative in a solvent, if necessary in the presence of a catalyst, under heating.

EXAMPLES

Now, the present invention will be described in further detail with reference to Reference Synthetic Examples, Synthetic Examples, Assay Examples and Formulation Examples. However, it should be understood that the present invention is by no means restricted by these specific Examples.

The $^1$H-NMR analysis was carried out at 300 MHz, and LC/MS was measured under the following conditions.

LC/MS Condition 1
  Column: Waters SunFire C18 (3.5 μm, 4.6×30 mm)
  Eluent: acetonitrile/0.1% aqueous formic acid (10/90→30/70)

LC/MS Condition 2
  Column: Waters SunFire C18 (3.5 μm, 4.6×30 mm)
  Eluent: acetonitrile/0.1% aqueous formic acid (10/90→60/40)

LC/MS Conditions 3
  Column: Waters SunFire C18 (3.5 μm, 4.6×30 mm)
  Eluent: acetonitrile/0.1% aqueous formic acid (10/90→85/15)

LC/MS Conditions 4
  Column: Waters Xterra MSC18 (5 μm, 4.6×50 mm)
  Eluent: acetonitrile/0.1% aqueous formic acid (10/90→30/70)

LC/MS Conditions 5
  Column: Waters Xterra MSC18 (5 μm, 4.6×50 mm)
  Eluent: acetonitrile/0.1% aqueous formic acid (10/90→60/40)

LC/MS Conditions 6
  Column: Waters Xterra MSC18 (5 μm, 4.6×50 mm)
  Eluent: acetonitrile/0.1% aqueous formic acid (10/90→85/15)

LC/MS Conditions 7
  Column: Waters Xterra MSC18 (5 μm, 4.6×50 mm)
  Eluent: acetonitrile/0.1% aqueous formic acid (20/80→100/0)

LC/MS Conditions 8
  Column: Waters Xterra MSC18 (3.5 μm, 2.1×20 mm)
  Eluent: acetonitrile/0.2% aqueous formic acid (20/80→90/10)

Reference Synthetic Example 1

Synthesis of 5-(4-isopropylpiperazine-1-carbonyl)thiophene-2-carbohydrazide

A solution of 59 mg (0.02 mmol) of methyl 5-(4-isopropylpiperazine-1-carbonyl)thiophene-2-carboxylate was dissolved in 2 mL of ethanol was heated with 100 μL of hydrazine monohydrate at 80° C. for 5 hours with reflux. After cooling, the reaction solution was poured into a liquid mixture of 5 mL of water and 5 mL of saturated aqueous sodium chloride and extracted with 20 mL of ethyl acetate and 20 mL of chloroform.

The extract was dried over magnesium sulfate, and the solvent was evaporated at 40° C. to give 30 mg of the desired product, 5-(4-isopropylpiperazine-1-carbonyl)thiophene-2-carbohydrazide (yield 51%).
  Morphology: colorless solid
  LC/MS: conditions 4 retention time 0.32 (min)
  LC/MS (ESI$^+$) m/z; 297 [M+1]$^+$
  LC/MS (ESI$^-$) m/z; 295 [M-1]$^-$ Reference Synthetic Example 2

Synthesis of 5-(morpholine-4-carbonyl)thiophene-2-carbohydrazide

The procedure in Reference Synthetic Example 1 was followed using methyl 5-(morpholine-4-carbonyl)thiophene-2-carboxylate to give the desired product, 5-(morpholine-4-carbonyl)thiophene-2-carbohydrazide (yield 51%).
  Morphology: colorless solid
  LC/MS: conditions 5 retention time 0.34 (min)
  LC/MS (ESI$^+$) m/z; 256 [M+1]$^+$
  LC/MS (ESI$^-$) m/z; 254 [M-1]$^-$ Reference Synthetic Example 3

Synthesis of 5-hydrazinocarbonylthiophene-2-carboxylic acid diethylamide

The procedure in Reference Synthetic Example 1 was followed using methyl 5-(diethylcarbamoyl)thiophene-2-carboxylate to give the desired product, 5-hydrazinocarbonylthiophene-2-carboxylic acid diethylamide (yield 89%).
  Morphology: white solid
  LC/MS: conditions 8 retention time 0.63 (min)
  LC/MS (ESI$^+$) m/z; 242 [M+1]$^+$ Reference Synthetic Example 4

Synthesis of 5-(pyrrolidine-1-carbonyl)thiophene-2-carbohydrazide

The procedure in Reference Synthetic Example 1 was followed using methyl 5-(pyrrolidine-1-carbonyl)thiophene-2-carboxylate to give the desired product, 5-(pyrrolidine-1-carbonyl)thiophene-2-carbohydrazide.
  Morphology: white solid
  LC/MS: conditions 8 retention time 0.50 (min)
  LC/MS (ESI$^+$) m/z; 240 [M+1]$^+$ Reference Synthetic Example 5

Synthesis of 5-hydrazinocarbonylthiophene-2-carboxylic acid dimethylamide

The procedure in Reference Synthetic Example 1 was followed using methyl 5-(dimethylcarbamoyl)thiophene-2-carboxylate to give the desired product, 5-hydrazinocarbonylthiophene-2-carboxylic acid dimethylamide (yield 23%).
  Morphology: colorless solid
  LC/MS: conditions 6 retention time 0.37 (min)
  LC/MS (ESI$^+$) m/z; 214 [M+1]$^+$
  LC/MS (ESI$^-$) m/z; 212 [M-1]$^-$ Reference Synthetic Example 6

Synthesis of 5-hydrazinocarbonylthiophene-2-carboxylic acid 2-methoxyethylamide

The procedure in Reference Synthetic Example 1 was followed using methyl 5-(2-methoxyethylcarbamoyl)thiophene-2-carboxylate to give the desired product, 5-hydrazinocarbonylthiophene-2-carboxylic acid 2-methoxyethylamide (yield 84%).

Morphology: white solid
LC/MS: conditions 1 retention time 0.34 (min)
LC/MS (ESI$^+$) m/z; 244 [M+1]$^+$
LC/MS (ESI$^-$) m/z; 242 [M−1]$^-$ Reference Synthetic Example 7

Synthesis of
5-hydrazinocarbonylthiophene-2-carboxylic acid
3-pyridylamide

The procedure in Reference Synthetic Example 1 was followed using methyl 5-(3-pyridylcarbamoyl)thiophene-2-carboxylate to give the desired product, 5-hydrazinocarbonylthiophene-2-carboxylic acid 3-pyridylamide (yield 78%).
Morphology: colorless solid
LC/MS: conditions 1 retention time 0.34 (min)
LC/MS (ESI$^+$) m/z; 263 [M+1]$^+$
LC/MS (ESI$^-$) m/z; 261 [M−1]$^-$ Reference Synthetic Example 8

Synthesis of 2-chloro-4-hydrazinocarbonyl-N-(2-hydroxyethyl)benzamide

The procedure in Reference Synthetic Example 1 was followed using methyl 3-chloro-N-(2-hydroxyethyl)terephthalic acid methyl ester to give the desired product, 2-chloro-4-hydrazinocarbonyl-N-(2-hydroxyethyl)benzamide (yield 66%).
Morphology: colorless solid
LC/MS: conditions 2 retention time 0.32 (min)
LC/MS (ESI$^+$) m/z; 258, 260 [M+1]$^+$
LC/MS (ESI$^-$) m/z; 256, 258 [M−1]$^-$ Reference Synthetic Example 9

Synthesis of 5-(2-cyanobutyryl)thiophene-2-carbohydrazide methyl 5-(2-cyanobutyryl)thiophene-2-carboxylate To butyronitrile (957 μL, 11 mmol) in tetrahydrofuran, lithium hexamethyldisilazide (12.5 mL 1M tetrahydrofuran solution, 12.5 mmol) was added at −78° C., and the resulting solution was stirred for 1 hour and added dropwise to 5-methoxycarbonylthiophene-2-carbonyl chloride (1.02 g, 5 mmol) in tetrahydrofuran at −78° C. over 30 minutes, and the resulting reaction mixture was stirred at room temperature for 1 hour. The solvent was evaporated, and the reaction solution was mixed with ethyl acetate and washed with saturated aqueous ammonium chloride and saturated sodium chloride and purified by silica gel column chromatography (eluent hexane/ethyl acetate=3/1) to give the desired product, methyl 5-(2-cyanobutyryl)thiophene-2-carboxylate (yield 41%).
Morphology: yellow solid
LC/MS: conditions 3 retention time 2.45 (min)
LC/MS (ESI$^+$) m/z; 238 [M+1]$^+$
LC/MS (ESI$^-$) m/z; 236 [M−1]$^-$ 5-(2-Cyanobutyryl)thiophene-2-carbohydrazide Methyl 5-(cyanobutyryl)thiophene-2-carboxylate (213 mg, 0.90 mmol) in methanol was stirred with 0.1 M potassium hydroxide in methanol (9.0 mL, 0.90 mmol) at room temperature for 10 minutes and then with hydrazine monohydrate (225 mg, 4.50 mg) at 80° C. for 6 hours. After addition of saturated aqueous sodium chloride, the reaction solution was extracted with ethyl acetate, dried over anhydrous magnesium sulfate and concentrated to give the crude desired product.
Morphology: yellow solid Reference Synthetic Example 10

Synthesis of
5-hydrazinocarbonylthiophene-2-carboxylic acid
methyl-2-picolylamide The procedure in Reference Synthetic Example 1 was followed using methyl 5-(methyl-2-picolylamido)thiophene-2-carboxylate to give the desired product, 5-hydrazinocarbonylthiophene-2-carboxylic acid methyl-2-picolylamide (yield 77%).
Morphology: white solid
LC/MS: conditions 8 retention time 0.45 (min)
LC/MS (ESI$^+$) m/z; 291 [M+1]$^+$
LC/MS (ESI$^-$) m/z; 289 [M−1]$^-$ Reference Synthetic Example 11

Synthesis of
5-hydrazinocarbonylthiophene-2-carboxylic acid
3-picolylamide

Methyl 5-(3-picolylcarbamoyl)thiophene-2-carboxylate (860 mg, 3.11 mmol) in ethanol (34 mL) was stirred with hydrazine monohydrate (1.57 m, 31.1 mmol) at 85° C. for 12 hours. The reaction solution was concentrated and stirred with diethyl ether at 0° C. for 1 hour. The precipitated solid was recovered by filtration and washed with a liquid mixture of diethyl ether and ethanol and dried to give the desired product, 5-hydrazinocarbonylthiophene-2-carboxylic acid 3-picolylamide (yield 92%).
Morphology: white solid
LC/MS: conditions 1 retention time 0.23 (min)
LC/MS (ESI$^+$) m/z; 277 [M+1]$^+$
LC/MS (ESI$^-$) m/z; 275 [M−1]$^-$ Reference Synthetic Example 12

Synthesis of
5-hydrazinocarbonylthiophene-2-carboxylic acid
4-picolylamide

The procedure in Reference Synthetic Example 11 was followed using methyl 5-(4-picolylcarbamoyl)thiophene-2-carboxylate to give the desired product, 5-hydrazinocarbonylthiophene-2-carboxylic acid 4-picolylamide (yield 81%).
Morphology: white solid
LC/MS: conditions 1 retention time 0.23 (min)
LC/MS (ESI$^+$) m/z; 277 [M+1]$^+$
LC/MS (ESI$^-$) m/z; 275 [M−1]$^-$ Reference Synthetic Example 13

Synthesis of
5-hydrazinocarbonylthiophene-2-carboxylic acid
(furan-2-ylmethyl)amide The procedure in Reference Synthetic Example 11 was followed using methyl 5-(furan-2-ylmethylcarbamoyl)thiophene-2-carboxylate to give the desired product, 5-hydrazinocarbonylthiophene-2-carboxylic acid (furan-2-ylmethyl)amide (yield 86%).

Morphology: white solid
LC/MS: conditions 3 retention time 1.50 (min)
LC/MS (ESI$^+$) m/z; 266 [M+1]$^+$
LC/MS (ESI$^-$) m/z; 264 [M−1]$^-$ Reference Synthetic Example 14

Synthesis of
5-hydrazinocarbonylthiophene-2-carboxylic acid
methylamide

The procedure in Reference Synthetic Example 11 was followed using methyl 5-(methylcarbamoyl)thiophene-2-carboxylate to give the desired product, 5-hydrazinocarbonylthiophene-2-carboxylic acid methylamide (yield 83%).
Morphology: pale yellow solid
LC/MS: conditions 3 retention time 0.37 (min)
LC/MS (ESI$^+$) m/z; 200 [M+1]$^+$
LC/MS (ESI$^-$) m/z; 198 [M−1]$^-$ Reference Synthetic Example 15

Synthesis of
5-hydrazinocarbonylthiophene-2-carboxylic acid
isopropylamide

The procedure in Reference Synthetic Example 11 was followed using methyl 5-(isopropylcarbamoyl)thiophene-2-carboxylate to give the desired product, 5-hydrazinocarbonylthiophene-2-carboxylic acid isopropylamide (yield 45%).
Morphology: white solid
LC/MS: conditions 2 retention time 1.07 (min)
LC/MS (ESI$^+$) m/z; 228 [M+1]$^+$
LC/MS (ESI$^-$) m/z; 226 [M−1]$^-$ Reference Synthetic Example 16

Synthesis of
5-hydrazinocarbonylthiophene-2-carboxylic acid
2-picolylamide

The procedure in Reference Synthetic Example 11 was followed using methyl 5-(2-picolylcarbamoyl)thiophene-2-carboxylate to give the desired product, 5-hydrazinocarbonylthiophene-2-carboxylic acid 2-picolylamide (yield 81%).
Morphology: white solid
LC/MS: conditions 1 retention time 0.28 (min)
LC/MS (ESI$^+$) m/z; 277 [M+1]$^+$
LC/MS (ESI$^-$) m/z; 275 [M−1]$^-$ Reference Synthetic Example 17

Synthesis of
5-hydrazinocarbonylthiophene-2-carboxylic acid
(2-pyridin-4-yl)ethylamide Methyl 5-[2-(pyridin-4-yl)ethylcarbamoyl]thiophene-2-carboxylate (0.40 g, 1.4 mmol) was suspended in a liquid mixture of methanol (4.0 mL) and tetrahydrofuran (2.0 mL) and left at 55° C. until conversion to a homogeneous amber solution was confirmed. After addition of 80% hydrazine monohydrate (0.17 mL, 2.8 mmol), it was left at 55° C. for 24 hours. After addition of 80% hydrazine monohydrate (0.17 mL, 2.8 mmol), it was left at 55° C. for 4.5 hours and then at room temperature for 14 hours. The precipitated solid was recovered by filtration and dried to give the desired product, 5-hydrazinocarbonylthiophene-2-carboxylic acid (2-pyridin-4-yl)ethylamide (yield 82%).
Morphology: white solid
$^1$H-NMR (DMSO-d$_6$) δ: 2.86 (t, J=7.0 Hz, 2H), 3.50 (dt, J=5.5 & 7.0 Hz, 2H), 4.52 (br s, 2H), 7.26 (d, J=6.0 Hz, 2H), 8.46 (d, J=6.0 Hz, 2H), 8.72 (t, J=5.5 Hz, 1H), 9.90 (br s, 1H).

Reference Synthetic Example 18

Synthesis of
5-hydrazinocarbonylthiophene-2-carboxylic acid
(1-methyl-1H-pyrazol-5-ylmethyl)amide Methyl 5-(1-methyl-1H-pyrazol-5-ylmethylcarbamoyl)thiophene-2-carboxylate (0.25 g, 0.90 mmol) in methanol (2.5 mL) was stirred with hydrazine monohydrate (0.17 mL, 3.6 mmol) at 70° C. for 3.5 hours. The precipitated solid was recovered by filtration, washed with chloroform and dried to give the desired product, 5-hydrazinocarbonylthiophene-2-carboxylic acid (1-methyl-1H-pyrazol-5-ylmethyl)amide (yield 49%).
Morphology: white solid
LC/MS: conditions 2 retention time 0.40 (min)
LC/MS (ESI$^+$) m/z; 280 [M+1]$^+$
LC/MS (ESI$^-$) m/z; 278 [M−1]$^-$ Reference Synthetic Example 19

Synthesis of
5-hydrazinocarboynlthiophene-2-carboxylic acid
(5-methylisoxazol-3-ylmethyl)amide The procedure in Reference Synthetic Example 18 was followed using methyl 5-(5-methylisoxazol-3-ylmethylcarbamoyl)thiophene-2-carboxylate to give the desired product, 5-hydrazinocarboynlthiophene-2-carboxylic acid (5-methylisoxazol-3-ylmethyl)amide (yield 47%).
Morphology: white solid
LC/MS: conditions 2 retention time 1.00 (min)
LC/MS (ESI$^+$) m/z; 281 [M+1]$^+$
LC/MS (ESI$^-$) m/z; 279 [M−1]$^-$ Reference Synthetic Example 20

Synthesis of
5-hydrazinocarbonylthiophene-2-carboxylic acid
(5-methylpyrazin-2-ylmethyl)amide Methyl 5-(5-methylpyrazin-2-ylmethylcarbamoyl)thiophene-2-carboxylate (304 mg, 1.04 mmol) in methanol (3 mL) was stirred with hydrazine monohydrate at 60° C. for 12 hours. After addition of chloroform, it was stirred at room temperature for 5 hours. The precipitated solid was recovered by filtration to give the desired product, 5-hydrazinocarbonylthiophene-2-carboxylic acid (5-methylpyrazin-2-ylmethyl)amide (yield 72%).
Morphology: white solid
LC/MS: conditions 3 retention time 0.69 (min)
LC/MS (ESI$^+$) m/z; 292 [M+1]$^+$
LC/MS (ESI$^-$) m/z; 290 [M−1]$^-$ Reference Synthetic Example 21

Synthesis of
5-hydrazinocarbonylthiophene-2-carboxylic acid
(isoxazol-5-ylmethyl)amide The procedure in Reference Synthetic Example 18 was followed using methyl 5-(isoxazol-5-ylmethylcarbamoyl)

thiophene-2-carboxylate to give the desired product, 5-hydrazinocarbonylthiophene-2-carboxylic acid (isoxazol-5-ylmethyl)amide (yield 46%).
Morphology: white solid
LC/MS: conditions 2 retention time 0.62 (min)
LC/MS (ESI$^+$) m/z; 267 [M+1]$^+$
LC/MS (ESI$^-$) m/z; 265 [M−1]$^-$ Reference Synthetic Example 22

Synthesis of 5-hydrazinocarbonylthiophene-2-carboxylic acid (3-methoxyisoxazol-5-ylmethyl)amide The procedure in Reference Synthetic Example 18 was followed using methyl 5-(3-methoxyisoxazol-5-ylmethylcarbamoyl)thiophene-2-carboxylate to give the desired product, 5-hydrazinocarbonylthiophene-2-carboxylic acid (3-methoxyisoxazol-5-ylmethyl)amide (yield 50%).
Morphology: colorless solid
LC/MS: conditions 2 retention time 1.25 (min)
LC/MS (ESI$^+$) m/z; 297 [M+1]$^+$
LC/MS (ESI$^-$) m/z; 295 [M−1]$^-$ Reference Synthetic Example 23

Synthesis of 5-hydrazinocarbonylthiophene-2-carboxylic acid (1,5-dimethyl-1H-pyrazol-3-ylmethyl)amide The procedure in Reference Synthetic Example 18 was followed using methyl 5-(1,5-dimethyl-1H-pyrazol-3-ylmethylcarbamoyl)thiophene-2-carboxylate to give the desired product, 5-hydrazinocarbonylthiophene-2-carboxylic acid (1,5-dimethyl-1H-pyrazol-3-ylmethyl)amide (yield 59%).
Morphology: white solid
LC/MS: conditions 2 retention time 1.00 (min)
LC/MS (ESI$^+$) m/z; 294 [M+1]$^+$
LC/MS (ESI$^-$) m/z; 292 [M−1]$^-$ Reference Synthetic Example 24

Synthesis of 5-hydrazinocarbonylthiophene-2-carboxylic acid (pyrazin-2-ylmethyl)amide The procedure in Reference Synthetic Example 18 was followed using methyl 5-(pyrazin-2-ylmethylcarbamoyl)thiophene-2-carboxylate to give the desired product, 5-hydrazinocarbonylthiophene-2-carboxylic acid (pyrazin-2-ylmethyl)amide (yield 82%).
Morphology: white solid
LC/MS: conditions 2 retention time 0.37 (min)
LC/MS (ESI$^+$) m/z; 278 [M+1]$^+$
LC/MS (ESI$^-$) m/z; 276 [M−1]$^-$ Reference Synthetic Example 25 a) Synthesis of 4-[{5-(methoxycarbonyl)thiophene-2-carboxamido}methyl]pyridine 1-oxide 5-Hydrazinocarbonylthiophene-2-carboxylic acid 4-picolylamide (0.20 g, 0.72 mmol) prepared in Reference Synthetic Example 12 in chloroform (4.0 mL) was stirred with 65 wt % m-chloroperbenzoic acid (0.21 g, 0.80 mmol) at room temperature for 9 hours, then left for 18 hours and concentrated to dryness under reduced pressure. Chloroform (30 mL), saturated aqueous sodium hydrogencarbonate (3 mL) and water (7 mL) were added to the residue, and the organic layer was separated. The aqueous layer was extracted with chloroform (10 mL×2) and hot chloroform (10 mL×1). The resulting organic layer was concentrated to give the desired crude product, 4-[{5-(methoxycarbonyl)thiophene-2-carboxamido}methyl]pyridine 1-oxide (purity 80 wt %, yield 62%).
Morphology: white solid
LC/MS: conditions 2 retention time 1.77 (min)
LC/MS (ESI$^+$) m/z; 293 [M+1]$^+$
LC/MS (ESI$^-$) m/z; 291 [M−1]$^-$ b) Synthesis of 4-[{5-hydrazniocarbonyl)thiophene-2-carboxamido}methyl]pyridine 1-oxide 4-[{5-(Methoxycarbonyl)thiophene-2-carboxamido}methyl]pyridine 1-oxide (0.12 g, 0.34 mmol) prepared above suspended in methanol (2.0 mL) was left at 60° C. After addition of 80% hydrazine monohydrate (0.082 mL, 1.4 mmol), it was left at 60° C. for 3.5 hours, then at room temperature for 5.5 hours and at 0° C. for 11.5 hours. The precipitated solid was recovered by filtration and dried to give the desired product, 4-[{5-hydrazniocarbonyl)thiophene-2-carboxamido}methyl]pyridine 1-oxide (yield 51%).
Morphology: pale yellow solid
LC/MS: conditions 2 retention time 0.37 (min)
LC/MS (ESI$^+$) m/z; 293 [M+1]$^+$
LC/MS (ESI$^-$) m/z; 291 [M−1]$^-$
$^1$H-NMR (DMSO-d$_6$) δ: 4.42 (br s, 2H), 4.51 (br s, 0.7H), 7.32 (d, J=7.0 Hz, 2H), 7.68 (d, J=4.0 Hz, 1H), 7.75 (d, J=7.0 Hz, 1H), 8.17 (d, J=7.0 Hz, 2H), 9.25 (t, J=6.0 Hz, 0.3H), 9.92 (br s, 0.3H).

Reference Synthetic Example 26

Synthesis of 5-hydrazinocarbonylthiophene-2-carboxylic acid 3-(pyridin-4-yl)propylamide 80% Hydrazine monohydrate (0.17 mL, 2.8 mmol) was added to methyl 5-[3-(pyridin-4-yl)propylcarbamoyl]thiophene-2-carboxylate (0.28 g, 0.92 mmol) in methanol (10 mL), and the reaction solution was left at 50° C. for 95 hours. After addition of 80% hydrazine monohydrate (0.17 mL, 2.8 mmol), it was left at 55° C. for another 14 hours and concentrated to dryness by evaporating the solvent under reduced pressure. Methanol (2 mL) was added to the residue, and the resulting solution was put on a sonicator. The precipitated solid was recovered by filtration and dried to give the desired product, 5-hydrazinocarbonylthiophene-2-carboxylic acid 3-(pyridin-4-yl)propylamide (yield 61%).
Morphology: white solid
$^1$H-NMR (DMSO-d$_6$) δ: 1.84 (tt, J=7.5 & 6.5 Hz, 2H), 2.64 (t, J=7.5 Hz, 2H), 3.25 (dt, J=5.5 & 6.5 Hz, 2H), 4.54 (br s, 1.6H), 7.26 (d, J=6.0 Hz, 2H), 7.65 (d, J=4.0 Hz, 1H), 7.67 (d, J=4.0 Hz, 1H), 8.45 (d, J=6.0 Hz, 2H), 8.65 (br t, J=5.5 Hz, 0.9H), 9.90 (br s, 0.9H).

Reference Synthetic Example 27

Synthesis of 5-hydrazinocarbonylthiophene-2-carboxylic acid (1-methyl-1H-imidazol-5-ylmethyl)amide The procedure in Reference Synthetic Example 18 was followed using methyl 5-(1-methyl-1H-imidazol-5-ylmethylcarbamoyl)thiophene-2-carboxylate to give the desired product, 5-hydrazinocarbonylthiophene-2-carboxylic acid (1-methyl-1H-imidazol-5-ylmethyl)amide (yield 70%).

Morphology: pale yellow solid
LC/MS: conditions 3 retention time 0.30 (min)
LC/MS (ESI$^+$) m/z; 280 [M+1]$^+$
LC/MS (ESI$^-$) m/z; 278 [M−1]$^-$ Reference Synthetic Example 28

Synthesis of 5-(3-hydroxypyrrolidine-1-carbonyl)thiophene-2-carbohydrazide

The procedure in Reference Synthetic Example 18 was followed using methyl 5-(3-hydroxypyrrolidine-1-carbonyl)thiophene-2-carboxylate to give the desired product, 5-(3-hydroxypyrrolidine-1-carbonyl)thiophene-2-carbohydrazide (yield 53%).

Morphology: white solid

Synthetic Example 1

Synthesis of 5-(4-isopropylpiperazine-1-carbonyl)thiophene-2-carboxylic acid {1-[5-(3,4-dichlorophenyl)-4-hydroxythiophen-3-yl]ethylidene}hydrazide 5-(4-Isopropylpiperazine-1-carbonyl)thiophene-2-carboxylic acid {1-[5-(3,4-dichlorophenyl)-4-hydroxythiophen-3-yl]ethylidene}hydrazide hydrochloride 28 mg of 2-(3,4-dichlorophenyl)-3-hydroxy-4-methylcarbonylthiophene (synthesized in accordance with WO2004/108683) and 29.7 mg of 5-(4-isopropylpiperazine-1-carbonyl)thiophene-2-carbohydrazide prepared in Reference Synthetic Example 1 in 2 mL of isopropyl alcohol were heated with 3 mg of p-tosylic acid monohydrate and 25 µL (1 eq) of 4 M hydrogen chloride/dioxane at 105° C. for 8 hours. The reaction solution was further heated with 2 mL of dimethylformamide at 105° C. for 5 hours and cooled to room temperature. The precipitated solid was recovered by filtration and washed with 1 mL of isopropyl alcohol and 1 mL of chloroform, and the resulting crystals were dried to give the desired product (yield 54%).

Morphology: colorless solid
LC/MS: conditions 5 retention time 3.80 (min)
LC/MS (ESI$^+$) m/z; 565, 567 [M+1]$^+$
LC/MS (ESI$^-$) m/z; 563, 565 [M−1]$^-$ 5-(4-Isopropylpiperazine-1-carbonyl)thiophene-2-carboxylic acid {1-[5-(3,4-dichlorophenyl)-4-hydroxythiophen-3-yl]ethylidene}hydrazide 5-(4-Isopropylpiperazine-1-carbonyl)thiophene-2-carboxylic acid {1-[5-(3,4-dichlorophenyl)-4-hydroxythiophen-3-yl]ethylidene}hydrazide hydrochloride (14 mg, 0.025 mmol) was suspended in methanol (2.7 mL), and 0.1 M potassium hydroxide in methanol (0.24 mL) and methanol (5.4 mL) were added. The suspension was heated at 50° C. and concentrated to dryness under reduced pressure to give the desired product (yield 100%).

Morphology: light brown solid

Synthetic Example 2

Synthesis of 5-(morpholine-4-carbonyl)thiophene-2-carboxylic acid {1-[5-(3,4-dichlorophenyl)-4-hydroxythiophen-3-yl]ethylidene}hydrazide potassium salt 5-(Morpholine-4-carbonyl)thiophene-2-carboxylic acid {1-[5-(3,4-dichlorophenyl)-4-hydroxythiophen-3-yl]ethylidene}hydrazide 28 mg of 2-(3,4-dichlorophenyl)-3-hydroxy-4-methylcarbonylthiophene and 26 mg of 5-(morpholine-4-carbonyl)thiophene-2-carbohydrazide prepared in Reference Synthetic Example 2 were heated in isopropyl alcohol with 3 mg of p-tosylic acid monohydrate at 105° C. for 18 hours and cooled to room temperature. The precipitated solid was recovered by filtration and washed with 1 mL of isopropyl alcohol, and the resulting crystals were dried to give the desired product (yield 86%).

Morphology: pale yellow solid
LC/MS: conditions 5 retention time 4.89 (min)
LC/MS (ESI$^+$) m/z; 524, 526 [M+1]$^+$
LC/MS (ESI$^-$) m/z; 522, 524 [M−1]$^-$ 5-(Morpholine-4-carbonyl)thiophene-2-carboxylic acid {1-[5-(3,4-dichlorophenyl)-4-hydroxythiophen-3-yl]ethylidene}hydrazide potassium salt 5-(Morpholine-4-carbonyl)thiophene-2-carboxylic acid {1-[5-(3,4-dichlorophenyl)-4-hydroxythiophen-3-yl]ethylidene}hydrazide (20 mg, 0.038 mmol) was suspended in methanol (2.4 mL), and 0.1 M potassium hydroxide in methanol (0.38 mL) and then methanol (5.6 mL) were added. The suspension was heated at 50° C. and concentrated to dryness under reduced pressure to give the desired product (yield 100%).

Synthetic Example 3

Synthesis of 5-{1-[5-(3,4-dichlorophenyl)-4-hydroxythiophen-3-yl]ethylidenehydrazinocarbonyl}thiophene-2-carboxylic acid diethylamide potassium salt 5-{1-[5-(3,4-Dichlorophenyl)-4-hydroxythiophen-3-yl]ethylidenehydrazinocarbonyl}thiophene-2-carboxylic acid diethylamide Synthesis was carried out in the same manner as in Synthetic Example 2 by using 2-(3,4-dichlorophenyl)-3-hydroxy-4-methylcarbonylthiophene and 5-hydrazinocarbonylthiophene-2-carboxylic acid diethylamide prepared in Reference Synthetic Example 3 (yield 76%).

Morphology: pale yellow solid
LC/MS: conditions 5 retention time 5.82 (min)
LC/MS (ESI$^+$) m/z; 510, 512 [M+1]$^+$
LC/MS (ESI$^-$) m/z; 508, 510 [M−1]$^-$ 5-{1-[5-(3,4-Dichlorophenyl)-4-hydroxythiophen-3-yl]ethylidenehydrazinocarbonyl}thiophene-2-carboxylic acid diethylamide potassium salt Synthesis was carried out in the same manner as in Synthetic Example 2 by using 5-{1-[5-(3,4-dichlorophenyl)-4- hydroxythiophen-3-yl]ethylidenehydrazinocarbonyl}thiophene-2-carboxylic acid diethylamide (yield 100%).
Morphology: orange solid

Synthetic Example 4

Synthesis of 5-(pyrrolidine-1-carbonyl)thiophene-2-carboxylic acid {1-[5-(3,4-dichlorophenyl)-4-hydroxythiophen-3-yl]ethylidene}hydrazide potassium salt 5-(Pyrrolidine-1-carbonyl)thiophene-2-carboxylic acid {1-[5-(3,4-dichlorophenyl)-4-hydroxythiophen-3-yl]ethylidene}hydrazide Synthesis was carried out in the same manner as in Synthetic Example 2 by using 2-(3,4-dichlorophenyl)-3-hydroxy-4-methylcarbonyl)thiophene and 5-(pyrrolidine-1-carbonyl)thiophene-2-carbohydrazide prepared in Reference Synthetic Example 4 (yield 94%).
Morphology: pale yellow solid
LC/MS: conditions 5 retention time 5.34 (min)
LC/MS (ESI$^+$) m/z; 508, 510 [M+1]$^+$
LC/MS (ESI$^-$) m/z; 506, 508 [M−1]$^-$ 5-(Pyrrolidine-1-carbonyl)thiophene-2-carboxylic acid {1-[5-(3,4-dichlorophenyl)-4-hydroxythiophen-3-yl]ethylidene}hydrazide potassium salt Synthesis was carried out in the same manner as in Synthetic Example 2 by using 5-(pyrrolidine-1-carbonyl)thiophene-2-carboxylic acid {1-[5-(3,4-dichlorophenyl)-4-hydroxythiophen-3-yl]ethylidene}hydrazide (yield 100%).
Morphology: orange solid

Synthetic Example 5

Synthesis of 5-{1-[5-(3,4-dichlorophenyl)-4-hydroxythiophen-3-yl]ethylidenehydrazinocarbonyl}thiophene-2-carboxylic acid dimethylamide potassium salt 5-{1-[5-(3,4-Dichlorophenyl)-4-hydroxythiophen-3-yl]ethylidenehydrazinocarbonyl}thiophene-2-carboxylic acid dimethylamide Synthesis was carried out in the same manner as in Synthetic Example 2 by using 2-(3,4-dichlorophenyl)-3-hydroxy-4-methylcarbonylthiophene and 5-hydrazinocarbonylthiophene-2-carboxylic acid dimethylamide prepared in Reference Synthetic Example 5 (yield 65%).
Morphology: colorless solid
LC/MS: conditions 5 retention time 4.93 (min)
LC/MS (ESI$^+$) m/z; 482, 484 [M+1]$^+$
LC/MS (ESI$^-$) m/z; 480, 482 [M−1]$^-$ 5-{1-[5-(3,4-Dichlorophenyl)-4-hydroxythiophen-3-yl]ethylidenehydrazinocarbonyl}thiophene-2-carboxylic acid dimethylamide potassium salt Synthesis was carried out in the same manner as in Synthetic Example 2 by using 5-{1-[5-(3,4-dichlorophenyl)-4-hydroxythiophen-3-yl]ethylidenehydrazinocarbonyl}thiophene-2-carboxylic acid dimethylamide (yield 100%).
Morphology: orange solid

Synthetic Example 6

Synthesis of 5-{1-[5-(3,4-dichlorophenyl)-4-hydroxythiophen-3-yl]ethylidenehydrazinocarbonyl}thiophene-2-carboxylic acid 2-methoxyethylamide potassium salt 5-{1-[5-(3,4-Dichlorophenyl)-4-hydroxythiophen-3-yl]ethylidenehydrazinocarbonyl}thiophene-2-carboxylic acid 2-methoxyethylamide Synthesis was carried out in the same manner as in Synthetic Example 2 by using 2-(3,4-dichlorophenyl)-3-hydroxy-4-methylcarbonylthiophene and 5-hydrazinocarbonylthiophene-2-carboxylic acid 2-methoxyethylamide prepared in Reference Synthetic Example 6 (yield 80%).
Morphology: pale yellow solid
LC/MS: conditions 7 retention time 3.15 (min)
LC/MS (ESI$^+$) m/z; 512, 514 [M+1]$^+$
LC/MS (ESI$^-$) m/z; 510, 512 [M−1]$^-$ 5-{1-[5-(3,4-Dichlorophenyl)-4-hydroxythiophen-3-yl]ethylidenehydrazinocarbonyl}thiophene-2-carboxylic acid 2-methoxyethylamide potassium salt Synthesis was carried out in the same manner as in Synthetic Example 2 by using 5-{1-[5-(3,4-dichlorophenyl)-4-hydroxythiophen-3-yl]ethylidenehydrazinocarbonyl}thiophene-2-carboxylic acid 2-methoxyethylamide (yield 100%).
Morphology: orange solid

Synthetic Example 7

Synthesis of 5-{1-[5-(3,4-dichlorophenyl)-4-hydroxythiophen-3-yl]ethylidenehydrazinocarbonyl}thiophene-2-carboxylic acid 3-pyridylamide potassium salt 5-{1-[5-(3,4-Dichlorophenyl)-4-hydroxythiophen-3-yl]ethylidenehydrazinocarbonyl}thiophene-2-carboxylic acid 3-pyridylamide 28 mg of 2-(3,4-dichlorophenyl)-3-hydroxy-4-methylcarbonylthiophene and 26 mg of 5-hydrazinocarbonylthiophene-2-carboxylic acid 3-pyridylamide were dissolved in 2 mL of dimethyl sulfoxide and heated at 100° C. for 18 hours, and the solvent was evaporated. Recrystallization from chloroform-diethyl ether gave the desired product (yield 94%).
Morphology: pale yellow solid
LC/MS: conditions 2 retention time 4.02 (min)
LC/MS (ESI$^+$) m/z; 531, 533 [M+1]$^+$
LC/MS (ESI$^-$) m/z; 529, 531 [M−1]$^-$ 5-{1-[5-(3,4-Dichlorophenyl)-4-hydroxythiophen-3-yl]ethylidenehydrazinocarbonyl}thiophene-2-carboxylic acid 3-pyridylamide potassium salt Synthesis was carried out in the same manner as in Synthetic Example 2 by using 5-{1-[5-(3,4-dichlorophenyl)-4- hydroxythiophen-3-yl]
ethylidenehydrazinocarbonyl}thiophene-2-carboxylic acid 3-pyridylamide (yield 76%).
Morphology: orange solid

Synthetic Example 8

Synthesis of 5-{1-[5-(4-trifluoromethylphenyl)-4-hydroxythiophen-3-yl]
ethylidenehydrazinocarbonyl}thiophene-2-carboxylic acid diethylamide Synthesis was carried out in the same manner as in Synthetic Example 2 by using 2-(4-trifluoromethylphenyl)-3-hydroxy-4-methylcarbonylthiophene (synthesized in accordance with WO2004/108683) and 5-hydrazinocarbonylthiophene-2-carboxylic acid diethylamide prepared in Reference Synthetic Example 3 (yield 67%).
Morphology: pale yellow solid
LC/MS: conditions 6 retention time 3.82 (min)
LC/MS (ESI$^-$) m/z; 508 [M−1]$^-$

Synthetic Example 9

Synthesis of 5-(4-isopropylpiperazine-1-carbonyl)
thiophene-2-carboxylic acid {1-[5-(4-trifluoromethylphenyl)-4-hydroxythiophen-3-yl]
ethylidene}hydrazide potassium salt 5-(4-Isopropylpiperazine-1-carbonyl)thiophene-2-carboxylic acid {1-[5-(4-trifluoromethylphenyl)-4-hydroxythiophen-3-yl]ethylidene}hydrazide Synthesis was carried out in the same manner as in Synthetic Example 7 by using 2-(4-trifluoromethylphenyl)-3-hydroxy-4-methylcarbonylthiophene and 5-(4-isopropylpiperazine-1-carbonyl)thiophene-2-carbohydrazide prepared in Reference Synthetic Example 1 (yield 55%).
Morphology: yellow solid
LC/MS: conditions 3 retention time 2.49 (min)
LC/MS (ESI$^+$) m/z; 565 [M+1]$^+$
LC/MS (ESI$^-$) m/z; 563 [M−1]$^-$ 5-(4-Isopropylpiperazine-1-carbonyl)thiophene-2-carboxylic acid {1-[5-(4-trifluoromethylphenyl)-4-hydroxythiophen-3-yl]ethylidene}hydrazide potassium salt Synthesis was carried out in the same manner as in Synthetic Example 2 by using 5-(4-isopropylpiperazine-1-carbonyl)thiophene-2-carboxylic acid {1-[5-(4-trifluoromethylphenyl)-4-hydroxythiophen-3-yl]ethylidene}hydrazide (yield 100%).
Morphology: red solid

Synthetic Example 10

Synthesis of 5-(pyrrolidine-1-carbonyl)thiophene-2-carboxylic acid {1-[5-(4-trifluoromethylphenyl)-4-hydroxythiophen-3-yl]ethylidene}hydrazide potassium salt 5-(Pyrrolidine-1-carbonyl)thiophene-2-carboxylic acid {1-[5-(4-trifluoromethylphenyl)-4-hydroxythiophen-3-yl]ethylidene}hydrazide Synthesis was carried out in the same manner as in Synthetic Example 2 by using 2-(4-trifluoromethylphenyl)-3-hydroxy-4-methylcarbonylthiophene and 5-(pyrrolidine-1-carbonyl)thiophene-2-carbohydrazide prepared in Reference Synthetic Example 4 (yield 82%).
Morphology: pale yellow solid
LC/MS: conditions 8 retention time 5.10 (min)
LC/MS (ESI$^+$) m/z; 508 [M+1]$^+$
LC/MS (ESI$^-$) m/z; 506 [M−1]$^-$ 5-(Pyrrolidine-1-carbonyl)thiophene-2-carboxylic acid {1-[5-(4-trifluoromethylphenyl)-4-hydroxythiophen-3-yl]ethylidene}hydrazide potassium salt Synthesis was carried out in the same manner as in Synthetic Example 2 by using 5-(Pyrrolidine-1-carbonyl)thiophene-2-carboxylic acid {1-[5-(4-trifluoromethylphenyl)-4-hydroxythiophen-3-yl]ethylidene}hydrazide (yield 100%).
Morphology: red solid

Synthetic Example 11

Synthesis of 2-chloro-4-{1-[5-(3,4-dichlorophenyl)-4-hydroxythiophen-3-yl]ethylidenehydrazinocarbonyl}-N-(2-hydroxyethyl)benzamide potassium salt 2-Chloro-4-{1-[5-(3,4-dichlorophenyl)-4-hydroxythiophen-3-yl]ethylidenehydrazinocarbonyl}-N-(2-hydroxyethyl)benzamide To 2-(3,4-dichlorophenyl)-3-hydroxy-4-methylcarbonylthiophene (40 mg, 0.14 mmol) and 2-chloro-4-hydrazinocarbonyl-N-(2-hydroxyethyl)benzamide (43 mg, 0.17 mmol) prepared in Reference Synthetic Example 8 in dimethylformamide (0.7 mL), concentrated hydrochloric acid (12 μL, 0.14 mmol) was added at room temperature, and the resulting mixture was stirred at room temperature for 1 day and stirred with 2-chloro-4-hydrazinocarbonyl-N-(2-hydroxyethyl)benzamide (18 mg, 0.07 mmol) for 1 day. After addition of water, the resulting crystals were recovered by filtration and dried. Chloroform was added, and the resulting crystals were recovered by filtration to give the desired product (yield 83%).
Morphology: Pale green solid
LC/MS: conditions 3 retention time 3.42 (min)
LC/MS (ESI$^+$) m/z; 526, 528 [M+1]$^+$
LC/MS (ESI$^-$) m/z; 524, 526 [M−1]$^-$ 2-chloro-4-{1-[5-(3,4-dichlorophenyl)-4-hydroxythiophen-3-yl]ethylidenehydrazinocarbonyl}-N-(2-hydroxyethyl)benzamide potassium salt Synthesis was carried out in the same manner as in Synthetic Example 2 by using 2-chloro-4-{1-[5-(3,4-dichlorophenyl)-4-hydroxythiophen-3-yl]ethylidenehydrazinocarbonyl}-N-(2-hydroxyethyl)benzamide (yield 77%).
Morphology: red solid

Synthetic Example 12

Synthesis of 5-{1-[5-(3,4-dichlorophenyl)-4-hydroxythiophen-3-yl]
ethylidenehydrazinocarbonyl}thiophene-2-carboxylic acid methyl-2-picolylamide potassium salt 5-{1-[5-(3,4-Dichlorophenyl)-4-hydroxythiophen-3-yl]ethylidenehydrazinocarbonyl}thiophene-2-carboxylic acid methyl-2-picolylamide Synthesis was carried out in the same manner as in Synthetic Example 7 by using 2-(3,4-dichlorophenyl)-3-hydroxy-4-methylcarbonylthiophene and 5-hydrazinocarbonylthiophene-2-carboxylic acid methyl-2-picolylamide prepared in Reference Synthetic Example 10 (yield 66%).
Morphology: pale yellow solid
LC/MS: conditions 3 retention time 3.57 (min)
LC/MS (ESI$^+$) m/z; 559, 561 [M+1]$^+$
LC/MS (ESI$^-$) m/z; 557, 559 [M−1]$^-$ 5-{1-[5-(3,4-Dichlorophenyl)-4-hydroxythiophen-3-yl]ethylidenehydrazinocarbonyl}thiophene-2-carboxylic acid methyl-2-picolylamide potassium salt Synthesis was carried out in the same manner as in Synthetic Example 2 by using 5-{1-[5-(3,4-dichlorophenyl)-4-hydroxythiophen-3-yl]ethylidenehydrazinocarbonyl}thiophene-2-carboxylic acid methyl-2-picolylamide (yield 100%).
Morphology: red solid Synthetic Example 13

Synthesis of 5-{1-[5-(4-trifluoromethylphenyl)-4-hydroxythiophen-3-yl]ethylidenehydrazinocarbonyl}thiophene-2-carboxylic acid methyl-2-picolylamide potassium salt 5-{1-[5-(4-Trifluoromethylphenyl)-4-hydroxythiophen-3-yl]ethylidenehydrazinocarbonyl}thiophene-2-carboxylic acid methyl-2-picolylamide Synthesis was carried out in the same manner as in Synthetic Example 7 by using 2-(4-trifluoromethylphenyl)-3-hydroxy-4-methylcarbonylthiophene and 5-hydrazinocarbonylthiophene-2-carboxylic acid methyl-2-picolylamide prepared in Reference Synthetic Example 10.
Morphology: pale green solid 5-{1-[5-(4-Trifluoromethylphenyl)-4-hydroxythiophen-3-yl]ethylidenehydrazinocarbonyl}thiophene-2-carboxylic acid methyl-2-picolylamide potassium salt Synthesis was carried out in the same manner as in Synthetic Example 2 by using 5-{1-[5-(4-trifluoromethylphenyl)-4-hydroxythiophen-3-yl]ethylidenehydrazinocarbonyl}thiophene-2-carboxylic acid methyl-2-picolylamide (yield 100%).
Morphology: orange solid Synthetic Example 14

Synthesis of 5-(2-cyanobutyryl)thiophene-2-carboxylic acid {1-[5-(3,4-dichlorophenyl)-4-hydroxythiophen-3-yl]ethylidene}hydrazide potassium salt 5-(2-Cyanobutyryl)thiophene-2-carboxylic acid {1-[5-(3,4-dichlorophenyl)-4-hydroxythiophen-3-yl]ethylidene}hydrazide Synthesis was carried out in the same manner as in Synthetic Example 7 by using 2-(3,4-dichlorophenyl)-3-hydroxy-4-methylcarbonylthiophene and 5-(2-cyanobutyryl)thiophene-2-carbohydrazide prepared in Reference Synthetic Example 9 (yield 36%).
Morphology: yellow solid
LC/MS: conditions 3 retention time 3.45 (min)
LC/MS (ESI$^+$) m/z; 506, 508 [M+1]$^+$
LC/MS (ESI$^-$) m/z; 504, 506 [M−1]$^-$ 5-(2-Cyanobutyryl)thiophene-2-carboxylic acid {1-[5-(3,4-dichlorophenyl)-4-hydroxythiophen-3-yl]ethylidene}hydrazide potassium salt Synthesis was carried out in the same manner as in Synthetic Example 2 by using 5-(2-cyanobutyryl)thiophene-2-carboxylic acid {1-[5-(3,4-dichlorophenyl)-4-hydroxythiophen-3-yl]ethylidene}hydrazide (yield 75%).
Morphology: red solid Synthetic Example 15

Synthesis of 5-(2-cyanobutyryl)thiophene-2-carboxylic acid {1-[5-(4-trifluoromethylphenyl)-4-hydroxythiophen-3-yl]ethylidene}hydrazide potassium salt 5-(2-Cyanobutyryl)thiophene-2-carboxylic acid {1-[5-(4-trifluoromethylphenyl)-4-hydroxythiophen-3-yl]ethylidene}hydrazide Synthesis was carried out in the same manner as in Synthetic Example 7 by using 2-(4-trifluoromethylphenyl)-3-hydroxy-4-methylcarbonylthiophene and 5-(2-cyanobutyryl)thiophene-2-carbohydrazide prepared in Reference Synthetic Example 9 (yield 53%).
Morphology: yellow solid
LC/MS: conditions 3 retention time 3.82 (min)
LC/MS (ESI$^+$) m/z; 506 [M+1]$^+$
LC/MS (ESI$^-$) m/z; 504 [M−1]$^-$ 5-(2-Cyanobutyryl)thiophene-2-carboxylic acid {1-[5-(4-trifluoromethylphenyl)-4-hydroxythiophen-3-yl]ethylidene}hydrazide potassium salt Synthesis was carried out in the same manner as in Synthetic Example 2 by using 5-(2-cyanobutyryl)thiophene-2-carboxylic acid {1-[5-(4-trifluoromethylphenyl)-4-hydroxythiophen-3-yl]ethylidene}hydrazide (yield 91%).
Morphology: red solid Synthetic Example 16

Synthesis of 5-(2-cyanobutyryl)thiophene-2-carboxylic acid {1-[5-(4-bromophenyl)-4-hydroxythiophen-3-yl]ethylidene}hydrazide potassium salt 5-(2-Cyanobutyryl)thiophene-2-carboxylic acid {1-[5-(4-bromophenyl)-4-hydroxythiophen-3-yl]ethylidene}hydrazide Synthesis was carried out in the same manner as in Synthetic Example 7 by using 2-(4-bromophenyl)-3-hydroxy-4-methylcarbonylthiophene (synthesized in accordance with WO2004/108684) and 5-(2-cyanobutyryl)thiophene-2-carbohydrazide prepared in Reference Synthetic Example 9 (yield 51%).
Morphology: yellow solid
LC/MS: conditions 3 retention time 3.85 (min)
LC/MS (ESI$^+$) m/z; 516, 518 [M+1]$^+$
LC/MS (ESI$^-$) m/z; 514, 516 [M−1]$^-$ 5-(2-Cyanobutyryl)thiophene-2-carboxylic acid {1-[5-(4-bromophenyl)-4-hydroxythiophen-3-yl]ethylidene}hydrazide potassium salt Synthesis was carried out in the same manner as in Synthetic Example 2 by using 5-(2-cyanobutyryl)thiophene-2-carboxylic acid {1-[5-(4-bromophenyl)-4-hydroxythiophen-3-yl]ethylidene}hydrazide (yield 91%).
Morphology: red solid Synthetic Example 17

Synthesis of 5-{1-[5-(4-bromophenyl)-4-hydroxythiophen-3-yl]ethylidenehydrazinocarbonyl}thiophene-2-carboxylic acid 3-picolylamide 2-(4-Bromophenyl)-3-hydroxy-4-methylcarbonylthiophene (50.5 mg, 0.17 mmol) (synthesized in accordance with WO2004/108683) and 5-hydrazinocarbonylthiophene-2-carboxylic acid 3-picolylamide prepared in Reference Synthetic Example 11 were dissolved in dimethylsulfoxide (4.0 mL) and heated at 110° C. for 24 hours. The solvent was evaporated, and the residue was washed with methanol and water to give the desired product (yield 81%).
Morphology: pale yellow solid
LC/MS: conditions 6 retention time 4.15 (min)
LC/MS (ESI$^+$) m/z; 555, 557 [M+1]$^+$
LC/MS (ESI$^-$) m/z; 553, 555 [M−1]$^-$ Synthetic Example 18

Synthesis of 5-{1-[5-(4-bromophenyl)-4-hydroxythiophen-3-yl]ethylidenehydrazinocarbonyl]thiophene-2-carboxylic acid 4-picolylamide Synthesis was carried out in the same manner as in Synthetic Example 17 by using 2-(4-bromophenyl)-3-hydroxyl-4-methylcarbonylthiophene and 5-hydrazinocarbonylthiophene-2-carboxylic acid 4-picolylamide prepared in Reference Synthetic Example 12 (yield 72%).
Morphology: pale yellow solid
LC/MS: conditions 6 retention time 4.03 (min)
LC/MS (ESI$^+$) m/z; 555, 557 [M+1]$^+$
LC/MS (ESI$^-$) m/z; 553, 555 [M−1]$^-$ Synthetic Example 19

Synthesis of 5-{1-[5-(4-bromophenyl)-4-hydroxythiophen-3-yl]ethylidenehydrazinocarbonyl}thiophene-2-carboxylic acid furan-2-ylmethylamide 2-(4-Bromophenyl)-3-hydroxy-4-methylcarbonylthiophene (50.1 mg, 0.17 mmol) and 5-hydrazinocarbonylthiophene-2-carboxylic acid (furan-2-ylmethyl)amide (45.0 mg, 0.17 mmol) prepared in Reference Synthetic Example 13 in 2-propanol (4.0 mL) were heated with p-tosylic acid monohydrate (6 mg) at 100° C. for 7.5 hours and cooled to room temperature. The precipitated solid was recovered by filtration, washed with 2-propanol (1 mL) and dried to give the desired product (yield 72%).
Morphology: pale yellow solid
LC/MS: conditions 6 retention time 4.98 (min)
LC/MS (ESI$^+$) m/z; 544, 546 [M+1]$^+$
LC/MS (ESI$^-$) m/z; 542, 544 [M−1]$^-$ Synthetic Example 20

Synthesis of 5-{1-[5-(4-bromophenyl)-4-hydroxythiophen-3-yl]ethylidenehydrazinocarbonyl}thiophene-2-carboxylic acid methylamide Synthesis was carried out in the same manner as in Synthetic Example 19 by using 2-(4-bromophenyl)-3-hydroxy-4-methylcarbonylthiophene and 5-hydrazinocarbonylthiophene-2-carboxylic acid methylamide prepared in Reference Synthetic Example 14 (yield 65%).
Morphology: pale yellow solid
LC/MS: conditions 6 retention time 4.67 (min)
LC/MS (ESI$^+$) m/z; 478, 480 [M+1]$^+$
LC/MS (ESI$^-$) m/z; 476, 478 [M−1]$^-$ Synthetic Example 21

Synthesis of 5-{1-[5-(4-bromophenyl)-4-hydroxythiophen-3-yl]ethylidenehydrazinocarbonyl}thiophene-2-carboxylic acid isopropylamide Synthesis was carried out in the same manner as in Synthetic Example 19 by using 2-(4-bromophenyl)-3-hydroxy-4-methylcarbonylthiophene and 5-hydrazinocarbonylthiophene-2-carboxylic acid isopropylamide prepared in Reference Synthetic Example 15 (yield 70%).
Morphology: white solid
LC/MS: conditions 2 retention time 4.50 (min)
LC/MS (ESI$^+$) m/z; 506, 508 [M+1]$^+$
LC/MS (ESI$^-$) m/z; 504, 506 [M−1]$^-$ Synthetic Example 22

Synthesis of 5-{1-[4-hydroxy-5-(4-trifluoromethoxyphenyl)thiophen-3-yl]ethylidenehydrazinocarbonylthiophene-2-carboxylic acid 2-picolylamide Synthesis was carried out in the same manner as in Synthetic Example 17 by using 3-hydroxy-2-(4-trifluoromethoxyphenyl)-4-methylcarbonylthiophene (synthesized in accordance with WO2004/108683) and 5-hydrazinocarbonylthiophene-2-carboxylic acid 2-picolylamide prepared in Reference Synthetic Example 16 (yield 76%).
Morphology: pale yellow solid
LC/MS: conditions 2 retention time 3.92 (min)
LC/MS (ESI$^+$) m/z; 561 [M+1]$^+$
LC/MS (ESI$^-$) m/z; 559 [M−1]$^-$ Synthetic Example 23

Synthesis of 5-{1-[5-(4-trifluoromethylphenyl)-4-hydroxythiophen-3-yl]ethylidenehydrazinocarbonyl}thiophene-2-carboxylic acid isopropylamide Synthesis was carried out in the same manner as in Synthetic Example 19 by using 2-(4-trifluoromethylphenyl)-3-hydroxy-4-methylcarbonylthiophene (synthesized in accordance with WO2004/108683) and 5-hydrazinocarbonylthiophene-2-carboxylic acid isopropylamide prepared in Reference Synthetic Example 15 (yield 83%).
Morphology: light gray solid
LC/MS: conditions 3 retention time 3.65 (min)
LC/MS (ESI$^+$) m/z; 496 [M+1]$^+$
LC/MS (ESI$^-$) m/z; 494 [M−1]$^-$ Synthetic Example 24

Synthesis of 5-{1-5-[(4-chlorophenyl)-4-hydroxythiophen-3-yl]ethylidenehydrazinocarbonyl}thiophene-2-carboxylic acid 4-picolylamide Synthesis was carried out in the same manner as in Synthetic Example 17 by using 2-(4-chlorophenyl)-3-hydroxy-4-methylcarbonylthiophene (synthesized in accordance with WO2004/108683) and 5-hydrazinocarbonylthiophene-2-carboxylic acid 4-picolylamide prepared in Reference Synthetic Example 12 (yield 69%).
Morphology: light brown solid
LC/MS: conditions 3 retention time 2.55 (min)
LC/MS (ESI$^+$) m/z; 511, 513 [M+1]$^+$
LC/MS (ESI$^-$) m/z; 509, 511 [M−1]$^-$ Synthetic Example 25

Synthesis of 5-{1-[5-(4-chlorophenyl)-4-hydroxythiophen-3-yl]ethylidenehydrazinocarbonyl]thiophene-2-carboxylic acid 2-picolylamide Synthesis was carried out in the same manner as in Synthetic Example 17 by using 2-(4-chlorophenyl)-3-hydroxy-4-methylcarbonylthiophene and 5-hydrazinocarbonylthiophene-2-carboxylic acid 2-picolylamide prepared in Reference Synthetic Example 16 (yield 68%).
Morphology: yellow solid
LC/MS: conditions 3 retention time 3.10 (min)
LC/MS (ESI$^+$) m/z; 511, 513 [M+1]$^+$
LC/MS (ESI$^-$) m/z; 509, 511 [M−1]$^-$ Synthetic Example 26

Synthesis of 5-{1-[5-(4-chlorophenyl)-4-hydroxythiophen-3-yl]ethylidenehydrazinocarbonyl}thiophene-2-carboxylic acid 3-picolylamide Synthesis was carried out in the same manner as in Synthetic Example 17 by using 2-(4-chlorophenyl)-3-hydroxy-4-methylcarbonylthiophene and 5-hydrazinocarbonylthiophene-2-carboxylic acid 3-picolylamide prepared in Reference Synthetic Example 11 (yield 50%).
Morphology: yellow solid
LC/MS: conditions 3 retention time 2.72 (min)
LC/MS (ESI$^+$) m/z; 511, 513 [M+1]$^+$
LC/MS (ESI$^-$) m/z; 509, 511 [M−1]$^-$ Synthetic Example 27

Synthesis of 5-{1-[5-(4-chlorophenyl)-4-hydroxythiophen-3-yl]ethylidenehydrazinocarbonyl}thiophene-2-carboxylic acid methylamide Synthesis was carried out in the same manner as in Synthetic Example 19 by using 2-(4-chlorophenyl)-3-hydroxy-4-methylcarbonylthiophene and 5-hydrazinocarbonylthiophene-2-carboxylic acid methylamide prepared in Reference Synthetic Example 14 (yield 82%).
Morphology: pale yellow solid
LC/MS: conditions 6 retention time 4.62 (min)
LC/MS (ESI$^+$) m/z; 434, 436 [M+1]$^+$
LC/MS (ESI$^-$) m/z; 432, 434 [M−1]$^-$ Synthetic Example 28

Synthesis of 5-{1-[5-(3,4-dimethylphenyl)-4-hydroxythiophen-3-yl]ethylidenehydrazinocarbonyl]thiophene-2-carboxylic acid isopropylamide Synthesis was carried out in the same manner as in Synthetic Example 19 by using 2-(3,4-dimethylphenyl)-3-hydroxy-4-methylcarbonylthiophene (synthesized in accordance with WO2004/108683) and 5-hydrazinocarbonylthiophene-2-carboxylic acid isopropylamide prepared in Reference Synthetic Example 15 (yield 71%).
Morphology: pale yellow solid
LC/MS: conditions 2 retention time 4.40 (min)
LC/MS (ESI$^+$) m/z; 456 [M+1]$^+$
LC/MS (ESI$^-$) m/z; 454 [M−1]$^-$ Synthetic Example 29

Synthesis of 5-{1-[5-(3,4-dichlorophenyl)-4-hydroxythiophen-3-yl]ethylidenehydrazinocarbonyl}thiophene-2-carboxylic acid 2-picolylamide Synthesis was carried out in the same manner as in Synthetic Example 17 by using 2-(3,4-dichlorophenyl-3-hydroxy-4-methylcarbonylthiophene (synthesized in accordance with WO2004/108683) and 5-hydrazinocarbonylthiophene-2-carboxylic acid 2-picolylamide prepared in Reference Synthetic Example 16 (yield 65%).
Morphology: yellow solid
LC/MS: conditions 3 retention time 3.30 (min)
LC/MS (ESI$^+$) m/z; 545, 547 [M+1]$^+$
LC/MS (ESI$^-$) m/z; 543, 545 [M−1]$^-$ Synthetic Example 30

Synthesis of 5-{1-[5-(3,4-dichlorophenyl)-4-hydroxythiophen-3-yl]ethylidenehydrazinocarbonyl}thiophene-2-carboxylic acid 4-picolylamide Synthesis was carried out in the same manner as in Synthetic Example 17 by using 2-(3,4-dichlorophenyl)-3-hydroxy-4-methylcarbonylthiophene and 5-hydrazinocarbonylthiophene-2-carboxylic acid 4-picolylamide prepared in Reference Synthetic Example 12 (yield 51%).
Morphology: pale yellow solid
LC/MS: conditions 2 retention time 3.25 (min)
LC/MS (ESI$^+$) m/z; 545, 547 [M+1]$^+$
LC/MS (ESI$^-$) m/z; 543, 545 [M−1]$^-$

Synthetic Example 31

Synthesis of 5-{1-[5-(3,4-dichlorophenyl)-4-hydroxythiophen-3-yl]
ethylidenehydrazinocarbonyl}thiophene-2-carboxylic acid 2-(pyridin-4-yl)ethylamide 2-(3,4-Dichlorophenyl)-3-hydroxy-4-methylcarbonylthiophene (0.11 g, 0.38 mmol) and 5-hydrazinocarbonylthiophene-2-carboxylic acid (2-pyridin-4-yl)ethylamide (0.10 g, 0.34 mmol) prepared in Reference Synthetic Example 17 were suspended in N,N-dimethylformamide (2.0 mL) and left at 100° C. for 5 hours and then at room temperature for 20 hours. Water (0.20 mL) was added with stirring, and the precipitated solid was recovered by filtration, washed with chloroform and dried to give the desired product, 5-{1-[5-(3,4-dichlorophenyl)-4-hydroxythiophen-3-yl]ethylidenehydrazinocarbonyl}thiophene-2-carboxylic acid 2-(pyridin-4-yl)ethylamide (yield 66%).
Morphology: white solid
LC/MS: conditions 3 retention time 2.67 (min)
LC/MS (ESI$^+$) m/z; 559, 561 [M+1]$^+$

Synthetic Example 32

Synthesis of 5-{1-[5-(3,4-dichlorophenyl)-4-hydroxythiophen-3-yl]
ethylidenehydrazinocarbonyl}thiophene-2-carboxylic acid (1-methyl-1H-pyrazol-5-ylmethyl)amide 2-(3,4-Dichlorophenyl)-3-hydroxy-4-methylcarbonylthiophene (50 mg, 0.17 mmol) and 5-hydrazinocarbonylthiophene-2-carboxylic Acid (1-methyl-1H-pyrazol-5-ylmethyl)amide (49 mg, 0.17 mmol) prepared in Reference Synthetic Example 18 were dissolved in N,N-dimethylformamide (0.50 mL) and heated at 70° C. for 24 hours and cooled to room temperature. After addition of water, the precipitated crystals were recovered by filtration, washed with water and chloroform and dried to give the desired product (yield 76%).
Morphology: pale yellow solid
LC/MS: conditions 3 retention time 3.60 (min)
LC/MS (ESI$^+$) m/z; 548, 550 [M+1]$^+$
LC/MS (ESI$^-$) m/z; 546, 548 [M−1]$^-$

Synthetic Example 33

Synthesis of 5-{1-[5-(3,4-dichlorophenyl)-4-hydroxythiophen-3-yl]
ethylidenehydrazinocarbonyl}thiophene-2-carboxylic acid (5-methylisoxazol-3-ylmethyl)amide Synthesis was carried out in the same manner as in Synthetic Example 32 by using 2-(3,4-dichlorophenyl)-3-hydroxy-4-methylcarbonylthiophene and 5-hydrazinocarboynlthiophene-2-carboxylic acid (5-methylisoxazol-3-ylmethyl)amide prepared in Reference Synthetic Example 19 (yield 67%).
Morphology: yellow solid
LC/MS: conditions 3 retention time 3.77 (min)
LC/MS (ESI$^+$) m/z; 549, 551 [M+1]$^+$
LC/MS (ESI$^-$) m/z; 547, 549 [M−1]$^-$

Synthetic Example 34

Synthesis of 5-{1-[5-(3,4-dichlorophenyl)-4-hydroxythiophen-3-yl]
ethylidenehydrazinocarbonyl}thiophene-2-carboxylic acid (5-methylpyrazin-2-ylmethyl)amide Synthesis was carried out in the same manner as in Synthetic Example 17 by using 2-(3,4-dichlorophenyl)-3-hydroxy-4-methylcarbonylthiophene and 5-hydrazinocarbonylthiophene-2-carboxylic acid (5-methylpyrazin-2-ylmethyl)amide prepared in Reference Synthetic Example 20 (yield 74%).
Morphology: pale yellow solid
LC/MS: conditions 3 retention time 3.62 (min)
LC/MS (ESI$^+$) m/z; 560, 562 [M+1]$^+$
LC/MS (ESI$^-$) m/z; 558, 560 [M−1]$^-$

Synthetic Example 35

Synthesis of 5-{1-[5-(3,4-dichlorophenyl)-4-hydroxythiophen-3-yl]
ethylidenehydrazinocarbonyl}thiophene-2-carboxylic acid (isoxazol-5-ylmethyl)amide Synthesis was carried out in the same manner as in Synthetic Example 19 by using 2-(3,4-dichlorophenyl)-3-hydroxy-4-methylcarbonylthiophene and 5-hydrazinocarbonylthiophene-2-carboxylic acid (isoxazol-5-ylmethyl)amide prepared in Reference Synthetic Example 19 (yield 74%).
Morphology: pale yellow solid
LC/MS: conditions 3 retention time 3.69 (min)
LC/MS (ESI$^+$) m/z; 535, 537 [M+1]+
LC/MS (ESI$^-$) m/z; 533, 535 [M−1]$^-$

Synthetic Example 36

Synthesis of 5-{1-[5-(3,4-dichlorophenyl)-4-hydroxythiophen-3-yl]
ethylidenehydrazinocarbonyl}thiophene-2-carboxylic acid (3-methoxyisoxazol-5-ylmethyl)amide Synthesis was carried out in the same manner as in Synthetic Example 19 by using 2-(3,4-dichlorophenyl)-3-hydroxy-4-methylcarbonylthiophene and 5-hydrazinocarbonylthiophene-2-carboxylic acid (3-methoxyisoxazol-5-ylmethyl)amide prepared in Reference Synthetic Example 22 (yield 52%).
Morphology: pale yellow solid
LC/MS: conditions 3 retention time 3.75 (min)
LC/MS (ESI$^+$) m/z; 565, 567 [M+1]$^+$
LC/MS (ESI$^-$) m/z; 563, 565 [M−1]$^-$

Synthetic Example 37

Synthesis of 5-{1-[5-(3,4-dichlorophenyl)-4-hydroxythiophen-3-yl]
ethylidenehydrazinocarbonyl}thiophene-2-carboxylic acid (1,5-dimethyl-1H-pyrazol-3-ylmethyl)amide Synthesis was carried out in the same manner as in Synthetic Example 17 by using 2-(3,4-dichlorophenyl)-3-hydroxy-4-methylcarbonylthiophene and 5-hydrazinocarbonylthiophene-2-carboxylic acid (1,5-dimethyl-1H-pyrazol-3-ylmethyl)amide prepared in Reference Synthetic Example 23 (yield 86%).
Morphology: yellow solid
LC/MS: conditions 3 retention time 3.65 (min)
LC/MS (ESI$^+$) m/z; 562, 564 [M+1]$^+$
LC/MS (ESI$^-$) m/z; 560, 562 [M−1]$^-$ Synthetic Example 38

Synthesis of 5-{1-[5-(3,4-dichlorophenyl)-4-hydroxythiophen-3-yl]ethylidenehydrazinocarbonyl}thiophene-2-carboxylic acid (pyrazin-2-ylmethyl)amide Synthesis was carried out in the same manner as in Synthetic Example 17 by using 2-(3,4-dichlorophenyl)-3-hydroxy-4-methylcarbonylthiophene and 5-hydrazinocarbonylthiophene-2-carboxylic acid (pyrazin-2-ylmethyl)amide prepared in Reference Synthetic Example 24 (yield 88%).
Morphology: pale yellow solid
LC/MS: conditions 3 retention time 3.57 (min)
LC/MS (ESI$^+$) m/z; 546, 548 [M+1]$^+$
LC/MS (ESI$^-$) m/z; 544, 546 [M−1]$^-$ Synthetic Example 39

Synthesis of 4-[{5-(2-[1-{5-(3,4-dichlorophenyl)-4-hydroxythiophen-3-yl}ethylidene]hydrazinocarbonyl)thiophene-2-carboxamido}methyl]pyridine 1-oxide 2-(3,4-Dichlorophenyl)-3-hydroxy-4-methylcarbonylthiophene (32 mg, 0.11 mmol) and 4-[{5-hydrazniocarbonyl)thiophene-2-carboxamido}methyl]pyridine 1-oxide (30 mg, 0.10 mmol) prepared in Reference Synthetic Example 25 were suspended in N,N-dimethylformamide (0.60 mL) and stirred at 80° C. for 90 hours. After addition of 2-(3,4-dichlorophenyl)-3-hydroxy-4-methylcarbonylthiophene (26 mg, 0.091 mmol), the suspension was stirred at 80° C. for 24 hours, left at room temperature for 5 hours and concentrated to dryness to give a yellow crude paste (91 mg). The paste was suspended in chloroform (2.0 mL), and the insolubles were recovered by filtration and dried to give the desired product, 4-[{5-(2-[1-{5-(3,4-dichlorophenyl)-4-hydroxythiophen-3-yl}ethylidene]hydrazinocarbonyl)thiophene-2-carboxamido}methyl]pyridine 1-oxide (yield 52%).
Morphology: pale yellow solid
LC/MS: conditions 3 retention time 3.29 (min)
LC/MS (ESI$^+$) m/z; 561, 563 [M+1]$^+$
LC/MS (ESI$^-$) m/z; 559, 561 [M−1]$^-$ Synthetic Example 40

Synthesis of 5-{1-[5-(3,4-dichlorophenyl)-4-hydroxythiophen-3-yl]ethylidenehydrazinocarbonyl}thiophene-2-carboxylic acid 3-(pyridin-4-yl)propylamide 2-(3,4-Dichlorophenyl)-3-hydroxy-4-methylcarbonylthiophene (42 mg, 0.14 mmol) and 5-hydrazinocarbonylthiophene-2-carboxylic acid 3-(pyridin-4-yl)propylamide (40 mg, 0.13 mmol) prepared in Reference Synthetic Example 26 were dissolved in N,N-dimethylformamide (1.0 mL) and left at 70° C. for 16 hours and then at room temperature for 24 hours. Water (0.36 mL) was added with stirring, and the precipitated solid was recovered by filtration to give the desired product, 5-{1-[5-(3,4-dichlorophenyl)-4-hydroxythiophen-3-yl]ethylidenehydrazinocarbonyl}thiophene-2-carboxylic acid 3-(pyridin-4-yl)propylamide (yield 95%).
Morphology: pale yellow solid
LC/MS: conditions 2 retention time 3.31 (min)
LC/MS (ESI$^+$) m/z; 573, 575 [M+1]$^+$
LC/MS (ESI$^-$) m/z; 571, 573 [M−1]$^-$ Synthetic Example 41

Synthesis of 5-{1-[5-(4-trifluoromethylphenyl)-4-hydroxythiophen-3-yl]ethylidenehydrazinocarbonyl}thiophene-2-carboxylic acid (1-methyl-1H-imidazol-5-ylmethyl)amide Synthesis was carried out in the same manner as in Synthetic Example 17 by using 2-(4-trifluoromethylphenyl)-3-hydroxy-4-methylcarbonylthiophene and 5-hydrazinocarbonylthiophene-2-carboxylic acid (1-methyl-1H-imidazol-5-ylmethyl)amide prepared in Reference Synthetic Example 27 (yield 39%).
Morphology: pale yellow solid
LC/MS: conditions 2 retention time 3.02 (min)
LC/MS (ESI$^+$) m/z; 548 [M+1]$^+$
LC/MS (ESI$^-$) m/z; 546 [M−1]$^-$ Synthetic Example 42

Synthesis of 5-(3-hydroxypyrrolidine-1-carbonyl)thiophene-2-carboxylic acid {1-[5-(3,4-dichlorophenyl)-4-hydroxythiophen-3-yl]ethylidene}hydrazide Synthesis was carried out in the same manner as in Synthetic Example 2 by using 2-(3,4-dichlorophenyl)-3-hydroxy-4-methylcarbonyl)thiophene and 5-(3-hydroxypyrrolidine-1-carbonyl)thiophene-2-carbohydrazide prepared in Reference Synthetic Example 28 (yield 97%).
Morphology: yellow solid
LC/MS: conditions 6 retention time 3.47 (min)
LC/MS (ESI$^+$) m/z; 524, 526 [M+1]$^+$
LC/MS (ESI$^-$) m/z; 522, 524 [M−1]$^-$ Synthetic Example 43

Synthesis of 5-(3-hydroxypyrrolidine-1-carbonyl)thiophene-2-carboxylic acid {1-[5-(4-trifluoromethylphenyl)-4-hydroxythiophen-3-yl]ethylidene}hydrazide Synthesis was carried out in the same manner as in Synthetic Example 2 by using 2-(4-trifluoromethylphenyl)-3-hydroxy-4-methylcarbonyl)thiophene and 5-(3-hydroxypyrrolidine-1-carbonyl)thiophene-2-carbohydrazide prepared in Reference Synthetic Example 28 (yield 84%).
Morphology: pale yellow solid
LC/MS: conditions 6 retention time 3.34 (min)
LC/MS (ESI$^+$) m/z; 524, 525 [M+1]$^+$
LC/MS (ESI$^-$) m/z; 522, 523 [M−1]$^-$ The structures of the compounds obtained in the Reference Synthetic Examples and the Synthetic Examples are shown below.

Reference Synthetic Ex. 1
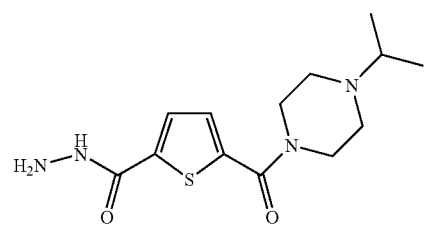

Reference Synthetic Ex. 2
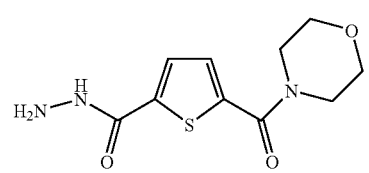

Reference Synthetic Ex. 3
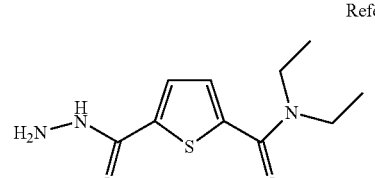

Reference Synthetic Ex. 4
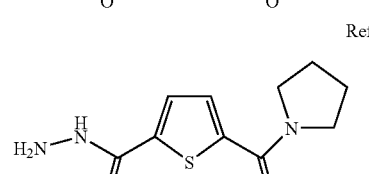

Reference Synthetic Ex. 5
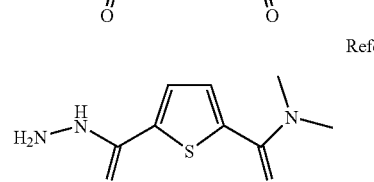

Reference Synthetic Ex. 6
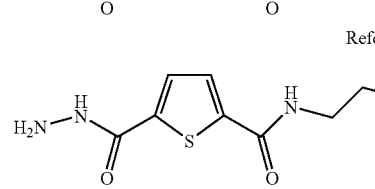

Reference Synthetic Ex. 7
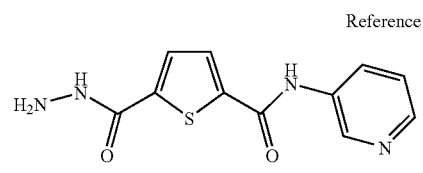

Reference Synthetic Ex. 8
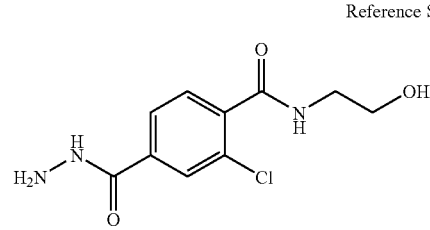

Reference Synthetic Ex. 9
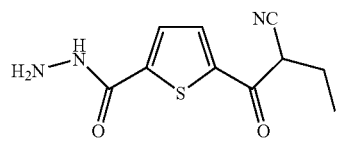

Reference Synthetic Ex. 10
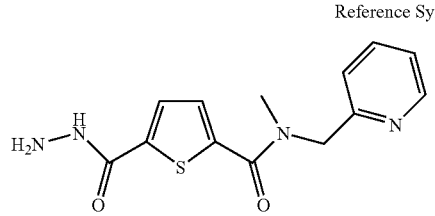

Reference Synthetic Ex. 11
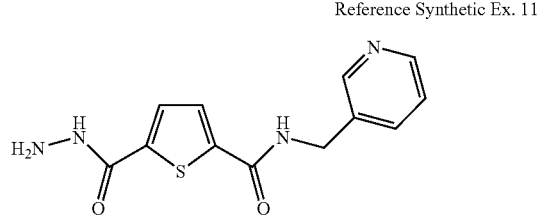

Reference Synthetic Ex. 12
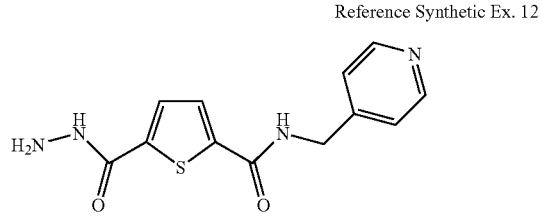

Reference Synthetic Ex. 13
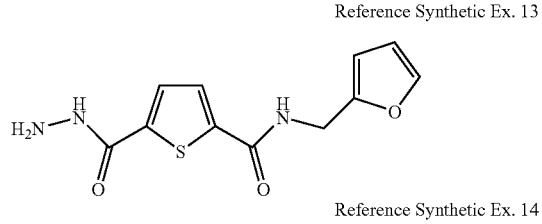

Reference Synthetic Ex. 14
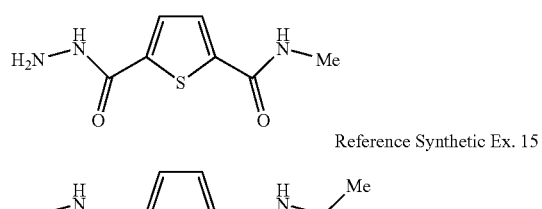

Reference Synthetic Ex. 15
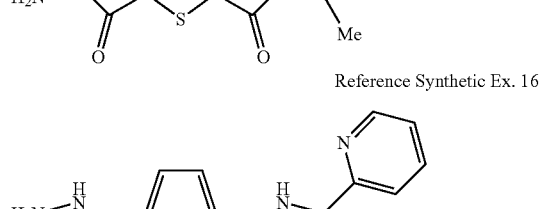

Reference Synthetic Ex. 16
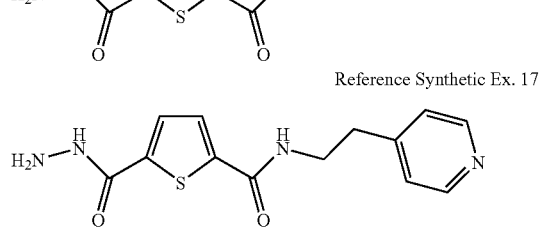

Reference Synthetic Ex. 17
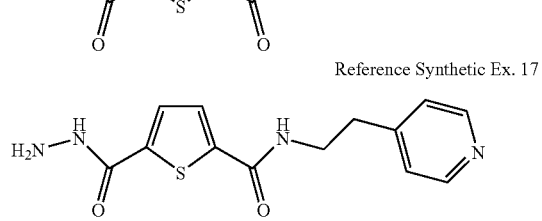

-continued

Reference Synthetic Ex. 18

Reference Synthetic Ex. 19

Reference Synthetic Ex. 20

Reference Synthetic Ex. 21

Reference Synthetic Ex. 22

Reference Synthetic Ex. 23

Reference Synthetic Ex. 24

-continued

Reference Synthetic Ex. 25

Reference Synthetic Ex. 26

Reference Synthetic Ex. 27

Reference Synthetic Ex. 28

Reference Synthetic Ex. 29

Patent document 26 Example 45

Reference Synthetic Ex. 30
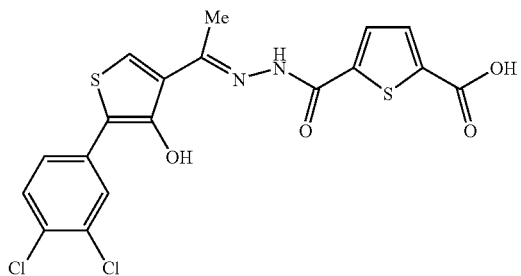
Patent document 26 Example 68
Synthetic Ex. 1
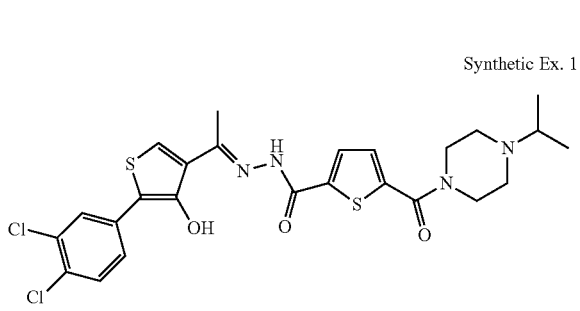
Synthetic Ex. 2
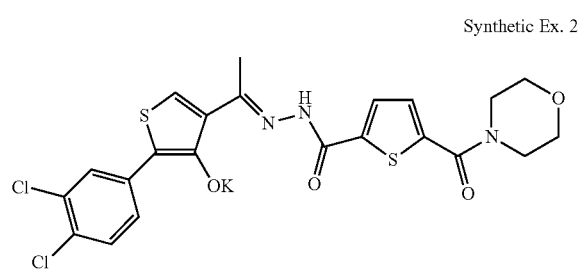
Synthetic Ex. 3
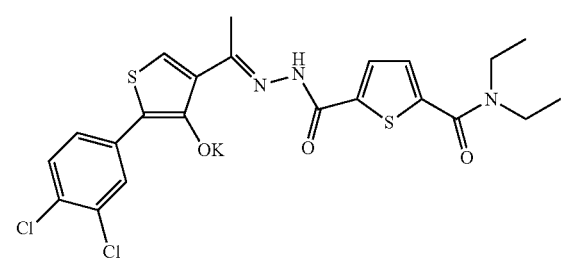
Synthetic Ex. 4
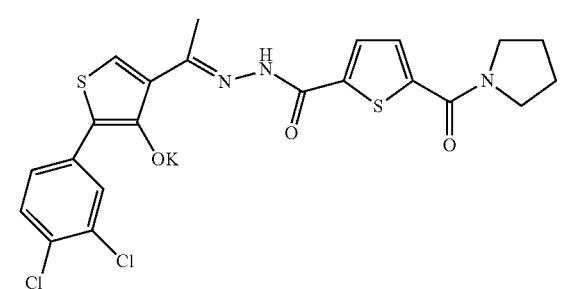
Synthetic Ex. 5
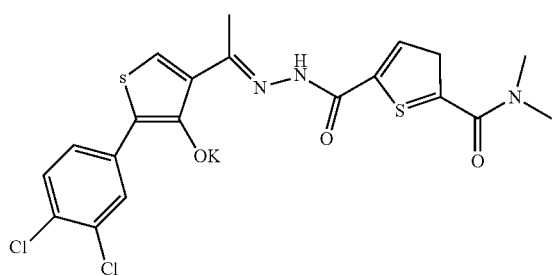
Synthetic Ex. 6
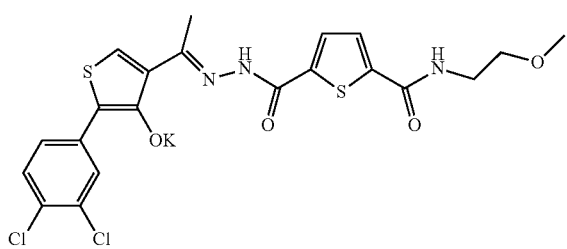
Synthetic Ex. 7
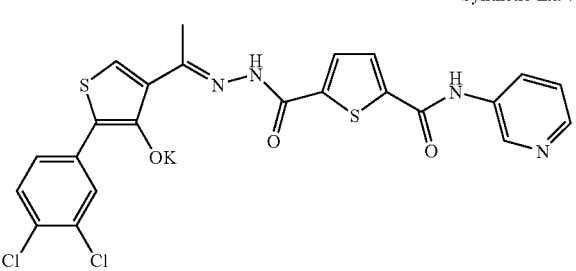
Synthetic Ex. 8
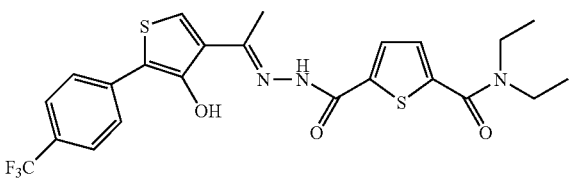
Synthetic Ex. 9
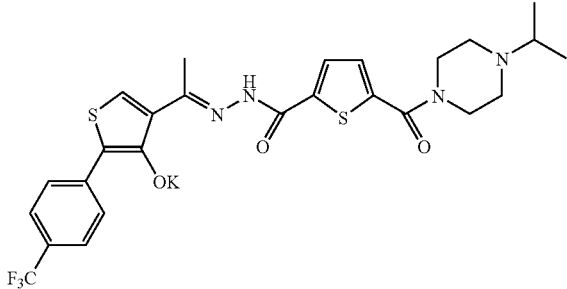

-continued

Synthetic Ex. 10

Synthetic Ex. 11

Synthetic Ex. 12

Synthetic Ex. 13

Synthetic Ex. 14

Synthetic Ex. 15

Synthetic Ex. 16

Synthetic Ex. 17

Synthetic Ex. 18

Synthetic Ex. 19

-continued
Synthetic Ex. 20
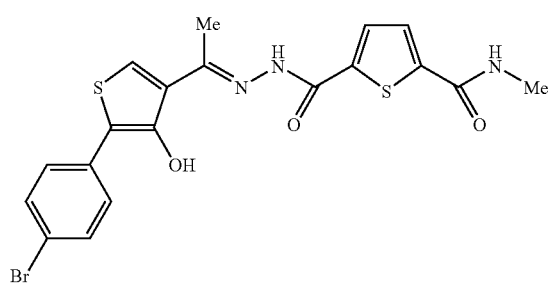
Synthetic Ex. 21
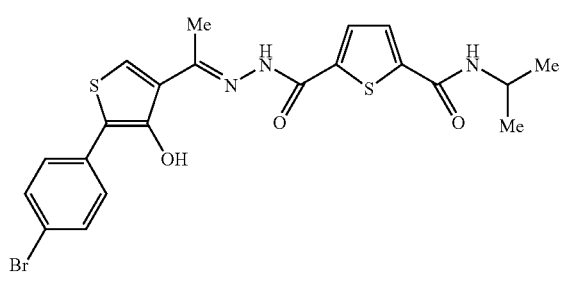
Synthetic Ex. 22
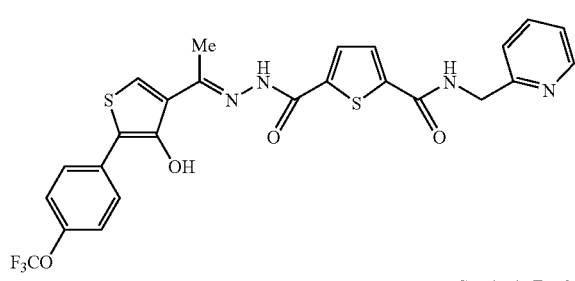
Synthetic Ex. 23
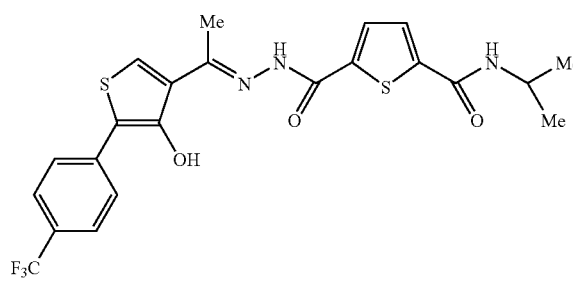
Synthetic Ex. 24
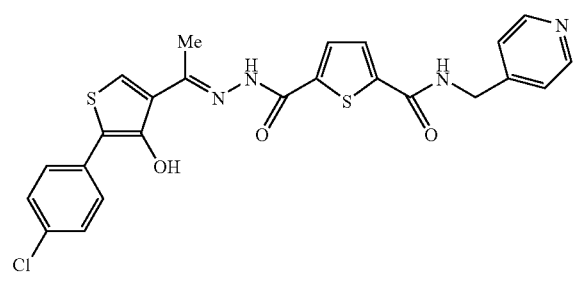
-continued
Synthetic Ex. 25
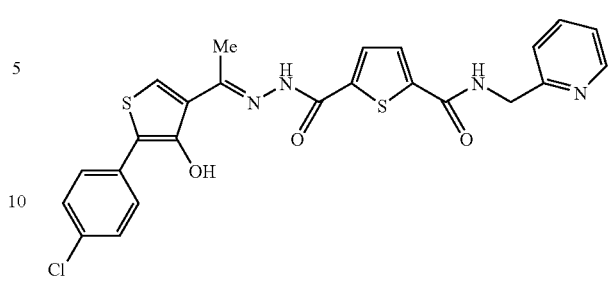
Synthetic Ex. 26
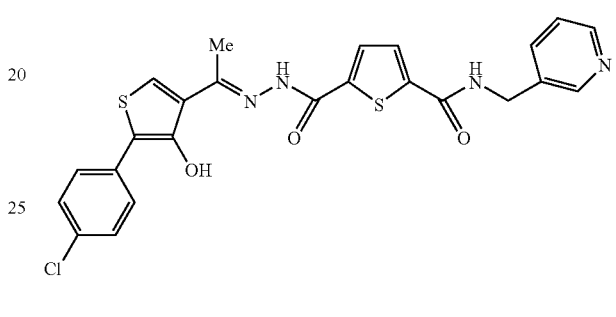
Synthetic Ex. 27
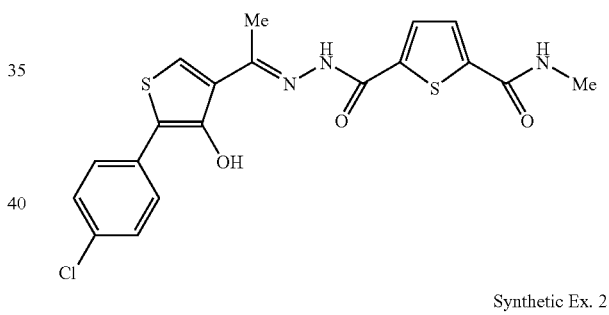
Synthetic Ex. 28
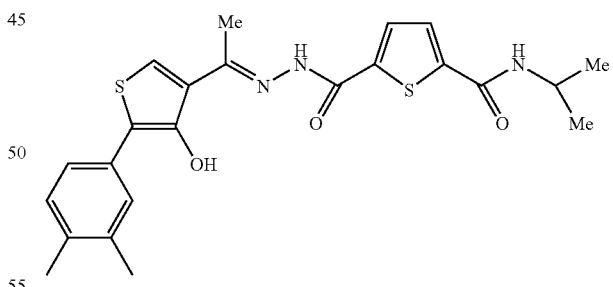
Synthetic Ex. 29
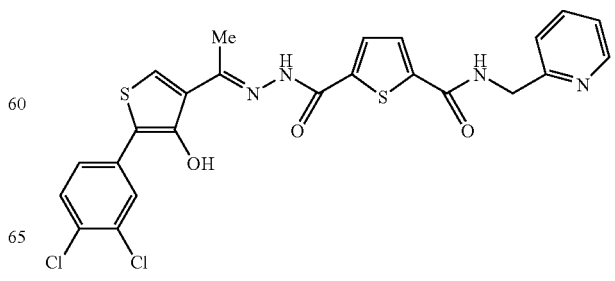

-continued
Synthetic Ex. 30
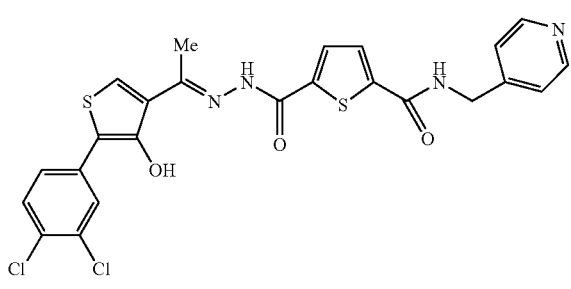
Synthetic Ex. 31
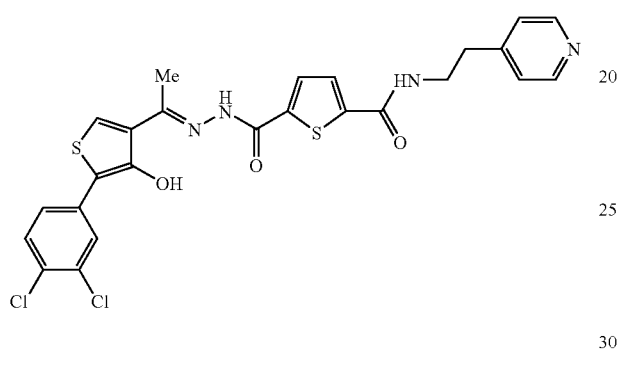
Synthetic Ex. 32
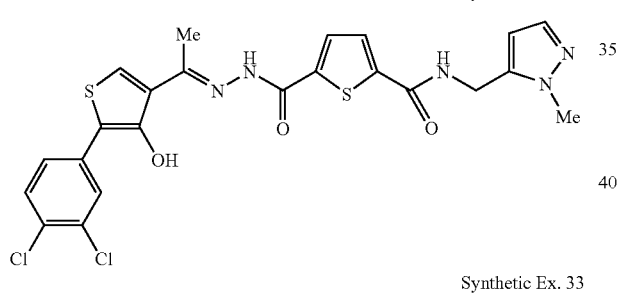
Synthetic Ex. 33
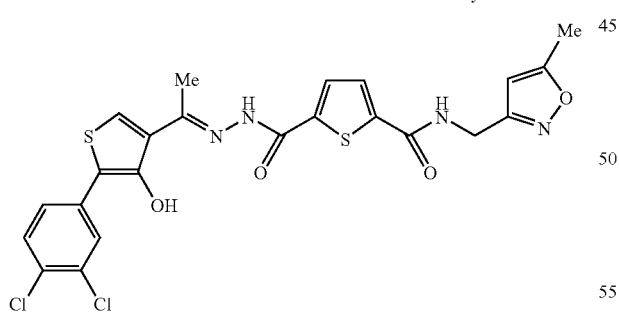
Synthetic Ex. 34
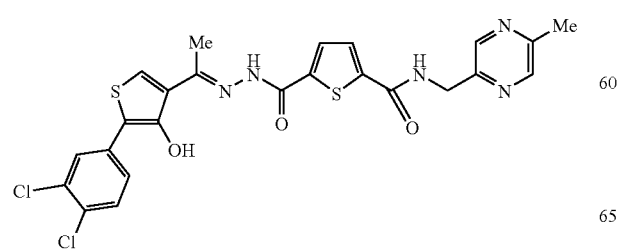
-continued
Synthetic Ex. 35
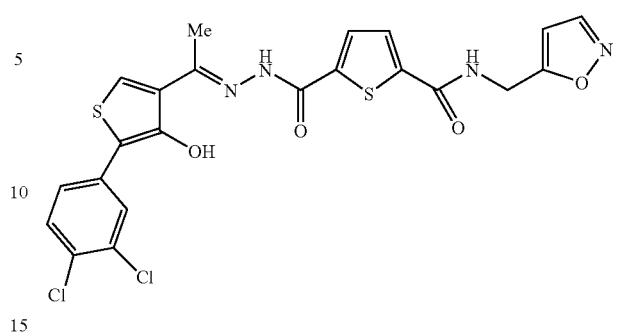
Synthetic Ex. 36
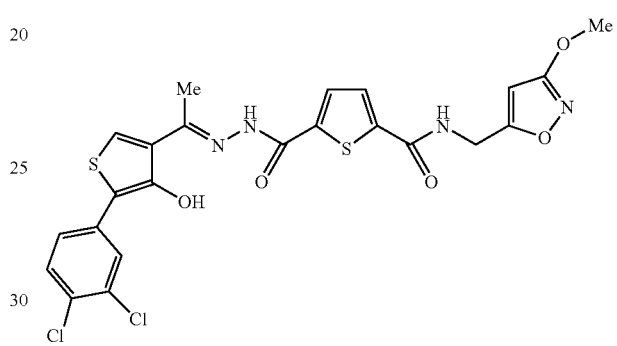
Synthetic Ex. 37
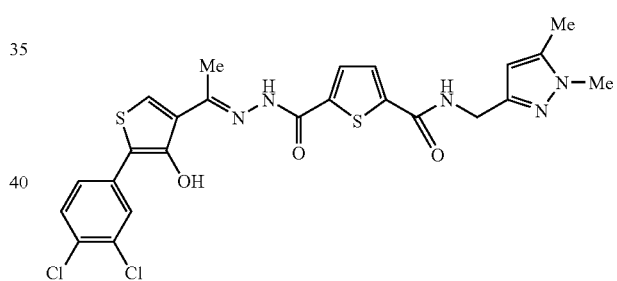
Synthetic Ex. 38
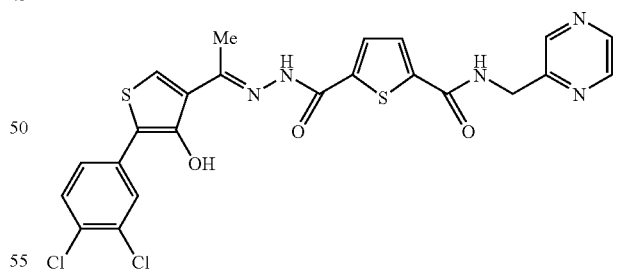
Synthetic Ex. 39
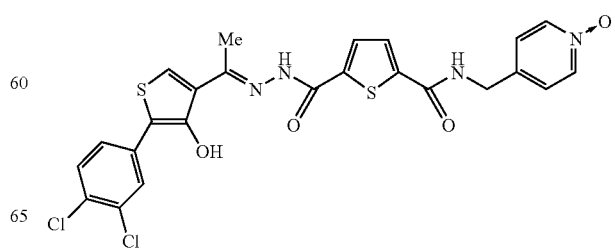

-continued

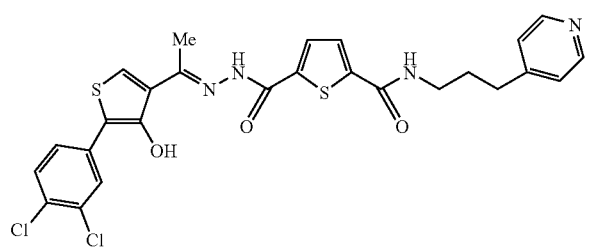

Synthetic Ex. 40

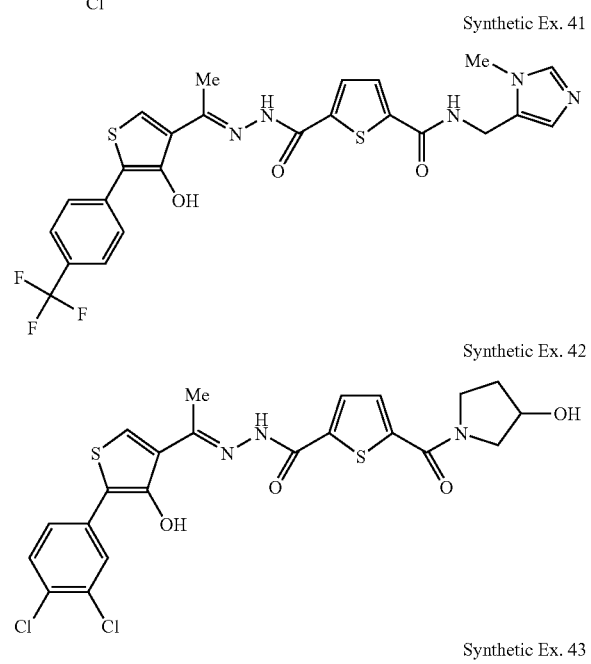

Synthetic Ex. 41

Synthetic Ex. 42

Synthetic Ex. 43

Assay Example 1

Stimulation of Proliferation of a Thrombopoietin-Dependent Cell Line

The reactivity of the compounds of the Synthetic Examples of the present invention with thrombopoietin (TPO) receptor was assayed using a human leukemic cell line, UT7/EPO-mpl.

(1) Cells and Cell Culture

UT7/EPO-mpl is a stable transformed cell line obtained by introducing into human leukemic cell line UT7/EPO a vector that induces expression of human thrombopoietin receptor (c-mpl) under control of cytomegalovirus immediate-early promoter by the method of Takatoku et al. (J. Biol. Chem., 272:7259-7263 (1997)). Proliferation of this cell line is stimulated by thrombopoietin, while its mother cell line UT7/EPO exhibits no response to thrombopoietin. These two cell lines were subcultured in IMDM (GIBCO) containing 10% fetal bovine serum (Thermo Electron or BioWest) using a $CO_2$ incubator (5% $CO_2$, 37° C.).

(2) Cell Proliferation Assay

The subcultured cells described above were washed twice with PBS and suspended in IMDM containing 10% fetal bovine serum at a cell density of $6 \times 10^4$ cells/mL. The cell suspension was transferred to a 96-well tissue culture plate (CORNING) in 100-μl aliquots. Then either thrombopoietin (PeproTech EC) or the compounds of the Synthetic Examples dissolved in dimethyl sulfoxide was diluted 83-fold with IMDM containing 10% fetal bovine serum and added to the aforementioned cell suspension in 20-μl aliquots. The cell suspension was incubated in a $CO_2$ incubator (5% $CO_2$, 37° C.) for 4 days. Cell proliferation was assayed using WST-8 reagent (Kishida Chemical Co., Ltd.) according to instructions by the manufacturer. A 10-μl aliquot of 5 mM WST-8 reagent solution was added to each well of the tissue culture plate, and the plate was incubated at 37° C. for 4 h. The formazan pigment generated was detected by measuring the absorbance at 450 nm with a 96-well microplate reader (Nihon Molecular Devices, Spectramax 190). Proliferation of thrombopoietin-responsive UT7/EPO-mpl cells was stimulated by the compounds of the Synthetic Examples of the present invention in a concentration-dependent manner, while no effect of the compounds of the Synthetic Examples on proliferation was observed with UT7/EPO, the mother cell line. These results indicate that the compounds of the Synthetic Examples of the present invention act on the thrombopoietin receptor selectively as its activators.

The compounds of Synthetic Examples 1 to 43 (in the free forms) were tested to determine the concentration of each compound that yields a growth rate corresponding to 50% of the growth of human leukemic cell line UT7/EPO-mpl observed in the presence of 10 ng/ml TPO ($EC_{50}$). The compounds of Synthetic Examples 1 to 43 all had $EC_{50}$ of about 10 ng/mL or below.

Assay Example 2

Each of the compounds of the Synthetic Examples was suspended in a 99/1 liquid mixture of 0.5% methylcellulose/Polyoxyethylene Sorbitan Monooleate and orally administered to 7-week-old male Sprague-Dawley rats (Japan SLC, Inc.) at a dose of 10 mg/kg/10 mL through a stomach tube. Between 0.5 and 2 hours after the administration of the compounds, blood was periodically collected from the cervical vein with heparin as the anticoagulant. The blood was centrifuged at 3500 $min^{-1}$ for 10 minutes to obtain plasma. The plasma was added to the assay system used for assay of proliferation of a thrombopoietin-dependent cell line UT7/EPO-mpl in Assay Example 1 at final concentrations of from 0.1 to 3%, and the cell proliferation was assayed. The concentration of each compound in plasma was calculated from the cell proliferation in the presence of plasma by comparison with a standard curve of cell proliferation versus compound concentration prepared for each compound or measured by LC/MS (Agilent Technologies, Agilent 1100 series LC/MS D). Each of the compounds of Synthetic Examples 1 to 16, 31 and 38 (Compounds of Synthetic Examples 31 and 38 were tested in the form of potassium salts) attained a maximum blood concentration (Cmax) of at least about 300 ng/mL 0.5 to 2 hours after the oral administration to rats.

Assay Example 3

Megakaryocyte Colony Stimulating Activity

The action of the compounds of Synthetic Examples 1 to 43 of the present invention and Reference Synthetic Examples 29 and 30 on the proliferation, differentiation and maturation of megakaryocyte cells was measured by the megakaryocyte colony forming method using human bone marrow cells. Human bone marrow CD34$^+$ cells (Cambrex Bio Science Walkersville) were incubated on 2-well chamber slide for 11 days in a $CO_2$ incubator (5% $CO_2$, 37° C.) using MegaCult™-C (StemCell Technologies) containing 0.1% (v/v) of the compounds of Synthetic Examples dissolved in dimethyl sulfoxide. After dehydration and fixation, the cells were stained with an anti-glycoprotein IIb/IIIa antibody in accordance with the instruction by the manufacturer. The colonies consisting of at least 8 stained megakaryocyte cells in each well were counted under a microscope. The megakaryocyte colony counts in at least 2 wells were averaged.

The results demonstrate that the compounds of the present invention have excellent megakaryocyte colony stimulating activity and increase platelets through the activity.

TABLE 7

| | Megakaryocyte colony count Drug Concentration (μg/mL) | | |
| --- | --- | --- | --- |
| Compound No. | 0.1 | 0.3 | 1 |
| Synthetic Ex. 1 | | | 154 |
| Synthetic Ex. 2 | | | 239 |
| Synthetic Ex. 3 | | | 348 |
| Synthetic Ex. 4 | 84 | | 148 |
| Synthetic Ex. 5 | | | 274 |
| Synthetic Ex. 6 | 115 | | 151 |
| Synthetic Ex. 8 | 147 | | 227 |
| Synthetic Ex. 10 | 105 | | 208 |
| Synthetic Ex. 13 | 61 | | |
| Synthetic Ex. 17 | | | 146 |
| Synthetic Ex. 18 | | | 125 |
| Synthetic Ex. 19 | | | 171 |
| Synthetic Ex. 20 | | | 185 |
| Synthetic Ex. 21 | 85 | | |
| Synthetic Ex. 22 | 96 | | |
| Synthetic Ex. 23 | | | 134 |
| Synthetic Ex. 24 | | | 164 |
| Synthetic Ex. 25 | | | 118 |
| Synthetic Ex. 26 | | | 182 |
| Synthetic Ex. 27 | | | 201 |
| Synthetic Ex. 28 | | | 105 |
| Synthetic Ex. 29 | 62 | | |
| Synthetic Ex. 30 | 145 | | 271 |
| Synthetic Ex. 31 | 70 | | 136 |
| Synthetic Ex. 32 | 55 | | |
| Synthetic Ex. 33 | 53 | | |
| Synthetic Ex. 34 | 50 | | |
| Synthetic Ex. 35 | 135 | | 153 |
| Synthetic Ex. 36 | 102 | | 135 |
| Synthetic Ex. 37 | 81 | | |
| Synthetic Ex. 38 | 66 | | |
| Synthetic Ex. 39 | 86 | | |
| Synthetic Ex. 40 | 70 | | |
| Synthetic Ex. 41 | 41 | | |
| Synthetic Ex. 42 | 90 | | |
| Synthetic Ex. 43 | 109 | | |
| Reference Synthetic Ex. 29 | 2 | | 31 |
| Reference Synthetic Ex. 30 | 12 | 34 | 87 |

Formulation Example 1

A granule preparation containing the following ingredients is prepared.
Ingredients

| | |
| --- | --- |
| Compound represented by the formula (I) | 10 mg |
| Lactose | 700 mg |
| Corn Starch | 274 mg |
| HPC-L | 16 mg |
| | 1000 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

Ingredients

| | |
| --- | --- |
| Compound represented by the formula (I) | 10 mg |
| Lactose | 79 mg |
| Corn Starch | 10 mg |
| Magnesium Stearate | 1 mg |
| | 100 mg |

A compound represented by the formula (I) and lactose are sifted through a 60-mesh sieve. Corn starch is sifted though a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.
Ingredients

| | |
| --- | --- |
| Compound represented by the formula (I) | 15 mg |
| Lactose | 90 mg |
| Corn Starch | 42 mg |
| HPC-L | 3 mg |
| | 150 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are is sifted through a shaking sieve (12/60 mesh). The granules are put in hard capsules No. 4, 150 mg each.

Formulation Example 4

A tablet preparation containing the following ingredients is prepared.
Ingredients

| Compound represented by the formula (I) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (I), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| Compound represented by the formula (I) | 100 mg |
| Saturated Fatty Acid Glyceride | 1000 mL |

Solutions having the above-mentioned composition are usually administered to a patient intravenously at a rate of 1 mL per 1 minute.

INDUSTRIAL APPLICABILITY

The compounds of the present invention which have affinity for thrombopoietin receptor and act as thrombopoietin receptor agonists are useful as preventive, therapeutic and improving agents for diseases against which activation of the thrombopoietin receptor is effective, especially as drugs for hematological disorders accompanied by abnormal platelet count and as drugs for diseases treated or prevented by stimulating differentiation and proliferation of vascular endothelial cells and endothelial progenitor cells, and are useful as medicines.

The invention claimed is:
1. A compound represented by the formula (I):

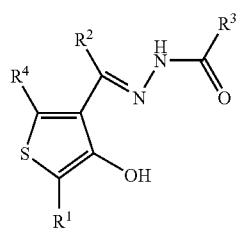

wherein
$R^1$ is: a phenyl group optionally substituted with one or more $C_{1-6}$ alkyl groups,
one or more $C_{1-3}$ alkyl groups substituted with one or more halogen atoms,
one or more $C_{1-3}$ alkoxy groups optionally substituted with one or more halogen atoms, or
one or more halogen atoms,
$R^2$ is: a hydrogen atom or
a $C_{1-3}$ alkyl group optionally substituted with one or more halogen atoms,
$R^3$ is: a thienyl group substituted with one or more substituents selected from the group consisting of:
hydrogen atoms,
nitro groups,
halogen atoms,
$C_{1-3}$ alkyl groups optionally substituted with one or more halogen atoms, and
$(C=O)R^5$, wherein
$R^5$ is $NR^6R^7$, wherein
$R^6$ is: a hydrogen atom or a $C_{1-3}$ alkyl group optionally substituted with one or more halogen atoms, and
$R^7$ is: a substituted $C_{1-6}$ alkyl group substituted with:
one or more halogen atoms,
one or more hydroxyl groups,
one or more $C_{1-3}$ alkoxy groups, or
one or more $C_{2-14}$ aryl groups,
where the one or more $C_{2-14}$ aryl groups may contain one to three heterocyclyl nitrogen atoms, oxygen atoms, and/or sulfur atoms,
where the one or more $C_{2-14}$ aryl groups may be substituted with one or more $C_{1-3}$ alkyl groups, one or more $C_{1-3}$ alkoxy groups, one or more carboxyl groups, one or more carbamoyl groups, one or more cyano groups, or one or more halogen atoms, and
where in the case of aryl groups containing one or more nitrogen atoms, optionally the N-oxides thereof,
a phenyl group optionally substituted with one or more halogen atoms,
a thienyl group optionally substituted with one or more halogen atoms,
a pyridyl group optionally substituted with one or more halogen atoms, or
a pyridyl-N-oxide group optionally substituted with one or more halogen atoms,
or $NR^6R^7$ is, as a whole, a nitrogen-containing heterocyclyl group optionally substituted with:
one or more hydrogen atoms,
one or more $C_{1-6}$ alkyl groups optionally substituted with one or more halogen atoms,
one or more halogen atoms,
one or more hydroxyl groups, or
one or more $C_{1-3}$ alkoxy groups optionally substituted with one or more halogen atoms,
or $R^5$ is a $C_{1-6}$ alkyl group optionally substituted with:
one or more halogen atoms,
one or more pyridyl groups,
one or more pyridyl-N-oxide groups,
one or more furyl groups,
one or more thienyl groups,
one or more phenyl groups, or
one or more cyano groups, and
$R^4$ is: a hydrogen atom or
a $C_{1-3}$ alkyl group optionally substituted with one or more halogen atoms;
a tautomer, prodrug or pharmaceutically acceptable salt of the compound.

2. The compound according to claim 1, wherein $R^2$ is a methyl group, and $R^4$ is a hydrogen atom, a tautomer, prodrug or pharmaceutically acceptable salt of the compound.

3. The compound according to claim 2, wherein $R^1$ is a 3,4-dimethyl-phenyl group, a 4-t-butyl-phenyl group, a 4-trifluoromethyl-phenyl group, a 3-chloro-phenyl group, a 4-chloro-phenyl group, a 4-fluoro-phenyl group, a 3,4-dichloro-phenyl group, a 4-bromo-phenyl group or a 4-trifluoromethoxy-phenyl group, a tautomer, prodrug or pharmaceutically acceptable salt of the compound.

4. The compound according to claim 3, wherein $R^3$ is represented by the formula (II):

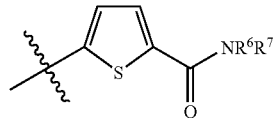
(II)

wherein $R^6$ is a methyl group or an ethyl group, and $R^7$ is a $C_{1-6}$ alkyl group substituted with one or more methoxy groups, a tautomer, prodrug or pharmaceutically acceptable salt of the compound.

5. The compound according to claim 3, wherein $R^3$ is represented by the formula (II):

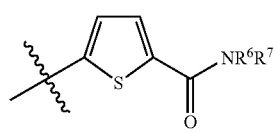
(II)

wherein $R^6$ is a methyl group or an ethyl group, and $R^7$ is a $C_{1-3}$ alkyl group substituted with one or more phenyl groups or one or more pyridyl groups, a tautomer, prodrug or pharmaceutically acceptable salt of the compound.

6. The compound according to claim 3, wherein $R^3$ is represented by the formula (II):

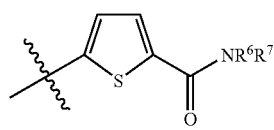
(II)

wherein $R^6$ is a hydrogen atom, and $R^7$ is a $C_{1-6}$ alkyl group substituted with one or more methoxy or $R^7$ is a pyridyl group, a tautomer, prodrug or pharmaceutically acceptable salt of the compound.

7. The compound according to claim 3, wherein $R^3$ is represented by the formula (II):

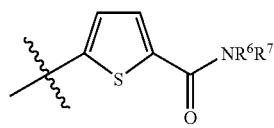
(II)

wherein $NR^6R^7$ is, as a whole, represented by one of the formulae (IIIA)-(IIIE)

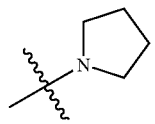
(IIIA)

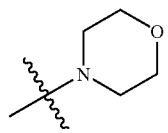
(IIIB)

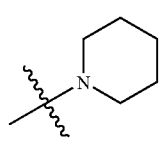
(IIIC)

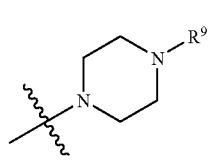
(IIID)

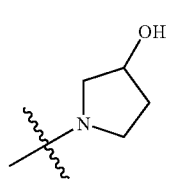
(IIIE)

wherein $R^9$ is a $C_{1-3}$ alkyl group, a tautomer, prodrug or pharmaceutically acceptable salt of the compound.

8. The compound according to claim 3, wherein $R^3$ is represented by the formula (V):

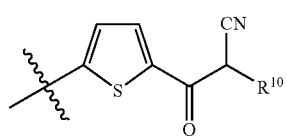
(V)

wherein $R^{10}$ is a hydrogen atom or a $C_{1-3}$ alkyl group, a tautomer, prodrug or pharmaceutically acceptable salt of the compound.

9. The compound according to claim 3, wherein $R^3$ is represented by the formula (II):

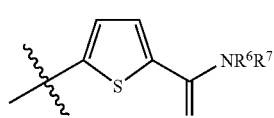
(II)

wherein $R^6$ is a hydrogen atom, and $R^7$ is a methyl group, an ethyl group or a normal propyl group;

wherein: methyl group, the ethyl group and the normal propyl group are substituted with
one or more pyridyl groups,
one or more pyridyl-N-oxide groups,
one or more furyl groups,
one or more pyrazinyl groups,
one or more imidazolyl groups,
one or more pyrazolyl groups or
one or more isoxazolyl groups,
wherein the pyridyl groups, the pyridyl-N-oxide groups, the furyl groups, the pyrazinyl groups, the imidazolyl groups, the pyrazolyl groups and the isoxazolyl groups may be substituted with one or more methyl groups, one or more methoxy groups, one or more carboxyl groups or one or more halogen atoms;
a tautomer, prodrug or pharmaceutically acceptable salt of the compound.

10. The compound according to claim 1, wherein $R^1$ is a 3,4-dimethyl-phenyl group, a tautomer, prodrug or pharmaceutically acceptable salt of the compound.

11. The compound according to claim 1, wherein $R^1$ is a 3,4-dichloro-phenyl group, a tautomer, prodrug or pharmaceutically acceptable salt of the compound.

12. The compound according to claim 1, wherein $R^1$ is a 4-chloro-phenyl group, a tautomer, prodrug or pharmaceutically acceptable salt of the compound.

13. The compound according to claim 1, wherein $R^1$ is a 4-trifluoromethyl-phenyl group, a tautomer, prodrug or pharmaceutically acceptable salt of the compound.

14. The compound according to claim 1, wherein $R^1$ is a 4-bromo-phenyl group, a tautomer, prodrug or pharmaceutically acceptable salt of the compound.

15. The compound according to claim 1, wherein $R^1$ is a 4-trifluoromethoxy-phenyl group, a tautomer, prodrug or pharmaceutically acceptable salt of the compound.

16. A pharmaceutical composition comprising at least one compound of claim 1, a tautomer, prodrug or pharmaceutically acceptable salt of the compound, as an active ingredient.

17. The pharmaceutical composition of claim 16, which comprises the active ingredient and at least one pharmaceutically acceptable additive.

18. A method of treating thrombocytopenia which comprises administering a compound of claim 1, a tautomer, prodrug or pharmaceutically acceptable salt of the compound, to a patient with thrombocytopenia.

19. A compound represented by the formula (I):

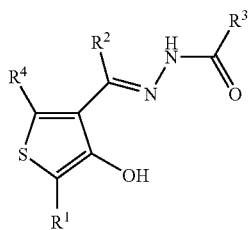

(I)

wherein
$R^1$ is: a phenyl group optionally substituted with one or more $C_{1-6}$ alkyl groups,
one or more $C_{1-3}$ alkyl groups substituted with one or more halogen atoms,
one or more $C_{1-3}$ alkoxy groups optionally substituted with one or more halogen atoms, or
one or more halogen atoms, $R^2$ is: a hydrogen atom or
a $C_{1-3}$ alkyl group optionally substituted with one or more halogen atoms,
$R^3$ is: a thienyl group substituted with one or more substituents selected from the group consisting of:
hydrogen atoms,
nitro groups,
halogen atoms,
$C_{1-3}$ alkyl groups optionally substituted with one or more halogen atoms, and
$(C=O)R^5$, wherein
$R^5$ is $NR^6R^7$, wherein
$R^6$ is: a $C_{1-3}$ alkyl group optionally substituted with one or more halogen atoms, and
$R^7$ is: a substituted $C_{1-6}$ alkyl group substituted with:
one or more halogen atoms,
one or more hydroxyl groups,
one or more $C_{1-3}$ alkoxy groups, or
one or more $C_{2-14}$ aryl groups,
where the one or more $C_{2-14}$ aryl groups may contain one to three heterocyclyl nitrogen atoms and/or oxygen atoms,
where (the one or more $C_{2-14}$ aryl groups may be optionally substituted with one or more $C_{1-3}$ alkyl groups, one or more $C_{1-3}$ alkoxy groups, one or more carboxyl groups, one or more carbamoyl groups, one or more cyano groups, or one or more halogen atoms, and
where in the case of aryl groups containing one or more nitrogen atoms, optionally the N-oxides thereof,
a phenyl group optionally substituted with one or more halogen atoms,
a thienyl group optionally substituted with one or more halogen atoms,
a pyridyl group optionally substituted with one or more halogen atoms, or
a pyridyl-N-oxide group optionally substituted with one or more halogen atoms,
or $NR^6R^7$ is, as a whole, a nitrogen-containing heterocyclyl group optionally substituted with:
one or more hydrogen atoms,
one or more $C_{1-6}$ alkyl groups optionally substituted with one or more halogen atoms,
one or more halogen atoms,
one or more hydroxyl groups, or
one or more $C_{1-3}$ alkoxy groups optionally substituted with one or more halogen atoms))) atoms,
or $R^5$ is a $C_{1-6}$ alkyl group substituted with:
one or more halogen atoms,
one or more pyridyl groups,
one or more pyridyl-N-oxide groups,
one or more furyl groups,
one or more thienyl groups,
one or more phenyl groups, or one or more cyano groups, and
$R^4$ is a hydrogen atom or
a $C_{1-3}$ alkyl group optionally substituted with one or more halogen atoms;
a tautomer, prodrug or pharmaceutically acceptable salt of the compound.

20. A pharmaceutical composition comprising at least one compound of claim 19, a tautomer, prodrug or pharmaceutically acceptable salt of the compound, as an active ingredient.

21. The pharmaceutical composition of claim 20, which comprises the active ingredient and at least one pharmaceutically acceptable additive.

22. A method of treating thrombocytopenia which comprises administering a compound of claim 19, a tautomer, prodrug or pharmaceutically acceptable salt of the compound, to a patient with thrombocytopenia.

23. A compound, a tautomer thereof or a pharmaceutically acceptable salt thereof which is
   (i) 5-(4-isopropylpiperazine-1-carbonyl)thiophene-2-carboxylic acid {1-[5-(3,4 dichlorophenyl)-4-hydroxythiophen-3-yl]ethylidene}hydrazide,
   (ii) 5-(morpholine-4-carbonyl)thiophene-2-carboxylic acid {1-[5-(3,4-dichlorophenyl)-4-hydroxythiophen-3-yl]ethylidene}hydrazide,
   (iii) 5-(pyrrolidine-1-carbonyl)thiophene-2-carboxylic acid {1-[5-(3,4-dichlorophenyl)-4-hydroxythiophen-3-yl]ethylidene}hydrazide,
   (iv) 5-[(2-{1-[5-(3,4-dichlorophenyl)-4-hydroxythiophen-3-yl)ethylidene}hydrazino)carbonyl]thiophene-2-carboxylic acid 2-methoxyethylamide,
   (v) 5-(pyrrolidine-1-carbonyl)thiophene-2-carboxylic acid {1-[5-(4-trifluoromethylphenyl)-4-hydroxythiophen-3-yl]ethylidene}hydrazide,
   (vi) 5-[(2-{1-[5-(4-trifluoromethylphenyl)-4-20 hydroxythiophen-3-yl]ethylidene}hydrazino)carbonyl] thiophene-2-carboxylic acid methyl-2-picolylamide,
   (vii) 5-[(2-{1-[5-(4-bromophenyl)-4-hydroxythiophen-3-yl]ethylidene}hydrazino)carbonyl]thiophene-2-carboxylic acid 3-picolylamide,
   (viii) 5-[(2-{1-[5-(4-bromophenyl)-4-hydroxythiophen-3-yl]ethylidene}hydrazino) carbonyl]thiophene-2-carboxylic acid 4-picolylamide,
   (ix) 5-[(2-{1-[5-(4-bromophenyl)-4-hydroxythiophen-3-yl]ethylidene}hydrazino)carbonyl]thiophene-2-carboxylic acid furan-2-ylmethylamide,
   (x) 5-[(2-{1-[5-(4-bromophenyl)-4-hydroxythiophen-3-yl]ethylidene}hydrazino)carbonyl]thiophene-2-carboxylic acid isopropylamide,
   (xi) 5-[(2-{1-[4-hydroxy-5-(4-trifluoromethoxyphenyl) thiophen-3-yl]ethylidene}hydrazino) carbonyl] thiophene-2-carboxylic acid 2-picolylamide,
   (xii) 5-[(2-{1-[5-(4-trifluoromethylphenyl)-4-hydroxythiophen-3-yl]ethylidene}hydrazino)carbonyl] thiophene-2-carboxylic acid isopropylamide,
   (xiii) 5-[(2-{1-[5-(4-chlorophenyl)-4-hydroxythiophen-3-yl]ethylidene}hydrazino)carbonyl]thiophene-2-carboxylic acid 4-picolylamide,
   (xiv) 5-[(2-{1-[5-(4-chlorophenyl)-4-hydroxythiophen-3-yl]ethylidene}hydrazino)carbonyl]thiophene-2-carboxylic acid 2-picolylamide,
   (xv) 5-[(2-{1-[5-(4-chlorophenyl)-4-hydroxythiophen-3-yl]ethylidene}hydrazino)carbonyl]thiophene-2-carboxylic acid 3-picolylamide,
   (xvi) 5-[(2-{1-[5-(3,4-dimethylphenyl)-4-hydroxythiophen-3-yl]ethylidene}hydrazino)carbonyl] thiophene-2-carboxylic acid isopropylamide,
   (xvii) 5-[(2-{1-[5-(3,4-dichlorophenyl)-4-hydroxythiophen-3-yl]ethylidene}hydrazino)carbonyl] thiophene-2-carboxylic acid 2-picolylamide,
   (xviii) 5-[(2-{1-[5-(3,4-dichlorophenyl)-4-hydroxythiophen-3-yl]ethylidene}hydrazino)carbonyl] thiophene-2-carboxylic acid 4-picolylamide,
   (xix) 5-[(2-{1-[5-(3,4-dichlorophenyl)-4-hydroxythiophen-3-yl]ethylidene}hydrazino)carbonyl] thiophene-2-carboxylic acid 2-(pyridin-4-yl)ethylamide,
   (xx) 5-[(2-{1-[5-(3,4-dichlorophenyl)-4-hydroxythiophen-3-yl]ethylidene}hydrazino)carbonyl) thiophene-2-carboxylic acid [(1-methyl-1H-pyrazol-5-yl)methyl]amide,
   (xxi) 5-[(2-{1-[5-(3,4-dichlorophenyl)-4-hydroxythiophen-3-yl]ethylidene}hydrazino)carbonyl] thiophene-2-carboxylic acid (5-methylisoxazol-3-ylmethyl)amide,
   (xxii) 5-[(2-{1-[5-(3,4-dichlorophenyl)-4-hydroxythiophen-3-yl]ethylidene}hydrazino)carbonyl] thiophene-2-carboxylic acid (5-methylpyrazin-2-ylmethyl) amide,
   (xxiii) 5-[(2-{1-[5-(3,4-dichlorophenyl)-4-hydroxythiophen-3-yl]ethylidene}hydrazino)carbonyl] thiophene-2-carboxylic acid (isoxazol-5-ylmethyl) amide,
   (xxiv) 5-[(2-{1-[5-(3,4-dichlorophenyl)-4-hydroxythiophen-3-yl]ethylidene}hydrazino)carbonyl] thiophene-2-carboxylic acid (3-methoxyisoxazol-5-ylmethyl) amide,
   (xxv) 5-[(2-{1-[5-(3,4-dichlorophenyl)-4-hydroxythiophen-3-yl]ethylidene}hydrazino)carbonyl] thiophene-2-carboxylic acid (1,5-dimethyl-1H-pyrazol-3-ylmethyl) amide,
   (xxvi) 5-[(2-{1-(5-(3,4-dichlorophenyl)-4-hydroxythiophen-3-yl]ethylidene}hydrazino)carbonyl] thiophene-2-carboxylic acid (pyrazin-2-ylmethyl) amide,
   (xxvii) 5-(2-{1-(5-(3,4-dichlorophenyl)-4-hydroxythiophen-3-yl]ethylidene}hydrazino)carbonyl] thiophene-2-carboxylic acid 4-picolyl-1-oxide-amide,
   (xxviii) 5-[(2-(1-[5-(3,4-dichlorophenyl)-4-hydroxythiophen-3-yl]ethylidene}hydrazino)carbonyl] thiophene-2-carboxylic acid 3-(pyridin-4-yl)propylamide,
   (xxiv) 5-[(2-{1-(5-(4-trifluoromethylphenyl)-4-hydroxythiophen-3-yl]ethylidene}hydrazino)carbonyl] thiophene-2-carboxylic acid [(1-methyl-1H-imidazol-5-yl)methyl]amide,
   (xxx) 5-(3-hydroxypyrrolidine-1-carbonyl)thiophene-2-carboxylic acid {1-[5-(3,4-dichlorophenyl)-4-hydroxythiophen-3-yl)ethylidene}hydrazide, or
   (xxxi) 5-(3-hydroxypyrrolidine-1-carbonyl)thiophene-2-carboxylic acid {1-[5-(4-trifluoromethylphenyl)-4~hydroxythiophen-3-yl)ethylidene}hydrazide.

24. 5-[(2-{1-[5-(3,4-Dichlorophenyl)-4-hydroxythiophen-3-yl]ethylidene}hydrazino)carbonyl]thiophene-2-carboxylic acid 2-methoxyethylamide, a tautomer thereof or a pharmaceutically acceptable salt thereof.

25. 5-(Pyrrolidine-1-carbonyl)thiophene-2-carboxylic acid {1-[5-(4-trifluoromethylphenyl)-4-hydroxythiophen-3-yl]ethylidene}hydrazide, a tautomer thereof or a pharmaceutically acceptable salt thereof.

26. 5-[(2-{1-[5-(3,4-Dichlorophenyl)-4-hydroxythiophen-3-yl]ethylidene}hydrazino)carbonyl]thiophene-2-carboxylic acid 4-picolylamide, a tautomer thereof or a pharmaceutically acceptable salt thereof.

27. 5-[(2-{1-[5-(3,4-Dichlorophenyl)-4-hydroxythiophen-3-yl]ethylidene}hydrazino)carbonyl]thiophene-2-carboxylic acid 2-(pyridin-4-yl)ethylamide, a tautomer thereof or a pharmaceutically acceptable salt thereof.

28. 5-[(2-{1-[5-(3,4-Dichlorophenyl)-4-hydroxythiophen-3-yl]ethylidene}hydrazino)carbonyl]thiophene-2-carboxylic acid (isoxazol-5-ylmethyl)amide, a tautomer thereof or a pharmaceutically acceptable salt thereof.

29. 5-[(2-{1-[5-(3,4-Dichlorophenyl)-4-hydroxythiophen-3-yl]ethylidene}hydrazino)carbonyl]thiophene- 2-carboxylic acid (3-methoxyisoxazol-5-ylmethyl)amide, a tautomer thereof or a pharmaceutically acceptable salt thereof.

30. 5-[(2-{1-[5-(3,4-Dichlorophenyl)-4-hydroxythiophen-3-yl]ethylidene}hydrazino)carbonyl)thiophene-2-carboxylic acid (pyrazin-2-ylmethyl)amide, a tautomer thereof or a pharmaceutically acceptable salt thereof.

31. 5-(3-Hydroxypyrrolidine-1-carbonyl)thiophene-2-carboxylic acid {1-[5-(4-trifluoromethylphenyl)-4-hydroxythiophen-3-yl]ethylidene}hydrazide, a tautomer thereof or a pharmaceutically acceptable salt thereof.

32. A method of treating thrombocytopenia which comprises administering a compound of any one of claims 23-31, a tautomer, prodrug or pharmaceutically acceptable salt of the compound, to a patient with thrombocytopenia.

33. A compound according to claim 1 represented by the formula (I):

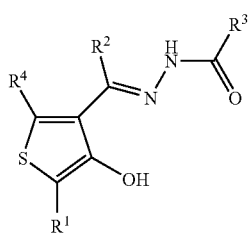

(I)

wherein
$R^1$ is: a phenyl group substituted with
  one or more $C_{1-6}$ alkyl groups,
  one or more $C_{1-3}$ alkyl groups substituted with one or more halogen atoms,
  one or more $C_{1-3}$ alkoxy groups optionally substituted with one or more halogen atoms, or
  one halogen atom,
$R^2$ is: a hydrogen atom or
  a $C_{1-3}$ alkyl group optionally substituted with one or more halogen atoms,
$R^3$ is: a thienyl group substituted with one or more substituents selected from the group consisting of:
  hydrogen atoms,
  nitro groups,
  halogen atoms,
  $C_{1-3}$ alkyl groups optionally substituted with one or more halogen atoms, and
  (C=O)$R^5$, wherein
    $R^5$ is $NR^6R^7$, wherein
      $R^6$ is: a hydrogen atom or a $C_{1-3}$ alkyl group optionally substituted with one or more halogen atoms, and
      $R^7$ is: a substituted $C_{1-6}$ alkyl group substituted with:
        one or more halogen atoms,
        one or more hydroxyl groups,
        one or more $C_{1-3}$ alkoxy groups, or
        one or more $C_{2-14}$ aryl groups, where the one or more $C_{2-14}$ aryl groups may contain one to three heterocyclyl nitrogen atoms and/or oxygen atoms,
where the one or more $C_{2-14}$ aryl groups may be optionally substituted with one or more $C_{1-3}$ alkyl groups, one or more $C_{1-3}$ alkoxy groups, one or more carboxyl groups, one or more carbamoyl groups, one or more cyano groups, or one or more halogen atoms, and
where in the case of aryl groups containing one or more nitrogen atoms, optionally the N-oxides thereof,
a phenyl group optionally substituted with one or more halogen atoms,
a thienyl group optionally substituted with one or more halogen atoms,
a pyridyl group optionally substituted with one or more halogen atoms, or
a pyridyl-N-oxide group optionally substituted with one or more halogen atoms,
or $NR^6R^7$ is, as a whole, a nitrogen-containing heterocyclyl group optionally substituted with:
  one or more hydrogen atoms,
  one or more $C_{1-6}$ alkyl groups optionally substituted with one or more halogen atoms,
  one or more halogen atoms,
  one or more hydroxyl groups, or
  one or more $C_{1-3}$ alkoxy groups optionally substituted with one or more halogen atoms,
or $R^5$ is a $C_{1-6}$ alkyl group optionally substituted with:
  one or more halogen atoms,
  one or more pyridyl groups,
  one or more pyridyl-N-oxide groups,
  one or more furyl groups,
  one or more thienyl groups,
  one or more phenyl groups, or
  one or more cyano groups, and
$R^4$ is: a hydrogen atom or
  a $C_{1-3}$ alkyl group optionally substituted with one or more halogen atoms;
a tautomer, prodrug or pharmaceutically acceptable salt of the compound.

34. The compound according to claim 1, which is 5-{1-[5-(3,4-dichlorophenyl)-4-hydroxythiophen-3-yl]ethylidenehydrazino carbonyl}thiophene-2-carboxylic acid 4-picolylamide.

35. The compound according to claim 1, which is 5-{1-[5-(3,4-dichlorophenyl)-4-hydroxythiophen-3-yl]ethylidenehydrazinocarbonyl}thiophene-2-carboxylic acid 2-(pyridine-4-yl)ethylamide.

36. The compound according to claim 1, which is 5-{1-[5-(3,4-dichlorophenyl)-4-hydroxythiophen-3-yl]ethylidenehydrazinocarbonyl}thiophene-2-carboxylic acid (pyridine-4-yl-methyl) amide.

37. The compound according to claim 1, which is 5-{1-[5-(3,4-dichlorophenyl)-4-hydroxythiophen-3-yl]ethylidenehydrazinocarbonyl}thiophene-2-carboxylic acid (pyrazin-2-yl-methyl) amide.

* * * * *